US012599778B2

(12) United States Patent
Dolgoff

(10) Patent No.: US 12,599,778 B2
(45) Date of Patent: Apr. 14, 2026

(54) PRECISE TARGETING OF BENEFICIAL EFFECTS OF COHERENT ENERGY USING NANOPARTICLES

(71) Applicant: Holobeam Technologies Inc., Westbury, NY (US)

(72) Inventor: Gene Dolgoff, Westbury, NY (US)

(73) Assignee: Holobeam Technologies Inc., Bethpage, NY (US)

( * ) Notice: Subject to any disclaimer, the term of this patent is extended or adjusted under 35 U.S.C. 154(b) by 0 days.

(21) Appl. No.: 19/032,016

(22) Filed: Jan. 18, 2025

(65) Prior Publication Data

US 2025/0235713 A1     Jul. 24, 2025

Related U.S. Application Data

(60) Continuation of application No. 17/860,002, filed on Jul. 7, 2022, now Pat. No. 12,280,268, which is a division of application No. 17/055,921, filed as application No. PCT/US2019/032539 on May 15, 2019, now Pat. No. 11,400,306.

(60) Provisional application No. 62/671,632, filed on May 15, 2018.

(51) Int. Cl.
| | |
|---|---|
| *A61N 5/06* | (2006.01) |
| *A61F 7/00* | (2006.01) |
| *A61N 1/40* | (2006.01) |
| *A61N 5/10* | (2006.01) |
| *G01R 33/48* | (2006.01) |
| *G01R 33/50* | (2006.01) |

(52) U.S. Cl.
CPC .................. *A61N 5/06* (2013.01); *A61F 7/00* (2013.01); *A61N 1/40* (2013.01); *A61N 2005/063* (2013.01); *A61N 5/10* (2013.01); *G01R 33/4804* (2013.01); *G01R 33/50* (2013.01)

(58) Field of Classification Search
CPC ... A61N 5/06; A61N 1/40; A61N 5/10; A61N 2005/063; A61F 7/00; G01R 33/4804; G01R 33/50
USPC .......................................................... 607/88
See application file for complete search history.

*Primary Examiner* — Aaron F Roane

(74) *Attorney, Agent, or Firm* — Elman IP; Gerry J. Elman

(57) ABSTRACT

By producing the proper wave interference using superimposed angularly separate waves that overlap with the proper time-phase relationship (called "Time-Correlated Standing-wave Interference"), wave energy is amplified (by "Coherent Intensity Amplification") and teleported to precise locations. For instance, in one application, energy is teleported to one or more areas within a living body for such therapeutic applications as destroying cancer cells or plaques within arteries. A system implementing this technique creates amplified constructive interference at one or more selected disease locations, while producing destructive interference at surrounding locations. In this application example, the technique allows energy to be "teleported" to tumor cells, plaques, or other diseased cells, for instance, to destroy them, while surrounding healthy cells receive virtually no energy, obviating collateral damage from the treatment. The same method can be used to diagnose disease by detecting energy teleported to different locations.

17 Claims, 31 Drawing Sheets destructive interference constructive interference resultant wave interfering waves photographic
plate crystal X-rays diffracted
beams difraction pattern Photographic plate

440

430

420

400

Table 1  Normalized wave number at $n = 0$.

| $m$ | $\mu_{nm}$ | $m$ | $\mu_{nm}$ |
|-----|------------|-----|------------|
| 1 | 1.25 | 7 | 19.66 |
| 2 | 4.07 | 8 | 22.8 |
| 3 | 7.15 | 9 | 25.94 |
| 4 | 10.27 | 10 | 29.08 |
| 5 | 13.39 | 11 | 32.22 |
| 6 | 16.53 | 12 | 35.36 |

Fig. 5D

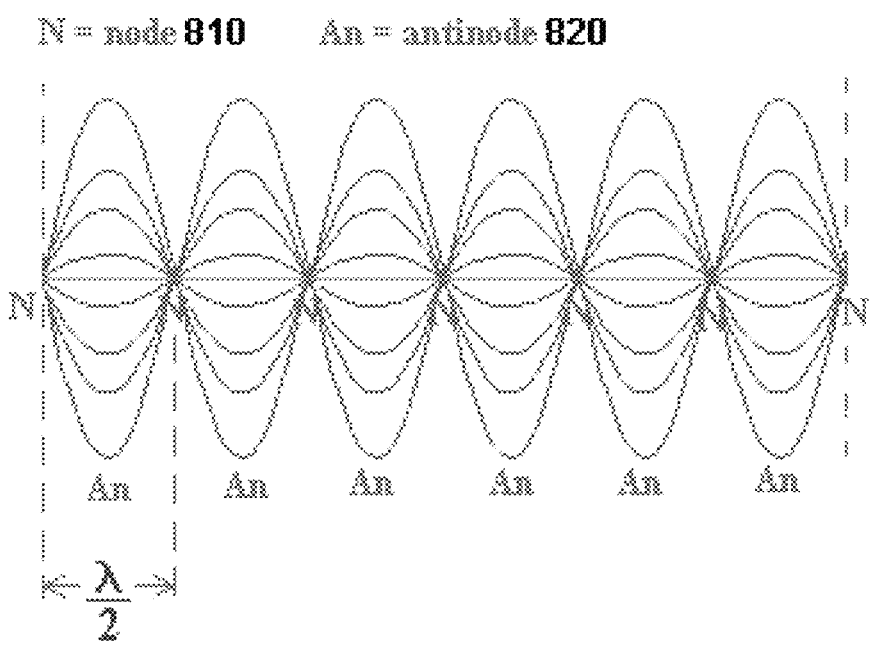
STANDING WAVES 800          Fig. 8A
N = node 810          An = antinode 820
Fig. 8B
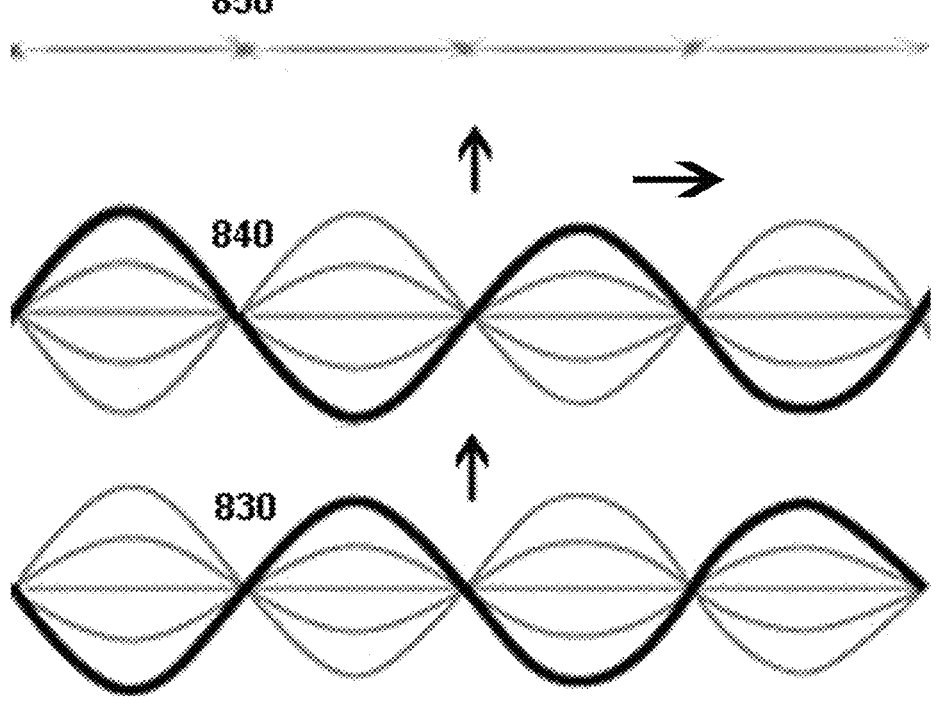

Number of sources: N=2

Peak Intensity = 4

Number of sources: N=100

Peak Intensity = 10,000

Source Geometry     950   3-D Intensity Map

100 Evenly Spaced Sources

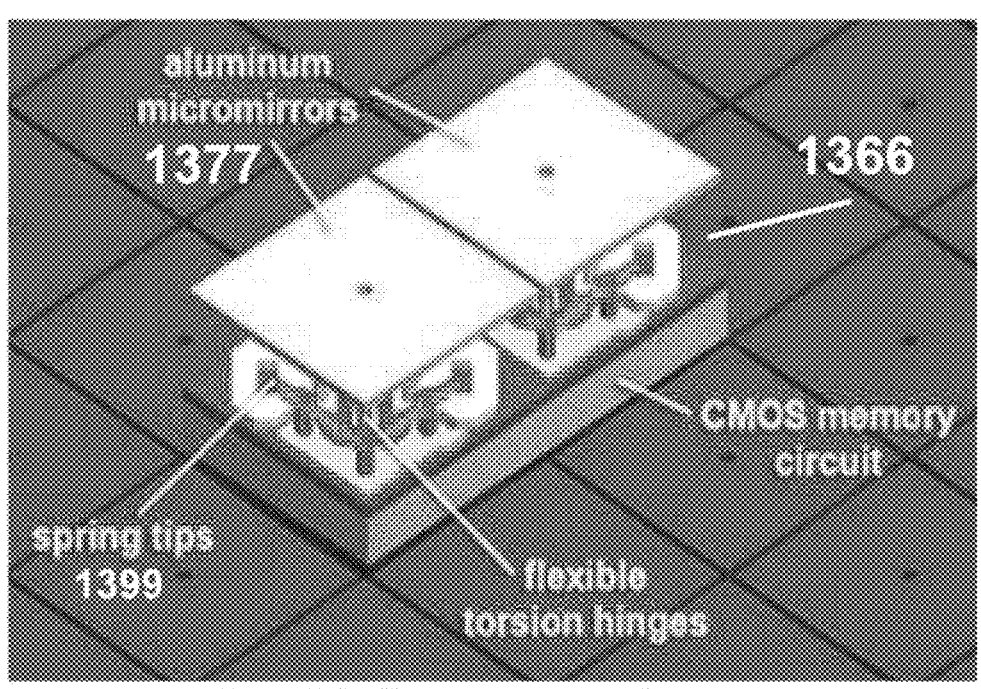
No Voltage to Mirrors
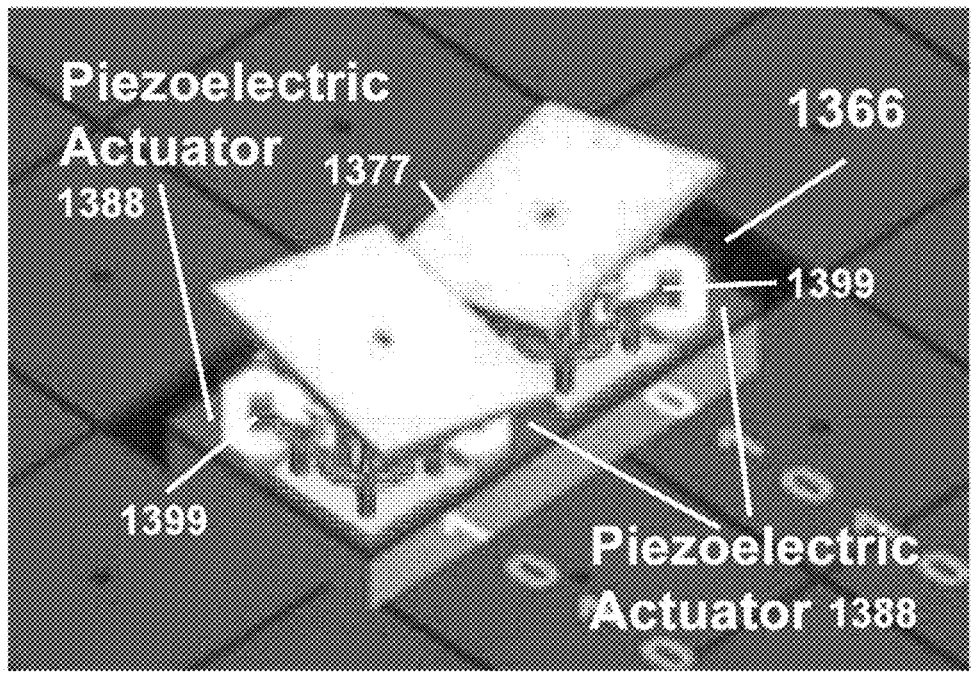
Voltage Sent to Mirrors
Fig. 13 B

HET Antenna System

HET Slave Antenna System

Receiving Antenna System

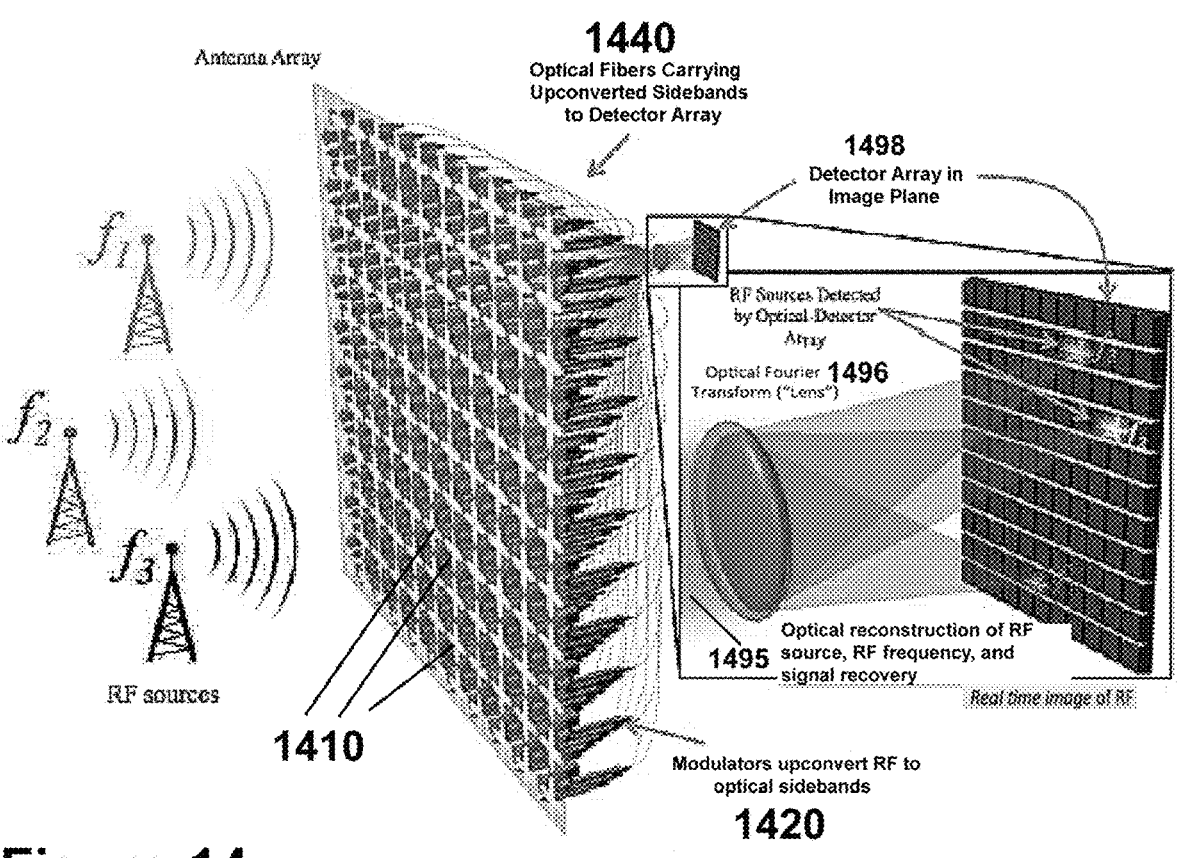

1440
Optical Fibers Carrying
Upconverted Sidebands
to Detector Array

1498
Detector Array in
Image Plane

Antenna Array

RF Sources Detected
by Optical Detector
Array

Optical Fourier 1496
Transform ("Lens")

1495 Optical reconstruction of RF
source, RF frequency, and
signal recovery

Real time image of RF

1410

Modulators upconvert RF to
optical sidebands
1420

RF sources

Figure 14

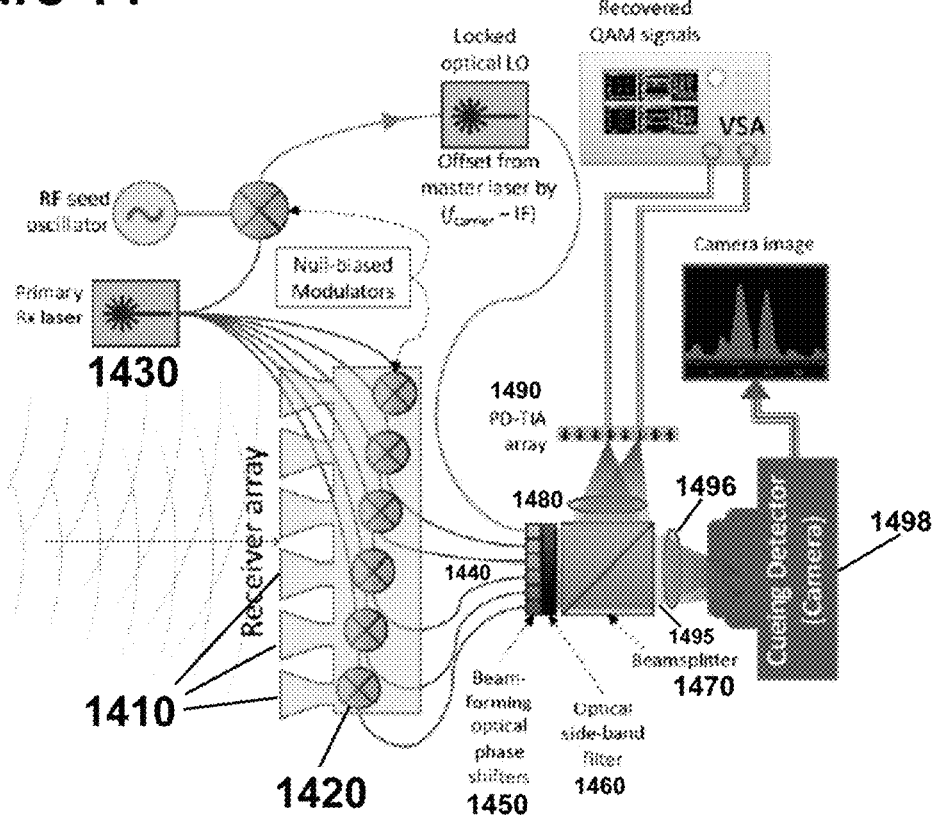

Locked
optical LO

Offset from
master laser by
$U_{carrier} \sim$ IF)

Recovered
QAM signals

VSA

RF seed
oscillator

Null-biased
Modulators

Camera image

Primary
Rx laser

1430

Receiver array

1490
PD-TIA
array

1480

1496

1498

1440

1495
Beamsplitter

1470

Beam-
forming
optical
phase
shifters
1450

Optical
side-band
filter
1460

1410

1420

PRECISE TARGETING OF BENEFICIAL EFFECTS OF COHERENT ENERGY USING NANOPARTICLES

CROSS-REFERENCE TO RELATED APPLICATIONS

The Application Data Sheet filed Jan. 18, 2025 identifies the antecedents of this application, the disclosures of which are hereby incorporated by reference.

TECHNICAL FIELD

This invention provides apparatus and methods for precision delivery of energy, for instance, to provide therapy to diseased bodily tissues, while minimizing interaction with surrounding structures.

BACKGROUND

There are many diseases and other medical conditions that physicians and scientists know a lot about and even understand very well, yet often they still aren't able to cure them. This is often because most diseases and other medical conditions take place within our bodies (rather than on or near the surface), making them generally inaccessible, especially when complex interaction is required, especially on a microscopic scale. In response to a problem in a specific location, such as a cancerous tumor somewhere, a clogged artery, plaques within the brain, an infection, a genetic disease, or even psychological conditions like depression and PTSD, physicians and scientists have devised agents and techniques that have been demonstrated to treat the problem within an experimental laboratory setting. However, translating such laboratory successes into routine clinically successful treatments is often a challenge. For instance, there are chemo, radiation, hyperthermia, genetic, drug, antibacterial, antiviral, antifungal, ablation, and neural stimulation therapies that can work well at the site of the problem for many conditions. The difficulty is in getting those therapies to the specific sites within the body where they are needed, without negatively affecting other cells within the body on the way.

The ability to move matter, even complex living matter such as a person, from one location (A) to another location (B), without the matter ever showing up in the intervening space between A and B, currently referred to as "teleportation," has been a staple of science fiction for centuries, and perhaps even millennia, when it was attributed to magic or supernatural powers. The "Transporter", as well as the "Food Replicator," and the "Holodeck" (first envisioned by the present inventor), as depicted on Star Trek, are based on this hypothetical invention.

Albert Einstein proposed that matter is just energy in a specific configuration ($E=mc^2$). Ever since this concept was confirmed by researchers at the Stanford Linear Accelerator Center in 1997 when they demonstrated that colliding high energy light beams (gamma-ray photons) would produce matter particles (electrons and positrons), it became understandable to the present inventor that the teleportation of energy would be the precursor to that of matter. However, so far, no one has disclosed a methodology, based on accepted science, that could accomplish matter or energy teleportation. Current research on "teleportation of information" or of "quantum states" is not the same as the teleportation of energy or matter.

As disclosed below, the treatment of diseases such as cancer and atherosclerosis, using energy teleportation, is a principal application of the inventions disclosed in this patent. However, the diagnosis, treatment or cure of a variety of diseases and medical conditions of humans and non-human living beings are within the scope of this disclosure and the claimed inventions, as well as many non-medical applications. Various types of energy waves can be used with the present invention including electromagnetic waves (such as light waves, radio waves, microwaves, X-ray waves, gamma ray waves) and sound waves. Such energy waves can be produced by any wave source including a laser, a maser, an ultrasonic transducer, an antenna, and an electromagnetic coil. The application of waves to specific cells within the body can be used to produce many effects such as vibration induction (for structural damage induction such as of stones or plaques), heating, ionization, ablation, scarring, apoptosis, necrosis, destruction, and stimulation or inhibition of gene expression, a chemical process, neural firing, release of hormones or other biological molecules, protein synthesis, blood flow, lymph flow, and mitosis.

SUMMARY OF THE INVENTION

By producing wave interference, such as holographically generated using Fourier synthesis, with superimposed standing waves that overlap with the proper time-phase relationship (called "Time-Correlated Standing-wave Interference" by the present inventor), wave energy is amplified (by "Coherent Intensity Amplification") and directed to precise locations, e.g. within a living body for such therapeutic applications as destroying cancer cells or plaques within arteries. A system implementing this technique creates amplified constructive interference at selected locations, while producing destructive interference at surrounding and/or intervening locations. This allows energy to be "teleported" to tumor cells, for instance, to detect and destroy them, while surrounding healthy cells receive virtually no energy, obviating collateral damage from the detection or treatment. Combinations of different waves can also be used to produce a combination of treatment-related effects. For instance, RF energy waves can be used to heat up a tumor and its attendant blood vessels. The heating of the tumor can produce some tumor damage, which then releases heat-shock proteins. These proteins then elicit an immune response which further damages the tumor. The heat can also dilate the blood vessels feeding the tumor, which increases the oxygen content in the tumor. When radiation therapy using X-ray waves is also administered to the tumor, the more oxygen there is, the more free radicals that are created when the X-rays strip off the outer electrons of oxygen atoms. The free radicals further degrade the tumor. Thus, the heightened oxygen content can make the radiation treatment much more effective. Use of the present invention can thus allow the administration of a combination of RF and X-ray waves to the tumor, without damaging healthy cells that normally would be irradiated in the entrance and exit paths of the wave radiation beams. Radiation intensity and duration can also be increased without increased healthy-cell damage. Consequently, radiation therapy combined with hyperthermia (increased heating) can be made more effective and safer. Alternatively to using radiation therapy, chemotherapy could be administered using chemotherapy agent molecules that are encapsulated in a protective, heat-labile coating. Administration of RF waves could dilate the tumor blood vessels, allowing more chemo to enter tumors than usual (improving effectiveness) while also dissolving the protective coatings, releasing the chemo agents in the tumor only, decreasing exposure of healthy cells to chemo agents, and thus reducing or eliminating side effects. As before, the heat-damage to the tumor can also elicit an immune response. Again, the use of the present invention can reduce or eliminate negative effects on healthy cells that could otherwise be created by the RF energy waves. Consequently, the combination of encapsulated chemotherapy agents with RF-induced heating (hyperthermia) of tumors and attendant blood vessels can increase the effectiveness and safety of chemotherapy.

Cancer and other diseases can sometimes be successfully treated with surgery. However, often, the situation is too intricate and complex for completely successful surgery to be possible without damaging healthy tissues. At some other times, various chemical-based methods, such as chemotherapy, immunotherapy, or genetic therapy can be successful. However, although chemical techniques can successfully treat cancers, atherosclerosis, and other diseases, as with surgery, very often, chemically-based treatments create significant damage to healthy tissues. At other times, energy-based therapy, such as radiation treatment or hyperthermia, can successfully treat cancer and other diseases. However, very often, energy-based treatments also create significant damage to healthy tissues. Often these techniques are used together in different combinations and can be successful, but still create significant damage to healthy tissues. To preserve a patient's quality of life, the extent of surgery and/or the strength of chemical- or energy-based therapies administered are reduced, often resulting in incomplete or less effective treatments or "cures," leading to disease recurrence and, ultimately, early patient mortality.

In accordance with the present invention, the successful treatment of disease within the body requires energy to be sent to selected cells and/or other molecules within the body, without adversely affecting other cells or molecules (such as healthy cells), to directly or indirectly destroy or alter the selected cells and/or molecules, and/or to initiate, modify, or terminate one or more processes affecting them.

Treatments using energy in accordance with the present invention may, for instance, include heating, ionization, or electromagnetic induction, thereby producing cell process disruption, apoptosis, necrosis, gene activation, deactivation, or alteration, neural excitation or inhibition, and/or chemical process initiation, activation, deactivation, cessation, release, clustering, and/or cleaving.

Current treatments of disease located within the body requiring the use of energy (such as X-ray or gamma-ray radiotherapy treatment, or hyperthermia treatment using the electromagnetic RF generation of heat within cells or within nanoparticles that heat cells) have an adverse effect on many healthy cells, reducing treatment usefulness. This is because the energy must pass through healthy cells on the way into and out of the selected regions to be treated, such as tumors, and must be intense enough to initiate the desired process once it reaches the selected regions to be treated. This is true whether the source is a broad energy emitter, a directed-energy beam, multiple directed beams, or a focusing phased-array emitter. Even though phased-array focusing uses constructive and destructive interference to concentrate energy at specific regions of space, they don't use destructive interference to generate regions of relatively energy-free space surrounding cells to be treated so that such regions contain no detectable or damaging energy. Such intentional employment of destructive interference is an essential feature of Holographic Energy Teleportation ("HET") disclosed herein. It provides a way that healthy surrounding and intervening cells can intentionally be spared exposure to unwanted energy. Furthermore, since energy transmission through the body is conventionally lost to absorption, scattering, and the generation of heat as it passes through healthy cells, such energy is intentionally made even more intense during conventional treatment when first sent into the body in order to compensate for such loss, producing increased potential adverse effects such as collateral damage of such healthy cells.

Collateral damage can often be severe enough to noticeably degrade the patient's quality of life, and can lead to significant permanent damage, even sometimes leading to patient mortality. In order to reduce such negative effects of current therapies, conventional treatments are typically reduced rather than maximized, which also reduces their effectiveness, often leading to recurrence of cancer or other disease.

To allow for fully effective cancer or other therapy using conventional treatment modalities, the surgery, chemicals, radiation, and/or hyperthermia should desirably be applied to the cancerous tumor cells (for instance) and not to intervening or surrounding healthy cells. If chemical therapy, radiation therapy, and/or hyperthermia are improved so as to be able to effectively kill all tumor cells, for instance, wherever they are, the need for surgery can be eliminated or reduced to the partial removal of tumors that are easily accessible and not entangled with healthy cells. In the case of radiation and hyperthermia therapies, safe, fully effective treatment requires energy to be applied to tumors, for instance, in a new way as taught herein. In these applications, this "new way" of applying energy to internal cells, while minimizing or eliminating effects on intervening and surrounding healthy cells, is referred to herein as "Holographic Energy Teleportation" (HET). The goal of this technique is to minimize energy's effect on healthy cells while maximizing energy received by target diseased cells.

It is important to understand what is meant by "teleportation" to understand the inventions disclosed herein. The concept of teleportation appears in some science fiction stories, TV shows, and movies such as Star Trek. But "teleportation" is not limited to fiction. In fact, it happens all the time in quantum physics, although we don't see it directly or refer to it as teleportation. Whenever we see light, it is because photons are emitted from electrons in atoms. Whenever a photon is emitted from an electron, the electron changes its orbital (its nucleus-orbiting radius) and begins orbiting the nucleus of the atom at a smaller radius (called a "lower energy level"). However, unlike a satellite orbiting Earth that can change its orbit to a lower orbit by moving in a continuous motion from the higher orbit down to the lower orbit, an electron can be said to "teleport" from one orbital to the other. It literally disappears from the orbit it's in and reappears in the new lower orbit without ever "passing through the space" between the orbits. This is commonly referred to as "quantum tunneling." The electron can be said to use "energy interference" to accomplish this seemingly magical feat. When it emits a photon, the electron goes "out of phase" with itself and disappears by "destructive interference" and reappears by going "in phase" in the lower orbit by "constructive interference." This fits the classical definition of teleportation, which is the passage of matter or energy from one location to another location, without appearing in or passing through the intervening space between the starting and ending locations. No one ever sees this happen with objects in our human-sized world, however. An example of this would be if you took a basketball and threw it at a concrete wall only to find that it kept going beyond the wall without making a hole. If the basketball disappeared when it got to the wall and then reappeared on the other side of the wall and kept on going, that would be a teleported basketball. However, this is hypothetically possible and may one day be commonplace.

In this patent, however, the present inventor discloses means to accomplish energy teleportation using HET by energy interference in our human-sized world. Since matter is made of energy, which has been demonstrated with the generation of electrons and positrons by the superposition of high-energy beams of electromagnetic ("EM") waves (i.e. gamma rays), energy teleportation could theoretically be used to generate matter teleportation (energy will be teleported and used to generate matter at its new location). However, matter teleportation is yet to be invented.

In accordance with the present invention, one way that HET is accomplished is by employing the unique capabilities of holography and Fourier synthesis in the proper way. Those that have experienced seeing a real hologram (rather than the optical illusions that are sometimes referred to as holograms, such as "Pepper's ghost") know that a hologram can re-create a fully three-dimensional image that appears in space, either behind or in front of the hologram (or both). This generation of a viewable image in space does not require a projector, a screen, smoke, water vapor, or a display of any kind (aside from the hologram itself). When illuminated by a simple light beam, the hologram creates waves that leave the hologram and travel in space, undergoing destructive interference in some places (where thus, no light appears), and constructive interference in other places (where light does appear). A hologram is a recording (usually on film) of an "interference pattern" (a pattern of bright and dark spots of light in space that result when two beams of light overlap and interfere with each other). The recorded interference pattern consists of extremely small dark and clear dots of different shapes, orientations, and sizes that alter the direction of light rays that pass through them, or reflect off of them, utilizing diffraction, refraction, and/or reflection. Because light rays illuminating a finished hologram are thereby bent (this is what the interference pattern recorded on a hologram does to light) into the same angles of travel that they were in when they previously reflected from a real object (that was located near the hologram), when the hologram was made, observers seeing those light rays coming from the hologram will think they are seeing that real object, even though the real object may no longer be there. The interference pattern is best created by the overlap of "coherent" light (extremely well-ordered, meaning of the same frequency, a high degree of parallelism, and with a uniform constant phase relationship), reflecting from a real object, and an additional coherent light beam, acting as a "reference beam" (which usually has no information about the real object). This interference pattern contains information about the angles of travel of all of the overlapping light rays coming from the object and from the reference beam. The two beams naturally interact to form an interference pattern where they overlap, and the recording of such an interference pattern at some location in space is called a hologram.

Since the mathematics of traveling and interfering light beams is known, the interference pattern that would result when such a hologram was recorded can, alternatively, be calculated in a computer and can be used to generate the hologram (in which case, it is referred to as a computer generated hologram). Such a computer-generated hologram ("CGH") can, consequently, "reconstruct" a three-dimensional image of an object that never actually existed, or one that existed but was not present when the hologram was made. The bottom line is, holography is used to guide waves of energy (such as light waves, RF waves, microwaves, X-rays, sound waves, or even gamma rays), so that they are traveling at any specific angles (and thus, phases) that one desires, and those waves will overlap in space, producing destructive and constructive interference in different locations in space, creating the appearance of an image.

Moreover, the image generated by a hologram doesn't have to be an image of an object. In accordance with the present invention, the image could, instead, be the image of one or more isolated points of light (or other energy) at one or more specific three-dimensional locations in space, surrounded by "blackness" (no apparent energy). Normally, a conventional hologram produces points of light in space by focusing or directing light rays to overlap each other at desired specific points in space where an image is to appear (just as a lens does). In that case, there is also detectable light in space at locations other than where the points of light are desired to be visible (at the focus), only at a lower level. However, according to the present invention, a holographic system is made to produce points of light (or other energy) in space by interacting with the light (or other energy) that hits the hologram in a unique way. This interaction changes the angles (and thus, phases) of the light (or other) waves so that they overlap in space creating destructive interference everywhere within a defined space, except at the location (or locations) where the point or points of energy are desired. This point or points of energy becomes visible by constructive interference. This is not what holograms are made to do conventionally. In the present invention, the regions in space where destructive interference is made to occur is filled with electromagnetic waves, but because they overlap out of phase with each other, creating destructive interference, that energy is not detectable and produces no effect in that region of space (and don't get absorbed or otherwise interact with matter within that space). Energy is visible only at the point or points where constructive interference occurs. With this method, a point or points of light (or other energy) is produced in defined regions of space, surrounded by no detectable energy within a larger defined region of space. This unconventional unique method of holographic "image formation" is the basis of a method to accomplish HET. Hence, HET is a unique new method to place energy anywhere in a defined space, with no noticeable energy in the space surrounding the defined space, such as in the space before and after the defined area of space that is to contain the energy, along the line of energy travel into and out of the defined energy-containing space.

When two ordinary beams of light overlap, they produce a spot which is as bright as the sum of the two beams added together. This is essentially what happens all the time, especially when the beams are in phase and constructive interference occurs (which produces even more energy, as will be explained herein below). However, few people can imagine, or have ever experienced, two beams of light overlapping and producing a dark spot. Amazingly, this is what happens when the two beams are out of phase and they undergo destructive interference. The reason people don't normally experience this is that most light sources don't produce coherent radiation, and wherever such destructive interference happens with incoherent light, some other stray light beam from some other angle comes along and fills in the dark spot so no one notices it. However, when the phases and angles of available energy are carefully controlled (such as with coherent light from a laser), this normally-unexperienced, counterintuitive phenomenon becomes perceptible.

One place where destructive interference happens in everyday life is within a microwave oven. The microwaves are carefully controlled and overlap, creating "standing waves," which produce different regions of constructive and destructive interference within the microwave oven. Food sitting in a region of destructive interference (called a "node") doesn't get heated by the microwaves because destructive interference causes that region of the food to experience no RF energy, even though powerful microwaves are passing through that region of the food the entire time of cooking. This is why microwave ovens typically include a rotating table (and/or a rotating beam director) to move different regions of the food out of regions of destructive interference and into regions of constructive interference for more uniform heating. As another example, most people have experienced "dead spots" in their home or car when using a wireless smartphone, tablet, or radio. These dead spots are often regions in space of destructive interference as well. The energy is there, since the energy passes through the dead spots, only to be detectable again at a different location, but destructive interference makes the energy undetectable at the "dead" locations. This principle is also used in noise cancelling headphones. The undesired noise is detected and generated a second time, but out of phase with the original noise, creating destructive interference and making the noise "disappear." By adding the additional noise (out of phase), the unwanted noise is cancelled. All of these known distributions of constructive and destructive interference are periodically interspersed rather than consisting of one or more defined points of constructive interference surrounded by larger regions of destructive interference. However, the present invention uses constructive and destructive interference in a completely new way.

The present inventor discloses herein how energy is sent into a region of space, such as that occupied by a body, and appear only at desired points, such as where tumors or plaques are located, while surrounding healthy cells experience little or no energy. To tell the computer how to create an interference pattern that redirects the light (or other energy) to create constructive interference only at a location we want, while creating destructive interference at other surrounding locations, we can look at the energy distribution in space that we want to produce as if it was a "complex wave" (as distinguished from a simple sine wave). The mathematics to calculate the details of the various electromagnetic (or other) waves that have to be produced to generate this complex wave in space employs "Fourier analysis" and "Fourier synthesis." Fourier analysis allows any complex wave to be described by a series of sine waves (a Fourier series). Superimposing the elements of this Fourier series of sine waves will reconstruct the original complex wave by Fourier synthesis. Thus, this technique is used to create the desired distribution of energy in space, containing areas of constructive interference surrounded by areas of destructive interference.

A computer is employed to calculate the Fourier series of sine waves needed to produce a desired complex wave (representing an existing or an imagined energy distribution), and if those sine waves are added back together they will produce that same complex wave, even if the complex wave was initially just imagined and never physically existed before. With that data, a computer can generate the data for a holographic interference pattern (a computer generated hologram) that will define the sine waves that are required to be added together to produce any complex wave pattern of energy in space. Such a computer-generated hologram ("CGH"), when properly illuminated, can alter and redirect the illumination to provide the aforementioned sine waves of any amplitude, frequency, or phase required, as dictated by the Fourier analysis calculation, and they can be sent in any directions required (by holographic reconstruction from a hologram), to produce the final desired complex wave energy pattern in space. Combining the capabilities of holography with Fourier synthesis, therefore, allows us to generate any complex wave we wish in three-dimensional space. Consequently, if we select a region of space and determine that we want wave energy to appear at only one specific location within that space, for instance, a properly programmed computer, as more specifically taught herein, will calculate the necessary Fourier series and generate data for a hologram that will superimpose sine waves of energy, such as radio frequency ("RF") waves, in that space (when energy emanates from that hologram), producing energy only in the region of space we have designated (by constructive interference), while all other adjacent or surrounding regions in space will appear to be devoid of energy (due to destructive interference). The space filled with constructive interference can be a selected volume within a human body which contains a tumor, for instance, and the hologram, thus, sends high intensity RF waves, for instance, directly into the tumor, causing heating of the tumor, while all surrounding healthy cells experience (i.e. are affected by) little or no energy at all. This method is distinctly different from previously used phased-array focusing of EM waves, for instance, since the EM waves generated during phased-array focusing are still detectable by, and cause the heating of, healthy cells on their way into and out of the tumor regions.

Various equipment configurations can be used to accomplish HET, examples of which are disclosed herein, to holographically generate the needed interfering waves to deliver the required energy only to diseased regions within the body for therapeutic treatment. In effect, this technique works by "muting" the energy (by destructive interference) as it is transported through healthy cells, and "unmuting" the energy (by constructive interference) once it reaches its intended destination (thus, "teleporting" it). In conventional treatments, energy is "unmuted" as it passes through healthy cells, and the energy is therefore directly detectable by (and potentially damaging to) the healthy cells.

Teleporting is known in science fiction and is generally believed to be a hypothetical method to transport something existing at a starting location to a destination location, without it ever appearing to pass through or exist in the space between the starting and destination locations. In the case of HET as disclosed herein, the "something" being teleported is energy. It isn't detectable in the space between the starting and destination locations because it is "muted" while in that space. Muted energy is virtually undetectable and produces essentially no negative effects on cells or anything else. Such teleported energy (as produced by HET) can treat disease directly (such as by the use of ionizing X-rays or the electromagnetic hyperthermic generation of heat within cells), and/or can initiate or prevent a process from occurring, such as the firing of neurons or the synthesis or release of proteins, hormones, enzymes, or other biological substances.

BRIEF DESCRIPTION OF THE DRAWINGS

FIG. 5D is a table labeled Table 1, which lists parameters used in describing some examples of the present invention.

FIG. 8A is a diagram depicting standing waves with nodes and anti-nodes used in describing some examples of the present invention FIG. 8B is a diagram further illustrating standing waves to help with an understanding of a principle used in an embodiment of the present invention.

FIG. 14 is a diagram illustrating a receiving HET antenna system that may be used to detect coherent radio waves for use in accordance with the present invention.

DETAILED DESCRIPTION

Referring to the accompanying drawings for illustration, HET muting of applied energy is accomplished by applying out-of-phase additional energy to the energy normally used to provide treatment, thereby cancelling out the initial energy by destructive interference in the regions of healthy cells, while not cancelling out the energy in the selected treatment regions. This allows the energy to have a therapeutic effect in the selected treatment regions only (such as in tumor cells). During destructive interference, shown in FIG. 1B, waves cancel each other out (just as in audio noise cancellation, for instance), and they have virtually no effect on anything. Cells cannot experience (be affected by), and are not altered by, waves that are in a state of destructive interference. However, being canceled out doesn't mean that the energy waves are destroyed or dissipated; rather they are just muted. They still propagate together through space.

Figures 1A, 1B:
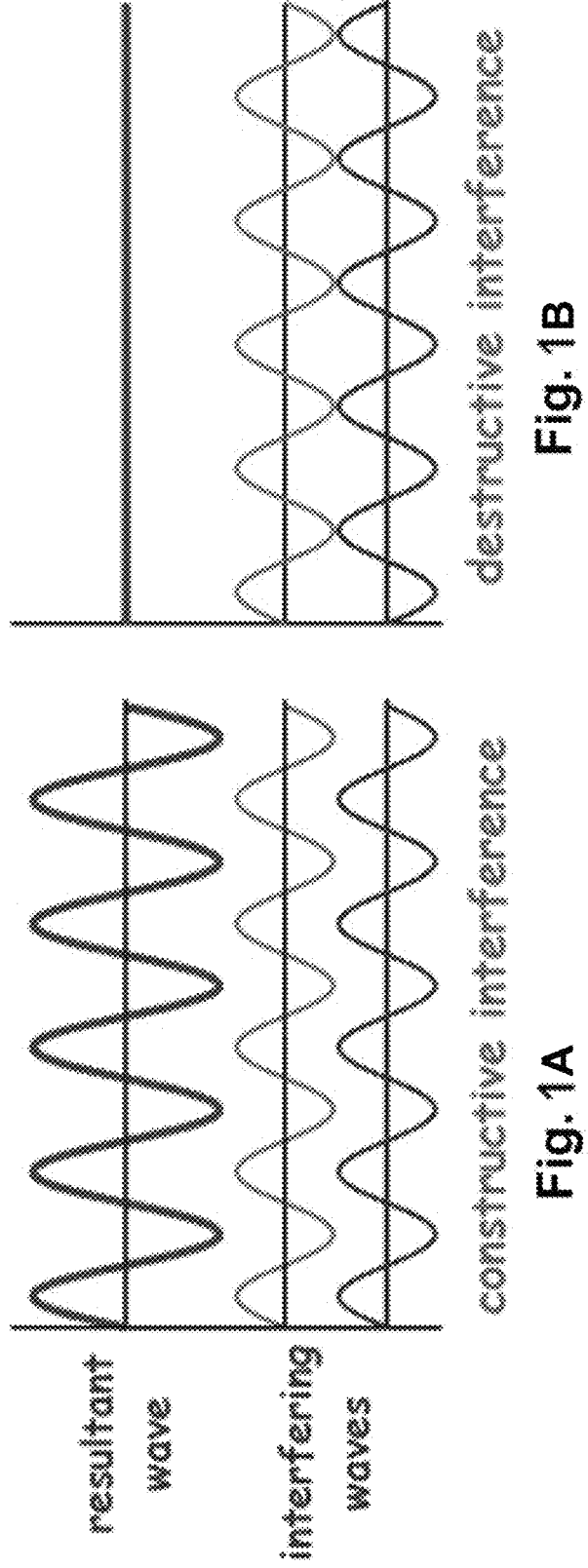
FIG. 1A is a depiction of constructive interference referred to in the description of the present invention.
FIG. 1B is a depiction of destructive interference referred to in the description of the present invention.

Unmuting is accomplished by causing the energy waves to go into phase and undergo constructive interference in the targeted cells. When two mutually coherent waves interfere constructively, as shown in FIG. 1A, they add their energies together, producing a maximum effect in the regions where they are in-phase of up to four times the intensity of either one of the initial energy waves. Essentially, the energy that would have appeared in the areas of destructive interference, if there was no destructive interference, is shifted to the area of constructive interference. In accordance with the present invention, the creation of destructive and constructive interference in the desired regions of three-dimensional space occupied by a patient can utilize holography and optical Fourier synthesis in a new way (collectively referred to herein as HET). Fourier analysis can be used to calculate required sine wave parameters within a computer to determine the directions, phases, frequencies, and amplitudes of energy waves required to produce destructive and constructive interference at desired locations in three-dimensional space. This information can be used to define a computer generated hologram ("CGH"). Use of the CGH can provide a way to direct energy waves in desired directions with desired amplitudes and phase relationships to produce desired patterns of energy in space by optical Fourier synthesis.

This new method allows energy to be emitted from one or more initial locations (such as outside of the body) and sent to one or more selected destination locations (such as inside the body) without being detectable in the intervening or surrounding space between the initial and destination locations, or beyond the destination locations (thus, the energy is teleported). Such use of teleportation of energy for the diagnosis or treatment of disease has never been done before.

In the case of radiation therapy, in accordance with the present invention, although ionizing radiation (such as high-energy X-rays or gamma rays) are traveling through healthy cells in order to get to (and subsequently, away from) target cells, they are muted by HET and thus produce virtually no ionization or heating, and thus no damage to healthy cells. Once they arrive at the target diseased cells, however, they are unmuted and can do maximum damage, especially since their intensity doesn't need to be reduced initially, as it does in conventional treatment. The same is true for hyperthermia treatment, wherein RF energy is sent into the body to heat up cells directly, and/or optionally, to activate and deactivate chemical reactions at target cells. Muted RF energy also has virtually no effect on healthy cells while having a maximum effect on their targets where it is unmuted.

The trademark Holothermia™ identifies services or goods employing a process in accordance with the present disclosure as provided or licensed by Holobeam Technologies Inc. Such a process involves the use of Holographic Energy Teleportation (HET) with a cell- or molecule-altering process such as hyperthermia, with or without nanoparticles, for the treatment of disease. A Holothermia™ device delivers energy to specific selected internal structures within a body at almost any size, with pinpoint accuracy (limited to the wavelength of energy used), for heat-activated treatment of disease without the collateral damage of current hyperthermia methods. If it is used with ionizing radiation such as x-rays or gamma rays, it can dramatically reduce or even eliminate collateral damage currently produced by conventional radiotherapy. Moreover, the use of HET with RF waves has the potential to produce the same damage to tumors as ionizing radiation, without the drawbacks of using conventional radiotherapy, such as large, expensive, complex equipment, special training, various radiation hazard risks, and collateral damage to healthy cells.

Figure 2:
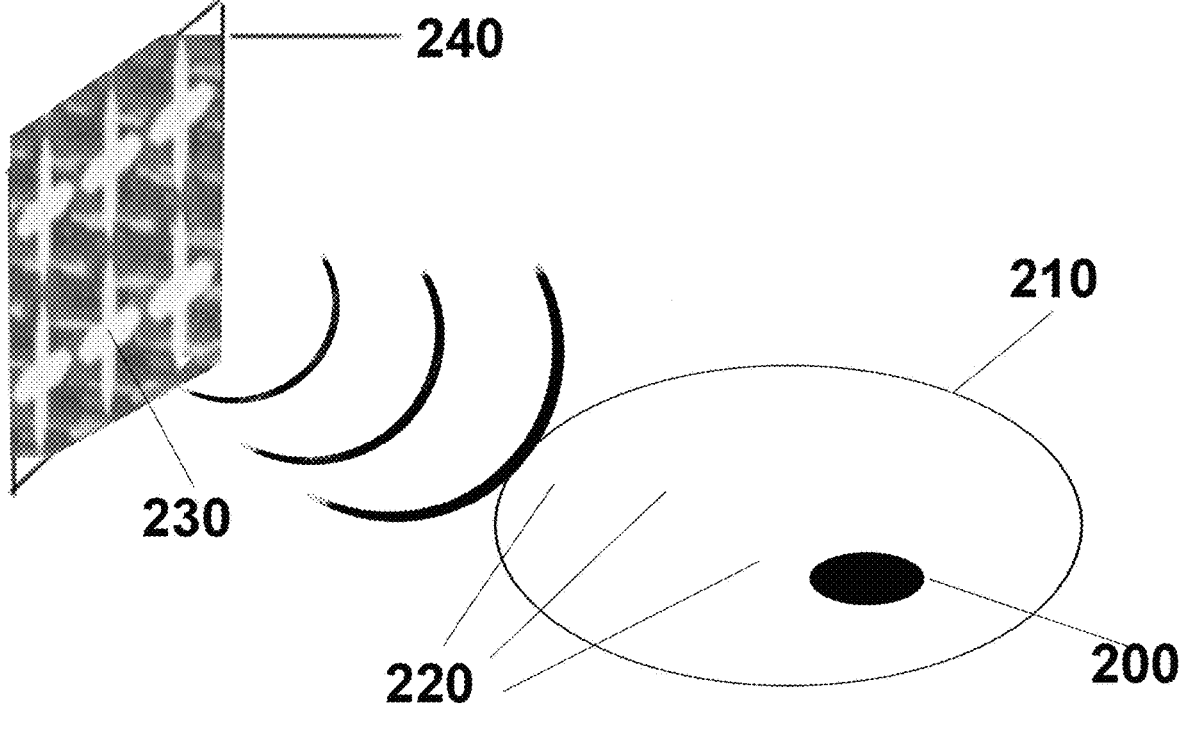
FIG. 2 is a diagram depicting one of the problems with the prior art.

FIG. 2 illustrates the challenge of sending energy from an energy source, such as an array of antennas 230 (with a mounting structure 240) located outside of the body 210 to a designated region 200 within the body 210. Energy (in the form of travelling waves) irradiates healthy cells 220 on its way to the designated region 200, creating collateral damage and other unwanted side effects. This arrangement is what is done currently and is prior art.

To minimize or eliminate negative effects on healthy cells from the passage of this energy, a new technology, designated as Holographic Energy Teleportation (HET), is disclosed herein. This technology involves a novel application of holography and Fourier synthesis that, for the first time, teleports energy from one or more "origination" locations (such as an energy source 230 outside of the body 210) to one or more "destination" locations (such as at one or more locations 200 within a body). However, means for implementing this new invention is not depicted here in FIG. 2. The nature of the teleportation is that, although the amount of energy sent from the one or more origination locations 230, and the amount of energy received at the one or more destination locations 200 may be high, the amount of detectable energy in the places 220 between the one or more origination locations 230 and the one or more destination locations 200, and the area beyond the locations 200 is very low or zero. The energy teleportation is accomplished, for instance, utilizing Fourier synthesis and holography in a new way, which can be understood from the following analysis and description.

Figure 3A:
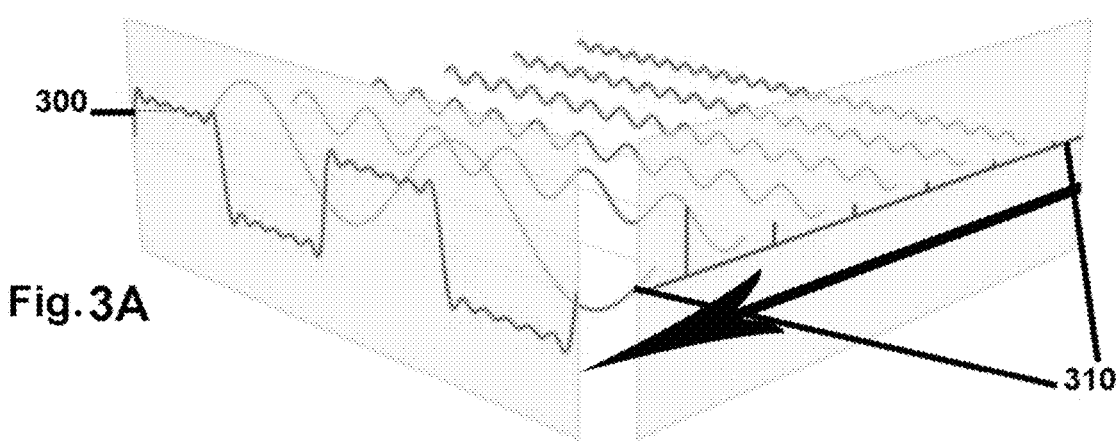
FIG. 3A is a diagram depicting waves that illustrate Fourier analysis and Fourier synthesis referred to in the description of the present invention.

In 1822, mathematician Joseph Fourier showed that any complex wave can be broken down mathematically (in a process called "Fourier analysis") into a series of many simple sine waves (called a "Fourier series") that differ from each other only in their amplitudes (strengths), frequencies (how fast they oscillate, temporal or spatial frequency)), and phases (the relative positional relationship of one sine wave to another). If the many waves from that calculated series of sine waves are superimposed on each other, they will once again add up to the original complex wave (a process called "Fourier synthesis"). This can be seen, for example, in FIG. 3A in which 300 is an original complex wave and 310 represents the various different sine waves (the "Fourier series") resulting from the Fourier analysis of the original complex wave 300. When these sine waves are added together by superimposing them on one another, referred to as Fourier synthesis, constructive and destructive interference from the algebraic summation of the waves will result, producing the original complex wave 300 again.

Figure 3B:
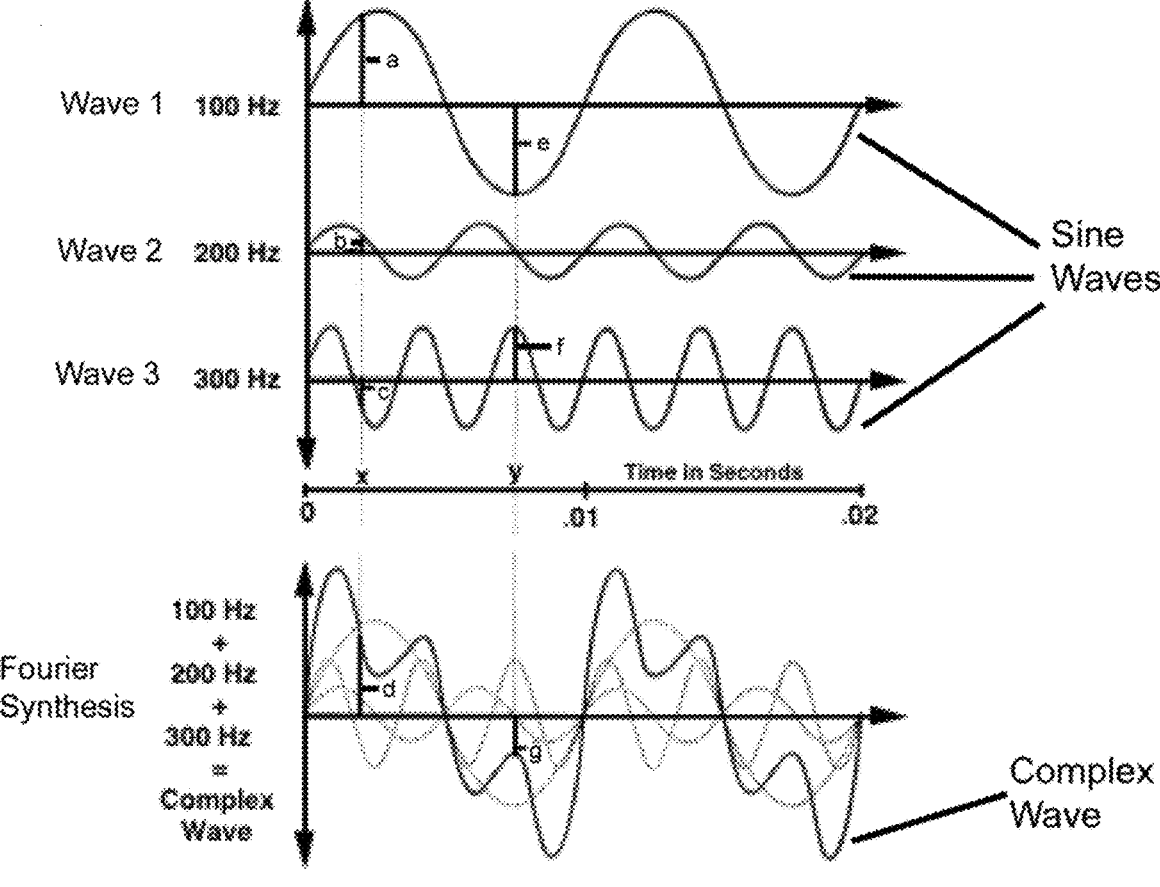
FIG. 3B is a diagram showing how individual sine waves can be added together to produce a complex wave with Fourier synthesis.
Figure 3C:
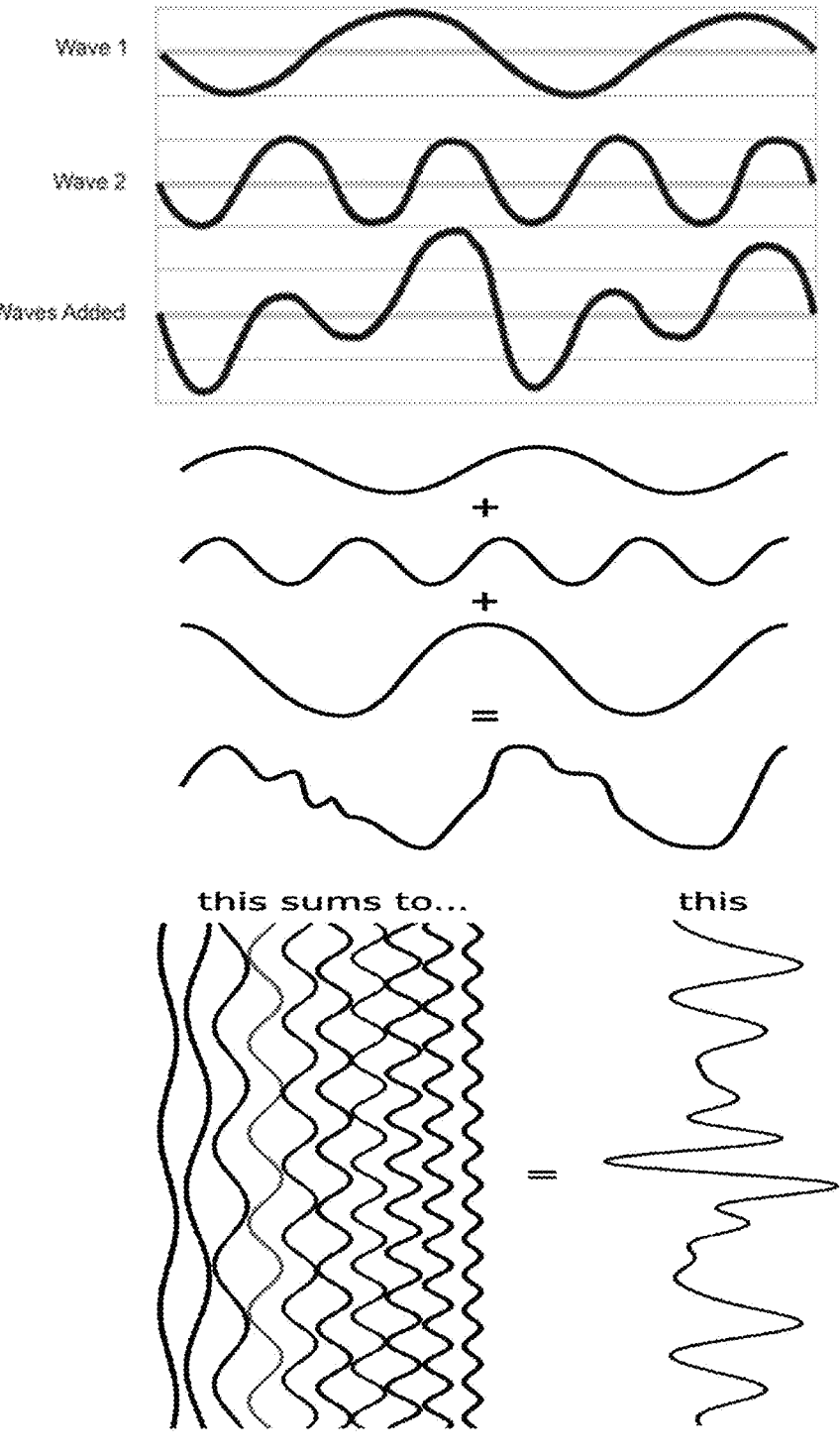
FIG. 3C is a diagram showing further examples of sine waves adding up to form a complex wave with Fourier synthesis.

FIG. 3B depicts how various sine waves add together algebraically during Fourier synthesis. Three different sine waves, labeled Wave 1, Wave 2, and Wave 3 are shown separately in the top half of the figure. In the bottom half of the figure, Fourier synthesis of the three waves is shown, also dimly showing all three superimposed sine waves along with the resulting complex wave depicted with a darker line. As an example, the addition of the amplitude values of the three sine waves (at "a", "b", and "c") at time "x" are shown in the top half of the figure, and their algebraic sum "d" is shown in the bottom half of the figure. Note that "a" and "b" are positive values, while "c" is a negative value, resulting in the positive algebraic sum at "d". As another example, the amplitude values ("e" and "f") of the waves are shown at time "y". Note that "e" is negative and "f" is positive, while the value at time "y" for Wave 2 is zero. The algebraic sum of these values is negative and is depicted at "g". In a similar fashion, the amplitudes of all of the sine waves at every point in time are added together algebraically, resulting in the Fourier synthesis of the final complex wave. The resulting complex wave shown in the bottom half of the figure is the Fourier synthesis of Wave 1, Wave 2, and Wave 3 shown in the top half of the figure. When waves add together where they are both positive (wherein both are above the center line) or where they are both negative (both below the center line), they add constructively, creating what is called constructive interference. When waves add together where one is above the line (positive) and the other is below the line (negative), they subtract from each other destructively, creating what is called destructive interference. This is what is meant by algebraic addition. FIG. 3C shows examples of 2, 3, and 10 sine waves adding up by Fourier Synthesis to form complex waves.

An image of anything can be broken down, for instance, into a sequence of slices, or lines, such as the scan lines used in conventional television. The brightness values along each of these lines can then be represented as a complex curve. Each complex curve can then be broken down by Fourier analysis calculations into a set of sine waves. The sine waves in each set can then be superimposed on each other to re-form an image of each slice by Fourier synthesis. Assembling the Fourier synthesized images of the various slices would then result in the reformation of the original image.

Many unique applications of this technique can be used to form images unobtainable in other ways. The present inventor treats the desired energy distribution needed to treat disease within the body, while bypassing healthy cells, as a complex wave of energy to be formed within a patient's body, and has developed ways to construct such complex waves, for instance, by using Fourier synthesis.

Figures 4A, 4B, 4C, 4D:
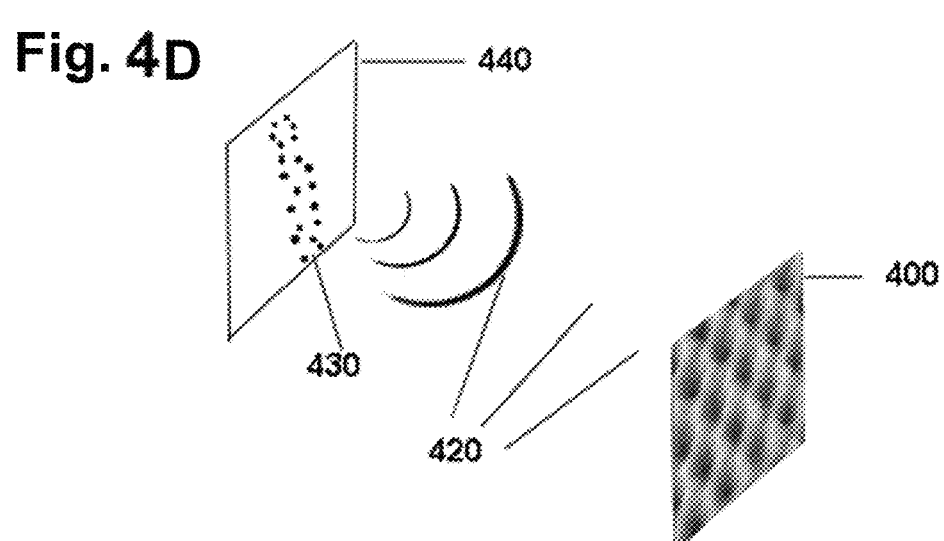
FIG. 4A is a diagram depicting an x-ray beam illuminating a crystal which produces an x-ray diffraction pattern that is recorded on a recording material such as photographic film.
FIG. 4B is a diagram depicting three linear bar patterns with different spacings.
FIG. 4C is a diagram depicting Thomas Young's double-slit experiment where the fringes produced are recorded on a photographic plate.
FIG. 4D is a diagram depicting the arrangement used by Bragg to reconstruct the atomic structure of a crystal with data from a diffraction pattern.

In 1929, Sir Lawrence Bragg developed an "X-ray microscope" utilizing this principle with X-rays and light waves (which are sinusoidal by nature), to produce an image of the atomic structure in the crystal diopside. In 1948, Dennis Gabor utilized the concepts of Bragg's X-ray microscope to invent holography for the purpose of producing a new type of electron microscope. Bragg correctly theorized that the layout of the atoms in the crystal could be used to diffract X-rays, forming a diffraction pattern which would allow him to calculate the necessary sets of sine waves by Fourier analysis. As depicted in FIG. 4A, shooting X-rays through the crystal at the proper angle (based on crystal symmetry) provided X-ray diffraction data that allowed him to determine the amplitudes, phases, frequencies, and orientations of the required Fourier components (sets of sinusoidal waves). When waves are diffracted, the resulting diffraction pattern becomes an image of a Fourier series. He theorized that the optical superposition, using visible light, of the sinusoidal patterns (referred to as "optical Fourier synthesis"), based on the detected diffracted Fourier series produced at the X-ray wavelength, would produce a magnified image of the crystal structure. He also realized that magnification would result automatically from the fact that the initial diffraction is done at an X-ray wavelength, whereas the Fourier synthesis is done at a visible light wavelength. The difference in the size of X-ray and light wavelengths becomes the magnification factor.

Initially, to accomplish production of the sine wave images, Bragg took 40 photographs of opaque cylindrical rods, with their axes parallel, spaced apart by a distance equal to twice their diameters. The size of, and spacing between cylinders, as well as the placement and orientation of the cylinders in each photo was based on the sinusoidal-wave data obtained from the Fourier analysis of the diopside crystal diffraction pattern. Each image was sequentially projected, slightly out of focus, onto the same single sheet of photographic paper. Each slightly out-of-focus image looked like a sinusoidal wave pattern. Three such images are depicted in FIG. 4B, which clearly have different spatial frequencies (even though they all have the same temporal frequencies). The developed final picture provided an image of the atomic structure in the crystal, as he had hoped, but with low-contrast. To improve the image quality, he then, instead, produced the sinusoidal wave patterns using the 1801 Thomas Young two-slit arrangement depicted in FIG. 4C. Light from a single pinhole (not shown), used to produce spatial coherence, illuminated a pair of pinholes (A and B), creating light waves that overlapped each other, forming an interference pattern on the photographic plate.

The interference pattern consisted of dark lines appearing at C, D, E, and F, and bright lines appearing on either side of the dark lines. Utilizing light of a narrow frequency band (such as yellow sodium light) and/or color filters, increased the temporal coherence (monochromaticity) of the light used. By utilizing 40 such pairs of small holes drilled into an opaque plate, with each pair producing another set of sinusoidal waves on the final picture, each producing a sinusoidal pattern with its own spatial frequency, he produced a Fourier synthesized image with better contrast. The sizes of the holes drilled in the opaque plate were varied to correspond to the desired amplitude of each set of waves, and the positions, orientation, and displacement of each pair of holes with respect to each other were selected to correspond to each wave pattern's required placement, orientation, and frequency. This experiment showed the validity of using optical Fourier synthesis to produce an image simply by superimposing sinusoidally varying patterns of light corresponding to calculated sine waves derived from the Fourier analysis of a complex wave. By using light that originally came from a single pinhole to illuminate the various sets of pinholes, and color filtering the light, each of the involved light beams was approximately coherent with each of the other beams (both spatially and temporally), while the different sets of sinusoidal patterns produced were spatially different from each other. Coherent superposition of waves produces maximum contrast, regardless of how many beams overlap, since light doesn't fill in dark regions randomly as it would with completely incoherent light, but instead creates an interference pattern resulting from the algebraic sum of all waves, even though many waves are superimposed.

The setup to carry out Bragg's Fourier synthesis with pinholes is depicted in FIG. 4D. Element 400 is the photographic sheet containing the final image made from the overlap of sinusoidal waves (which would correspond to the destination location 200 within a body 210, if this technique were to be used to send energy to a specific location within a body). Plate 440 contains the pairs of holes 430 (which would correspond to the structure 240 and the energy source 230). Of importance is the space 420 between the plate 440 containing the holes 430 and the sheet 400 containing the final image. This space 420 (which would correspond to the healthy cells 220) contains energy in the form of traveling waves, making this arrangement undesirable for sending energy from a source 230 (corresponding to the holes 430 in plate 440) into a location 200 (corresponding to sheet 400) within a body since all intervening healthy cells 220 (corresponding to space 420) would be irradiated by this traveling-wave energy as well, which is detectable and can cause undesired effects, such as heating. This is because traveling waves don't allow for the production of easily defined, unchanging standing wave patterns of constructive and destructive interference over large volumetric areas of space. It is important to note that, although the waves originating from the source 430 and propagating to the destination 400 are traveling waves, the interference produced at sheet 400 is a superimposed series of waves that do not change over time, forming a standing wave pattern in plane 400. This allows them to appear stationary and be recorded on a sheet 400 of film. However, the traveling wave pattern occurring in the space 420 is not stationary and definable, as the waves there are traveling waves and don't add up to a standing wave pattern. Thus the space 420 does not contain just destructive interference.

Referring back to FIG. 2, to accomplish the irradiation of the destination location(s) 200 within a body 210 without energy irradiating the healthy cells 220, what is needed is a method to "cancel" or mute the energy located at regions 220 while the intended destination 200 receives unmuted energy. In accordance with the present invention, this can be accomplished by producing a standing wave pattern of destructive interference located in the region 220. As noted herein above, energy "cancelled" by destructive interference is not absorbed, scattered, reflected, or destroyed; just made undetectable and ineffective due to the counter-effect of the simultaneously superimposed out-of-phase energy in the same location. Such a method must also be capable of allowing the energy waves to go back into phase, creating constructive interference, but only at the destination location(s) 200, to be able to produce their desired effect. Consequently, Bragg's X-ray microscope design, even though it produces stationary destructive interference at designated areas in the plane of sheet 400, can't be used successfully to reconstruct energy at one or more destination locations within the body 200 without irradiating healthy cells 220.

The present inventor has discovered means to accomplish destructive interference at non-target regions 220. The present invention can utilize Fourier synthesis in a different way than has been conventionally done. Stationary-wave Fourier synthesis involves the superposition of sine waves, forming standing waves that don't change over time and/or space. In Bragg's X-ray microscope, each pair of holes produces a stationary sine wave pattern only on the final photographic sheet. However, the light from the multiple holes propagates as traveling waves to the final image in a direction perpendicular to the plane of the standing waves which form the final image. The final image plane is where the constant-pattern Fourier synthesis, and thus, fixed constructive and destructive interference pattern, takes place as needed to create the final image. The light that travels from the holes to the final image consists of traveling sine waves that, due to their constant changing superposition, couldn't be used to generate a specific stationary pattern of overlapping sine waves resulting in only destructive interference in the space they are traveling through on their way to the final image plane. Therefore, that energy would always be detectable as it travels to the final image plane and would not produce the results intended for the present invention.

Bragg's X-ray microscope was essentially based on a one-dimensional Fourier transform using wave sources located in a single plane which formed an image in another plane (referred to as the inverse transform plane). The traveling waves propagated from one plane to the other, while always being detectable as changing, traveling waves in the space between the planes. The final desired interference pattern was produced in a plane that was roughly parallel to the energy source plane, while the traveling wave plane was perpendicular to both the energy source and image planes.

In accordance with the present invention, one embodiment that can produce a desired strong energy wave field in one or more selected regions of space (where tumor cells are located, for instance), while destructively interfering with (canceling) the waves in the surrounding regions of space (where healthy cells would exist) uses the arrangement of locating the energy emitters in a circle around the selected region, allowing waves to overlap each other such that each wave is overlapped by waves coming from other directions, resulting in destructive interference in all regions of space except for a selected region or regions within the circle, where constructive interference is desired.

In 1998, Okuyama et al. were studying the behavior of "rogue waves," a somewhat rare, freakish, naturally occurring ocean wave that can reach 100 feet tall, which unexpectedly rises out of a calm ocean and sinks giant ships and threatens oil rig platforms. His analysis included the use of Fourier synthesis to generate discrete raised water waves or discrete water spikes that rise out of otherwise-calm water in specific locations of his choosing. To illustrate this process in an easily demonstrable way, he used a circular arrangement of water wave generators to produce raised American alphabet letters on the surface of water.

Figure 5A:
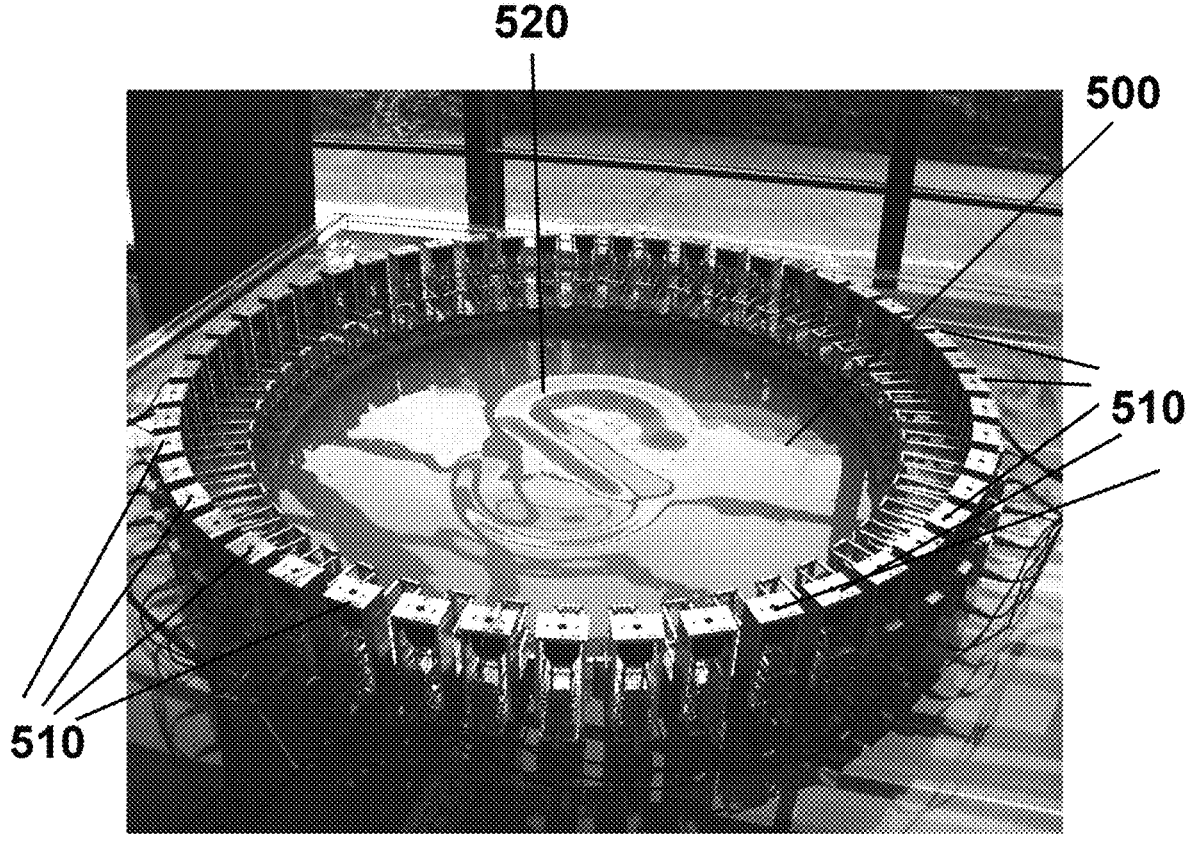
FIG. 5A depicts an experiment using a water tank and acoustic waves that demonstrate a principle uniquely employed in some examples of the present invention.

This is illustrated in FIG. 5A. A circular tank 500, 5 feet in diameter, was filled with water. Around the periphery of the tank were located 50 electrically activated solenoid wave makers 510, each with the ability to generate physical water waves. Using a computer to control the strength, speed, and timing of each solenoid, he was able to generate a wave structure, utilizing Fourier synthesis, having a desired shape on the surface of the water within a 4 foot diameter circle in the center of the tank, while producing flat, calm water everywhere else around the generated letter.

As shown in FIG. 5A, the water is raised up about 5 cm to form the letter "S" 520 in the center. The rest of the water in the tank is flat and smooth, as can be seen by the reflection of a nearby window, indicating that no energy appears to be present anywhere on the surface of the water except where the letter "S" appears at 520. Because this method uses traveling waves with different temporal frequencies to produce the Fourier synthesis, however, a bias is produced, meaning that, although the water is flat everywhere outside of the generated "S", the water level is raised up everywhere (over time), and is not at zero (devoid of energy). He confirmed that the use of more powerful and/or a larger number of solenoid wave makers would produce even higher letters on the surface of the water. However, the bias would increase as well in the non-letter areas. Since the different waves have different frequencies, it takes some time for them to overlap each other with just the desired phase relationship to form the desired constructive interference pattern, forming the desired letter on the water's surface. At other times the water heights have small random values, resulting in the bias over time, until the waves all come back into the desired phase relationship once again. This reduces the height difference that can be produced between the raised area and the flat areas.

Using a variation of this approach would represent a major advantage over currently-used methods of therapeutic patient irradiation, increasing the energy level difference between target regions and intervening regions. The present inventor realized that, instead of the solenoids placed around the periphery of the water tank to produce water waves, using sources of RF, microwave, X-ray, acoustic waves, or even gamma radiation placed in a circle, surrounding a patient, could provide a method for energy to be sent to specific locations within a patient to treat disease, while minimizing collateral damage. However, to implement that requires a completely new system with new hardware and procedures, plus a major change in the theory to allow for efficient and successful implementation.

To analyze such a circular energy interference system, which is fundamentally different than the interference arrangement used in Bragg's X-ray microscope, certain changes are needed to calculate the necessary amplitudes, frequencies, and phases of the waves that are required to result in any given specific energy interference pattern to be generated in the newly defined circular space. Okuyama's analysis of his water-wave system is pertinent to analyzing such a circular electromagnetic ("EM") or acoustic wave system. First of all, instead of the simple x,y,z orthogonal Cartesian coordinates of the planar system used by Bragg, the present inventor conceives that the space would best be represented by a cylindrical coordinate system. (Alternatively, one could use a polar coordinate system, if only considering a circular plane, such as the surface of the water, as was done by Okuyama).

Figure 5B:
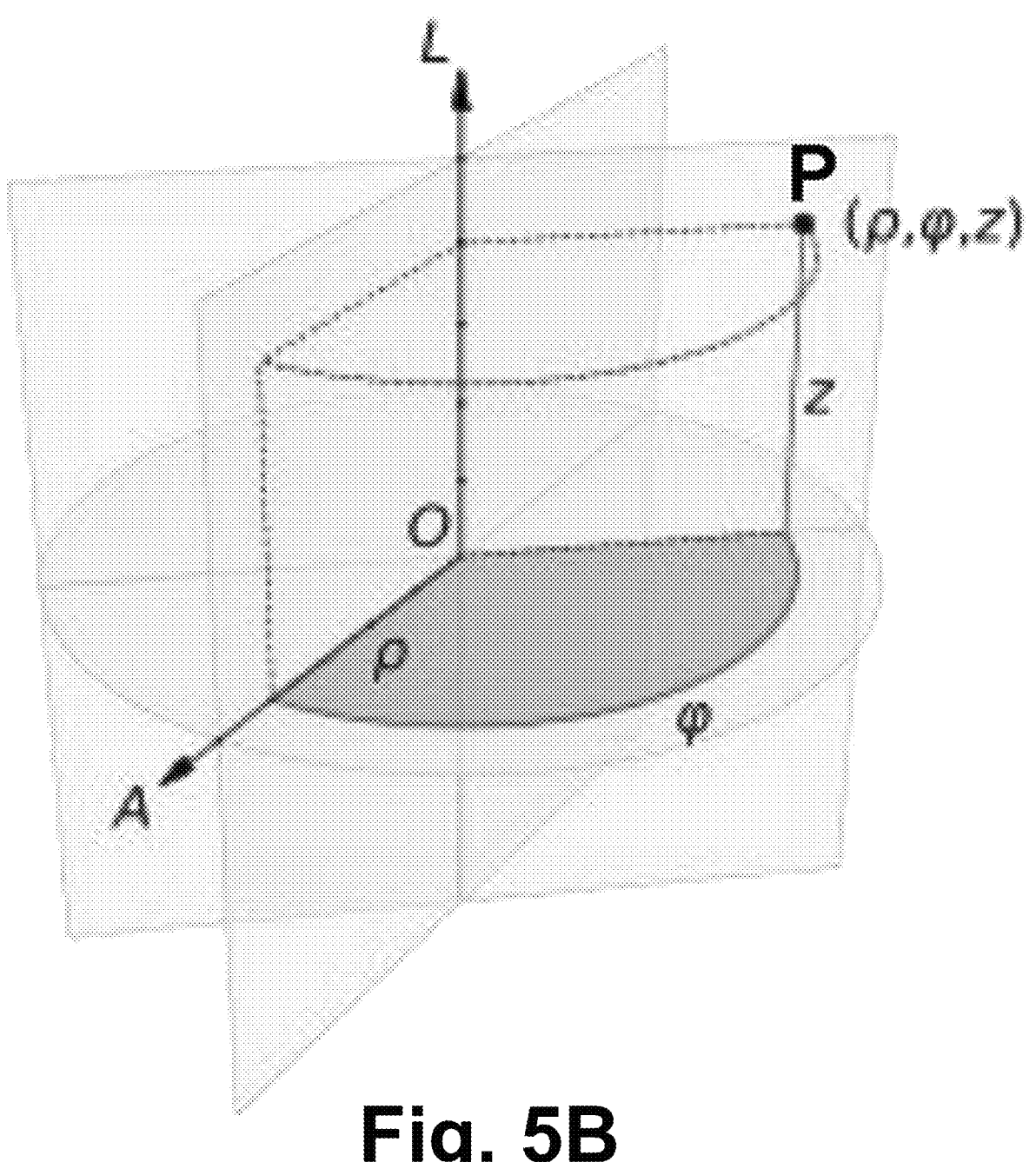
FIG. 5B is a diagram used to explain polar coordinates utilized in describing some examples of the present invention.

In such a system, as depicted in FIG. 5B, point positions are specified by the distance from a chosen reference axis, the direction from the axis relative to a chosen reference direction, and, in the case of a three-dimensional volume, the distance from a chosen reference plane perpendicular to the axis. The latter distance is given as a positive or negative number depending on which side of the reference plane faces the point. The "origin" of the system is the point where all three coordinates are equal to zero. This is the intersection of the reference plane and the axis. The axis is called the cylindrical or longitudinal axis, to differentiate it from the polar axis, which is the ray that lies in the reference plane, starting at the origin and pointing in the reference direction. The distance from the axis may be referred to as the radial distance or radius, while the angular coordinate is sometimes referred to as the angular position or the azimuth. The radius and the azimuth are together called the polar coordinates, as they correspond to a two-dimensional polar coordinate system in the plane through the point, parallel to the reference plane. The third coordinate may be called the height or altitude (if the reference plane is considered horizontal), or longitudinal position, or axial position. In FIG. 5B, in which the origin is labeled O, the polar axis is A, and the longitudinal axis is L. The dot is the point P with radial distance $\rho=4$, angular coordinate $\varphi=130°$, and height $z=4$. The three coordinates ($\rho$, $\varphi$, $z$) of the point P are also defined as:

The radial distance $\rho$ is the Euclidean distance from the z-axis to the point P.

The azimuth $\varphi$ is the angle between the reference direction on the chosen plane and the line from the origin to the projection of P on the plane.

The height z is the signed distance from the chosen plane to the point P.

A Fourier expansion in the p coordinate of cylindrical coordinates is equivalent to a "Fourier-Bessel" series. In mathematics, a Fourier-Bessel series is a particular kind of generalized Fourier series (an infinite series expansion on a finite interval) based on Bessel functions. Bessel functions for an integer a are known as cylinder functions or cylindrical harmonics because they appear in the solution to Laplace's equation in cylindrical coordinates, which we are using here, and are therefore especially important for many problems of wave propagation. Fourier-Bessel series are used in the solution to partial differential equations, particularly in cylindrical coordinate systems. The Fourier-Bessel series expansion employs aperiodic and decaying Bessel functions as its basis. A second Fourier-Bessel series is known as a "Dini series." Just as the Fourier series is defined for a finite interval and has a counterpart (the continuous Fourier transform over an infinite interval), the Fourier-Bessel series has a counterpart over an infinite interval, called the Hankel transform. In mathematics, the Hankel transform expresses any given function $f(r)$ as the weighted sum of an infinite number of Bessel functions of the first kind $J_v(kr)$, where "v" is the "order" and "k" is a scaling factor along the "r" axis. It is also known as the Fourier-Bessel transform. Just as the Fourier transform for an infinite interval is related to the Fourier series over a finite interval, the Hankel transform over an infinite interval is related to the Fourier-Bessel series over a finite interval. The Hankel functions are used to express outward- and inward-propagating cylindrical wave solutions of the cylindrical wave equation, respectively.

These concepts provide a mathematical method to analyze and subsequently generate high amplitude waves by constructive interference, referred to herein as "Desired Energy Peaks" ("DEPs"), as well as the generation of regions of destructive interference, referred to herein as "Desired Energy Cancellations" ("DECs"), at all other locations in space, utilizing reverse ring waves. In this description, to keep the explanation manageable and easier to present, only one circular plane in space will be considered (although as pointed out below, several such circular planes, perhaps defining a cylindrical volume, could be considered as well).

In accordance with the present invention, Spherical Bessel functions can also be used in a three-dimensional volumetric space. However, their use is not necessary for the particular embodiments set forth herein. Using waves that are collimated in one dimension (parallel to the plane of the circle), which can be done in three-dimensional space with the present invention, will confine them to a single plane, making a single plane analysis appropriate. As will be explained herein below, multiple circular systems can also be used in tandem to create a cylindrical system.

In accordance with the present invention, for electromagnetic (EM) waves, DEPs and DECs would be produced with the sum of ring waves, which are expressed mathematically by Bessel functions. Decomposing waves into Bessel functions is provided by the Dini expansion based on the Fourier-Bessel series expansion. This expansion depends on the specification of the wave emitters and the wave cavity (the space within the circle of wave emitters).

Ring waves disperse outward from an energy emitter in forward time and focus at the emitter source point in reverse time (for the purpose of calculations). To generate reverse ring waves, we would desirably use a wave cavity consisting of many absorbing (to suppress multiple reflections) wave emitters around the wave cavity. To absorb reflected RF waves, for instance, the cavity would desirably include cooled commercially available material coatings such as "ECCOSORB® high loss microwave absorbers," which are designed to attenuate electromagnetic interference by converting RF energy to heat. Optionally, for further reduction of reflections, each wave emitter would have a Faraday rotator (each of which with its own surface AR coated), or the equivalent, in front of it to act as an isolator, preventing reflection from a wave emitter back into the cavity.

In other embodiments of the present invention, acoustic DEPs and DECs could be correspondingly employed.

Fundamental Formula of the Wave Field

Figure 5C:
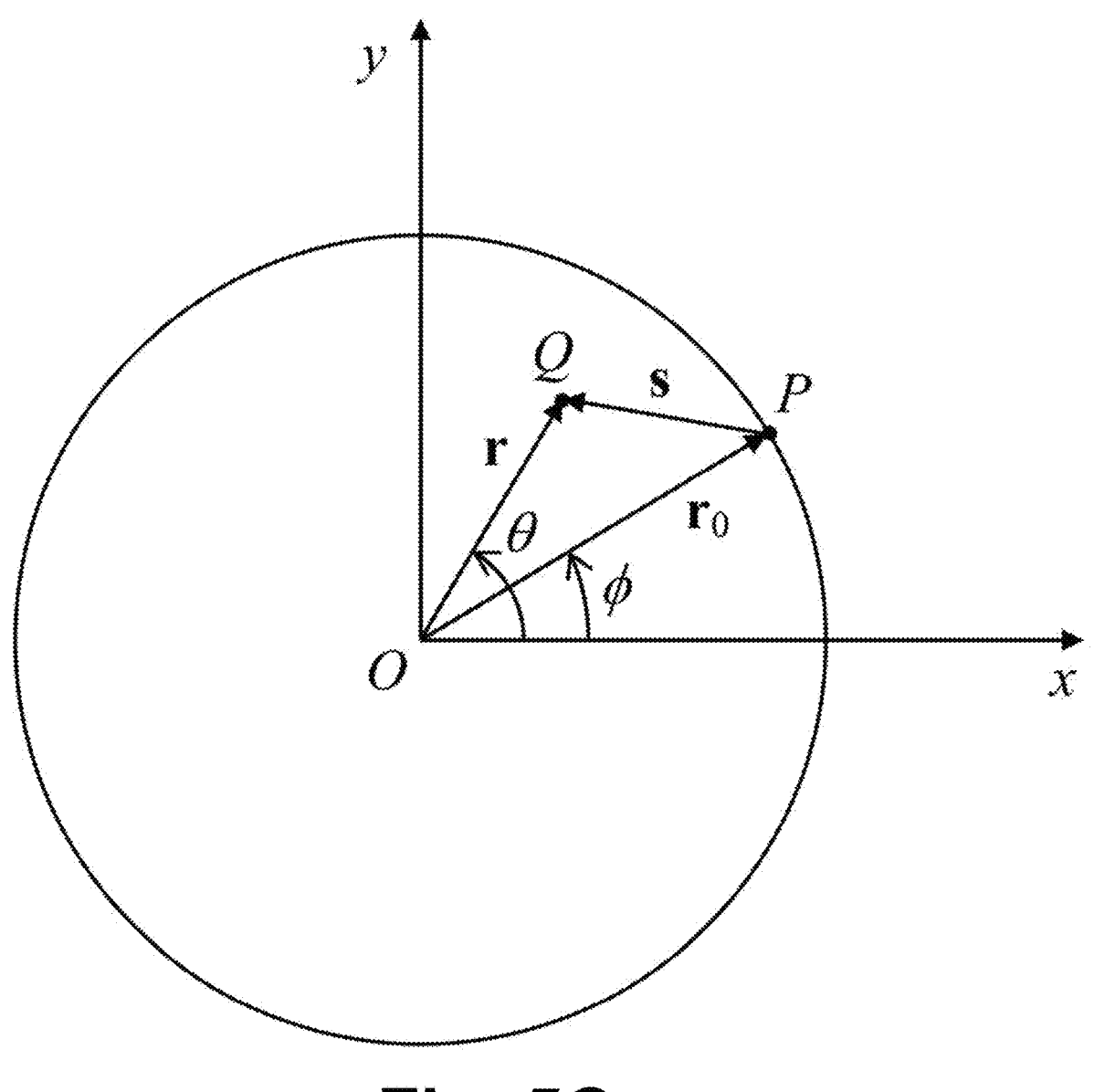
FIG. 5C is a diagram used to help explain a principle used in describing some examples of the present invention.

A wave field diverging from a wave emitter into the designated plane is expressed by $H_0^{(1)}$; the 0th order Hankel function of the first kind, obtained as a solution of Laplace's equation. This wave field sufficiently approximates the wave field generated by a segment of a multi-segmented wave emitter system. The wave field generated by the system is described by the superposition of the waves generated by individual wave emitters. A polar coordinate system is defined on the selected plane and the points P and Q are defined as shown in FIG. 5C. The point Q is located inside the circle with the center at the origin and the radius $r_0$ is the length OP. A single wave emitter is put at the point P. Arguments of P and Q are represented as $\Phi$ and $\theta$ respectively. Each position vector is defined as:

$$\overrightarrow{OP} = r_0, \quad \overrightarrow{OQ} = r, \quad \overrightarrow{PQ} = s \tag{1}$$

The relationship between the vectors is:

$$s = r - r_0. \tag{2}$$

Let "r" and "s" denote the magnitudes of the vectors "r" and "s" respectively. The magnitude "s," indicating the distance between P and Q, is described as:

$$s = \sqrt{s \cdot s} = \sqrt{r^2 + r_2^2 - 2rr_0 \cos(\theta - \phi)}. \tag{3}$$

Then, wave amplitude at the point of Q is described as:

$$\zeta(r, t) = \Re\left[H_0^{(1)}[ks] e^{-i\omega t}\right] \tag{4}$$

where k is a wave number and $\omega$ is an angular frequency. According to the addition theorem of the Hankel function, at $r < r_0$ we obtain:

$$H_0^{(1)}[ks] = \sum_{m=-\infty}^{\infty} J_m[kr] H_m^{(1)}[kr_0] e^{im(\theta - \phi)} \tag{5}$$

where, $J_m$ is the m-th order Bessel function of the first kind. Multiplying $e^{in\Phi}$ on both sides of the equation and integrating for $\Phi$ from 0 to $2\pi$, we can take just the n-th order term on the right-hand side. Consequently, the Bessel function of the first kind is obtained as:

$$J_n[kr] e^{in\theta} = \frac{1}{2\pi H_n^{(1)}[kr_0]} \int_0^{2\pi} H_0^{(1)}[ks] e^{in\phi} d\phi. \tag{6}$$

This equation implies that the wave field in the circle is expressed by the Bessel function when individual wave emitters are put on the circle with the radius $r_0$ between wave emitters. The integrated term of $e^{in\Phi}$ represents the phase difference between individual wave emitters. When n=0, the phase difference disappears and then ring waves appear. The wave field generated by wave emitters can be approximated by the discrete equation of Eq. 6 as:

$$J_n[kr] e^{in\theta} \sim \frac{\Delta\phi}{2\pi H_n^{(1)}[kr_0]} \sum_{j=1}^{N} H_0^{(1)}[ks_j] e^{in\phi_j} \tag{7}$$

where N denotes the number of wave emitters.

Fourier-Bessel Expansion of the Wave Field

An arbitrary wave field in the defined plane in space is geometrically described by the trigonometric series expansion for an angular coordinate denoted as $\theta$ and by the Fourier-Bessel series expansion for a radial coordinate denoted as r. Let $\xi(r, \theta)$ denote an arbitrary wave amplitude in the plane in space. This amplitude is described as:

$$\zeta(r, \theta) = \sum_{n=0}^{\infty} \sum_{m=1}^{\infty} (A_{nm} \cos n\theta + B_{nm} \sin n\theta) J_n[k_{nm} r] \tag{8}$$

where, $k_{nm}$ denotes the wave number for the radial coordinate. Using complex notation makes wave problem computations simpler and is given as:

$$\zeta(r, \theta) = \sum_{n=-\infty}^{\infty} \sum_{m=1}^{\infty} C_{nm} e^{in\phi} J_n[k_{nm} r] \tag{9}$$

The wave number $k_{nm}$ is determined from a boundary condition of the wave profile at the circle where individual wave emitters are located. When a boundary condition is $\xi(r_0, \theta)=0$ like on the membrane of a drum, the available wave number is provided as solutions of the equation $J_n[k_{nm} r_0]=0$. However, this condition is not suitable for this wave problem. Although the wave amplitude at the boundary can be set to zero mathematically, the number of arbitrary wave fields is then reduced. A boundary condition is concerned with the orthogonality of the Bessel function. Getting back to the Bessel's differential equation, we obtain the integral equation of the Bessel function as follows:

$$(k_i^2 - k_j^2) \int_0^{r_0} r J_n[k_i r] J_n[k_j r] dr = \tag{10}$$

$$r_0 \left( J_n[k_i r_0] \frac{dJ_n[k_j r]}{dr}\Big|_{r=r_0} - J_n[k_j r_0] \frac{dJ_n[k_i r]}{dr}\Big|_{r=r_0} \right)$$

When the right-hand side of this equation equals zero for $k_i \neq k_j$, the orthogonality of the Bessel function is represented. The simplest condition due to the orthogonality is when $J_n[k_i r_0]=0$ and $J_n[k_j r_0]=0$. When $J_n[k_i r_0] \neq 0$, a condition of:

$$k_j J_n'[k_j r_0] + h J_n[k_j r_0] = 0 \tag{11}$$

also derives the orthogonality. The prime symbol denotes differential. The parameter h is defined as:

$$h = -k_i \frac{J_n' \,[k_i r_0]}{J_n \,[k_i r_0]} \tag{12}$$

This condition is available for various wave fields because the wave profile at the circle is not restricted to $\xi(r_0,\theta)=0$. The Fourier-Bessel series expansion in the condition of Eq. 11 is known as the Dini expansion. Using the orthogonality in the condition of Eq. 11, we obtain the coefficient $C_{nm}$ as follows:

$$C_{nm} = \frac{\mu_{nm}^2}{\pi \left(h_n^2 + \mu_{nm}^2 - n^2\right) J_n \,[\mu_{nm}]^2} \times \tag{13}$$

$$\int_0^1 \int_0^{2\pi} \zeta \,(r_0\xi, \,\theta) \,\xi \,J_n \,[\mu_{nm}\xi] \,e^{-in\theta} d\theta d\xi$$

where, $\mu_{nm}=k_{nm}r_0$. The integral range for the radial coordinate is normalized. When DEPs clearly appear in the cavity space, only the specific DEPs are seen, with all other regions appearing as DECs, devoid of waves. Then, the boundary condition at the circle is appropriate for the situation where $\xi(r_0,\theta)=0$ and $\xi'(r_0,\theta)=0$. The boundary condition of the Bessel function represents a situation where $J_n(k_{nm}r_0)=0$ and $J'_n(k_{nm}r_0)=0$. Although the parameter $h$ is not defined for $J_n(k_{nm}r_0)=0$, taking into account the limit of $J_n(k_{nm}r)\rightarrow +0$ and $J'_n(k_{nm}r)\rightarrow -0$, at $r=r_0$, we obtain $h=1$. The normalized wave number $\mu_{nm}$ at $n=0$ is shown in Table 1 in FIG. 5D.

The available wave number must be chosen according to the wave generating performance of the wave emitter. The water wave prototype made by Okuyama et al. was composed of fifty absorbing wave-makers which can work within the angular frequency of $10.08<\omega<18.84$ [rad/s] and its radius is $r_0=0.8$ [m]. Consequently, the available range of the normalized wave number is shown as $8.17<\mu_{nm}<28.86$. Thus, the expansion terms of $m=4$ to 10 are available at $n=0$. The n-th term of expansion indicates the oscillation mode for the angular coordinate. A wave profile is assumed to be described by at least five wave-makers. Because their prototype was composed of fifty absorbing wave-makers, the order of the maximum mode is considered as ten. Therefore, they limited the order of the expansion term to ten. The wave field appearing at $t=t_0$ is expressed by:

$$\zeta \,(r, \,\theta, \,t) = \sum_{n=0}^{10} \sum_{m=4}^{10} (A_{nm} \cos n\theta + B_{nm} \sin n\theta) \times J_n \,[k_{nm}r] \cos \omega \,(t - t_0) \tag{14}$$

In their prototype, troughs appear around the peaks forming the letter "S". Converting the simulated data by Eq. 14 into a wave-generating signal through Eq. 7, they generated the water-wave letter "S" in their prototype as shown in the photograph of FIG. 5A.

Improvement by the Use of "Concentration Waves"

Figure 5E:
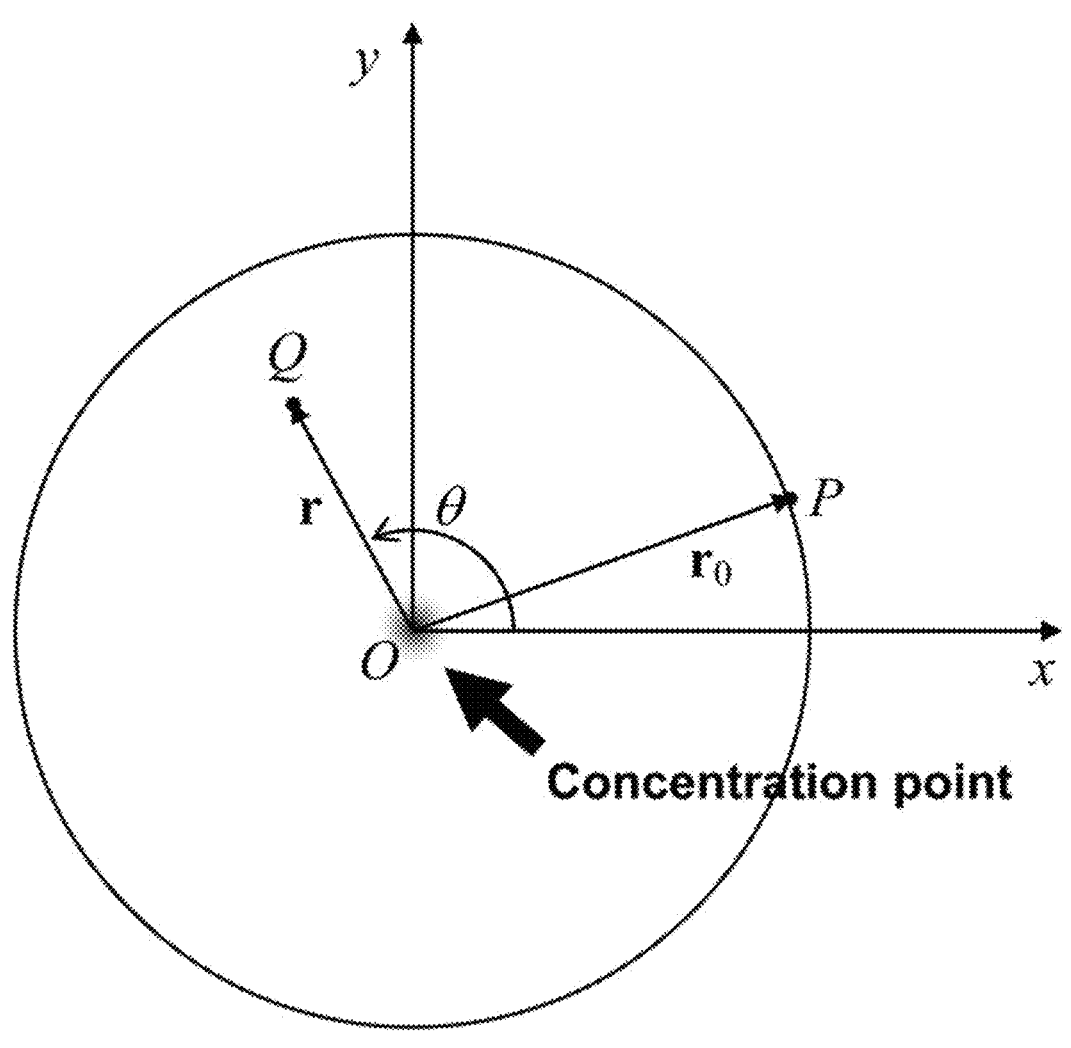
FIG. 5E is a diagram used to help explain a principle used in describing some examples of the present invention.

To make arbitrary wave fields more easily, the process can be improved by concentrating the wave energy at any arbitrary point which can be referred to as a "concentration point." The Dini expansion of Eq. 14 can be applied to making a concentration point in the center of the cavity as shown in FIG. 5E. The formed energy peak is expressed by the Bessel function of 0th order, because the peak is at the pole where $r=0$. Thus, the expansion term $n$ of the Fourier series expansion must be zero. The energy peak at the concentration point is consequently expressed as:

$$\zeta \,(r, \,\theta) = \sum_{m=4}^{10} A_{0m} J_0 \,[k_{0m}r] \tag{15}$$

Figure 5F:
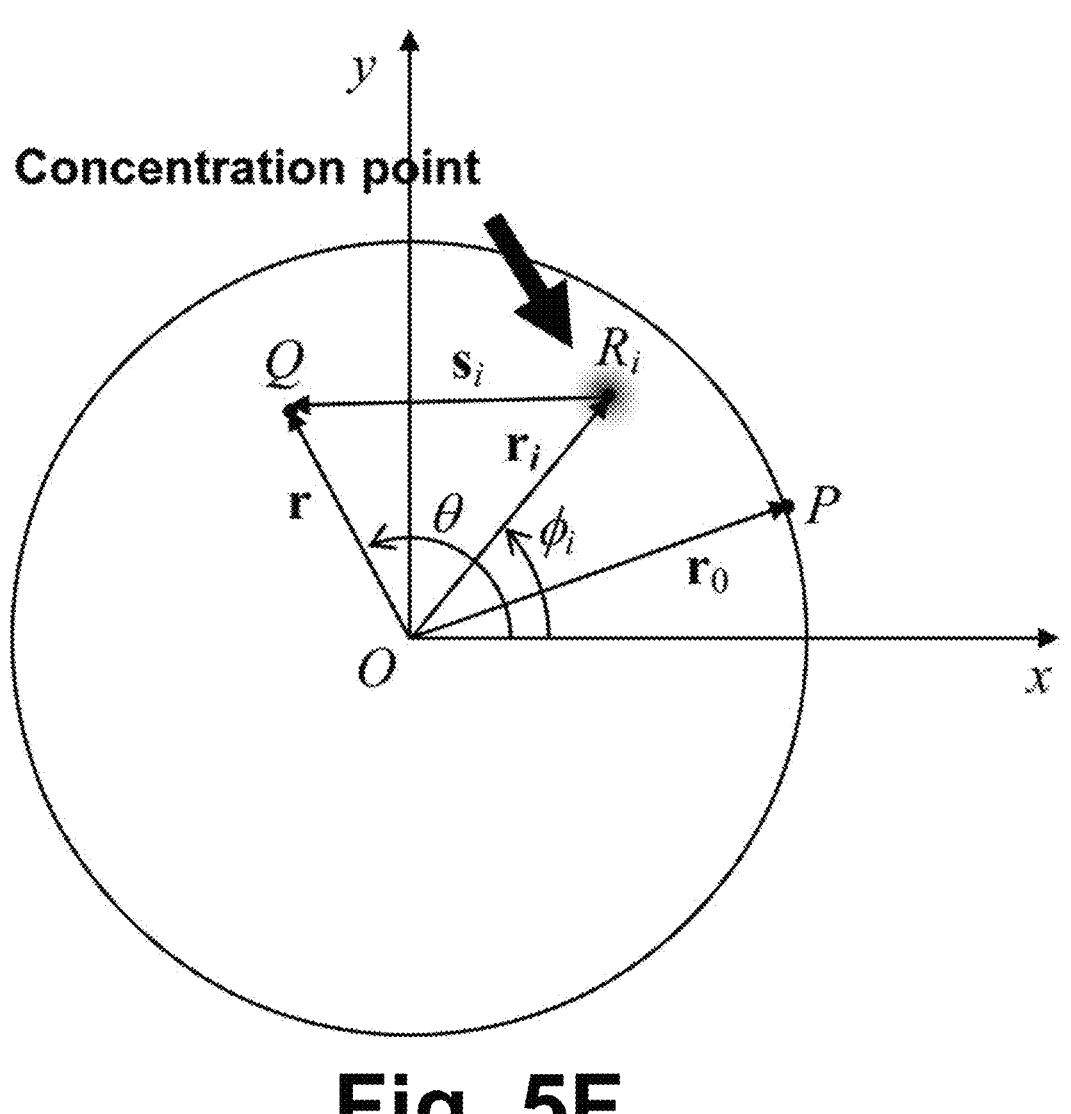
FIG. 5F is a diagram used to help explain a principle used in describing some examples of the present invention

When the concentration point is put at an arbitrary point $R_i(x_i,y_i)$ (as shown in FIG. 5F), the energy peak is described as:

$$\zeta_i \,(r, \,\theta) = \sum_{m=4}^{10} A_{0m} J_0 \,[k_{0m}s_i] \tag{16}$$

$$S_i = \sqrt{(x-x_i)^2 + (y+y_i)^2}$$

where

This wave profile at the concentration point is the same as that represented by Eq. 15. According to the addition theorem of the Bessel function, the 0th order Bessel function of the first kind is represented as:

$$J_0 \,[k_{nm}s_i] = \sum_{m=-\infty}^{\infty} J_m \,[k_{nm}r] \,J_m \,[k_{nm}r_i] \,e^{im(\theta-\phi_i)} \tag{17}$$

Substituting Eq. 6 for Eq. 17 at $n=0$, we obtain:

$$J_0 \,[k_{0m}s_i] = \int_0^{2\pi} \left\{ \sum_{m=-\infty}^{\infty} \frac{J_m \,[k_{0m}r_i] \,e^{im(\phi-\phi_i)}}{2\pi H_m^{(1)} \,[k_{0m}r_0]} \right\} H_0^{(1)} \,[k_{0m}s] \,d\phi \tag{18}$$

The integrated term in the middle brackets indicates the complex amplitude, including the phase difference between the wave emitters. Using concentration points, various DEPs can be formed in space freely at any location without the limitation of requiring the specification of the wave emitters. Such DEP locations are expressed as:

$$\zeta \,(r, \,\theta) = \sum_{i} \sum_{m=4}^{10} A_{0m} J_0 \,[k_{0m}s_i] \tag{19}$$

In this improved method, the Dini expansion is not required for each distribution of generated DEPs. The coefficient $A_{0m}$ of the Bessel function is determined by the wave profile at the concentration point and all of the wave profiles are the same. We only need to provide the location of the concentration point. As a result, the calculation becomes simpler, requiring less calculation time. A wave field generated by a single wave emitter can be described by the Hankel function of the first kind. A wave field generated in a circular cavity surrounded by a circle of wave emitters can be represented by superimposing the Hankel functions. According to the addition theorem of the Hankel function, this wave field is mathematically expressed by the n-th order Bessel function of the first kind with the origin in the center of the circle. Because an arbitrary wave field is decomposed into Bessel functions, and each Bessel function is decomposed into a Hankel function, the wave emission parameters of a single wave emitter can be specified for generating any arbitrary wave field and DEPs.

Figure 6:
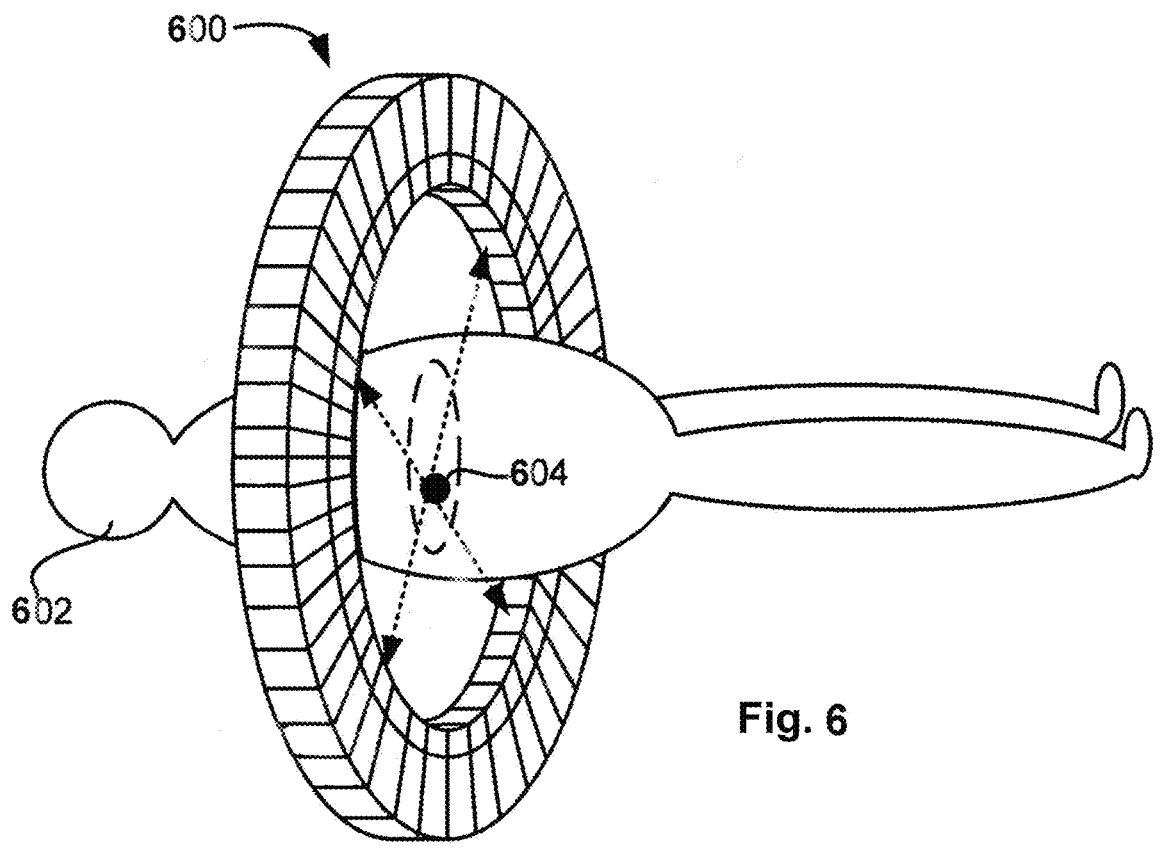
FIG. 6 is a diagram used to help explain a principle of an embodiment of the present invention.

In this first embodiment of the present invention, a system for the diagnosis and/or treatment of patients can be constructed using this technique with a circular arrangement of wave emitters 600 as depicted in FIG. 6, a patient 602 on a movable table is moved intermittently as needed through the circular plane defined by the circular arrangement of energy emitters (analogous to what is done with a conventional CT scanner) to bring tissue locations of interest 604, such as tumors, into the circular region where DEPs and DECs are produced for diagnosis and/or treatment.

Figure 7:
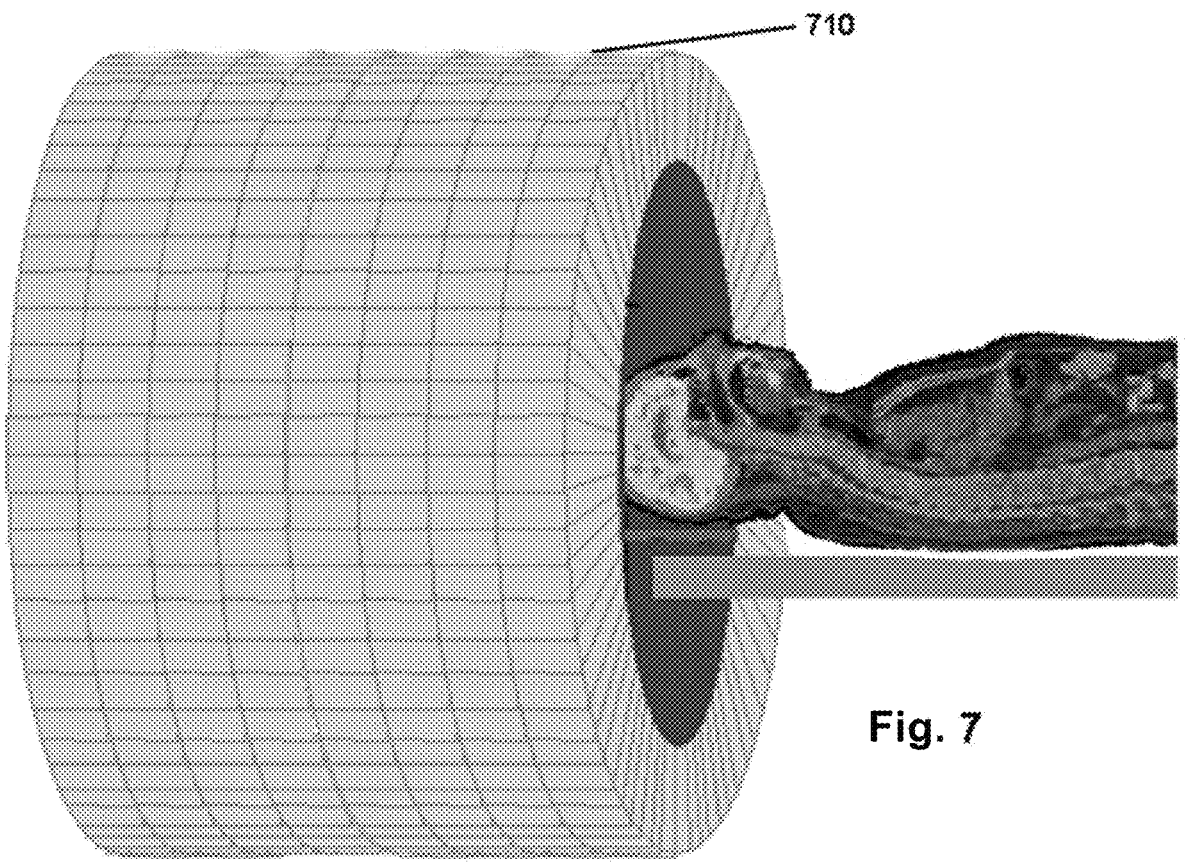
FIG. 7 is another diagram used to help explain a principle of an embodiment of the present invention.

As an alternative arrangement for utilizing this first embodiment, the diagnosis and/or treatment system consists of a series of parallel circular arrangements of energy emitters, each adapted to generate DEPs and DECs within its own circular plane, forming a cylinder 710 as shown in FIG. 7. Such an arrangement provides for the diagnosis and/or treatment of patient tissues in many parallel planes sequentially or simultaneously, potentially eliminating the need for patient movement during diagnosis and/or treatment. Such circular units could also be located around a patient in other arrangements other than parallel to each other. In configurations where there is a space between each two individual circular arrangements of energy emitters, the patient need only be moved that distance to address all points within the entire body very quickly.

Preferably, the treatment system would be built into an imager such as an MRI, PET, CT, or other scanner, such as those mentioned elsewhere herein. The scanner would detect the 3-D location of tumors or other tissues that need treatment and the detected 3-D coordinates would serve as the input for the treatment system to generate DEPs at designated locations, while canceling energy by destructive interference with DECs at all other locations occupied by the patient's body.

In this embodiment, traveling waves of different temporal frequencies, phases, and amplitudes are produced by the wave emitters which superimpose to produce DEPs and DECs by Fourier synthesis. However, since they are traveling waves, containing different temporal frequencies, they can only produce the proper superposition of constituent sine waves in the required phase relationship (for the Fourier synthesis and construction of DEPs and DECs where desired) once each period. Here, a period is the time it takes for the waves with different temporal frequencies to all line up as prescribed to provide the desired Fourier synthesis, until they line up again. Consequently, DEPs and DECs will appear for only part of the time in each cycle and a low level bias will appear at other times. This implies that, with this embodiment, the level of energy detectable in intervening and surrounding healthy tissues not requiring treatment will not be zero. However, due to the destructive interference produced in non-treatment regions, and the constructive interference produced in treatment regions during the times when the waves are in the desired phase relationship, the difference between the low level bias and the relatively high level DEPs could be great enough to prevent significant damage or unwanted negative effects in healthy tissues, while still providing sufficient energy for successful treatment of selected tissues, such as tumors.

The present inventor conceives that this embodiment is most likely to be a valuable system for hyperthermia, as it will reduce exposure of healthy cells to RF EM radiation and heat, as compared with currently available hyperthermia systems such as direct EM excitation and phased array systems. The optimal frequency for this embodiment is preferably between 100 and 200 MHz, but other frequencies, including higher frequencies up into the GHz range could be used since RF waves pass through the body fairly easily at many frequencies.

The present inventor also conceives of implementations of this embodiment utilizing X-rays and gamma rays. However, due to the presence of an incoherent bias, and the highly damaging effects of ionizing EM radiation, although this would be a safer alternative to constant radiation everywhere, as is used currently, the extent of advantages of using this embodiment for treatment with such radiation over conventional methods should first be confirmed through testing.

Time-Correlated Standing-Wave Interference (TiCSI)

For optimum treatment, the maximum amount of energy should be teleported to selected target cells or molecules while minimizing, and preferably, eliminating, delivery of energy to surrounding and intervening healthy cells. Consequently, the following preferred second embodiment of the invention is provided which virtually eliminates the formation of any bias. It uses a new technique referred to herein as "Time-Correlated Standing-wave Interference" (TiCSI—pronounced "Tixie"), to provide HET. This technique produces coherent interference between standing waves by time-correlating the positivity and negativity of standing waves at each instant of time where they overlap. To prevent the formation of a bias, all places in space occupied by a patient should consist only of stationary standing waves, rather than traveling waves, providing stationary destructive interference (DECs) at all locations except for the regions of selected target cells or molecules, which should consist of energy in the state of constructive interference (DEPs). Furthermore, the energy used should be as coherent as possible (both spatially and temporally) to maximize the contrast between locations of destructive and constructive interference. This second preferred embodiment can be accomplished by a system providing the proper arrangement and timing of overlapping standing waves.

Standing waves consist of nodes and anti-nodes, and, at first glance, don't appear to ever go negative anywhere. So this would seem to prevent the formation of destructive interference. Negative-going waves are essential to interfere with positive-going waves in order to produce destructive interference, leading one to conclude that standing waves can't be used to produce destructive interference in fixed regions of space. But the present inventor realized that, if a standing wave is viewed at individual instants of time, instead of as the time-averaged view normally taken, it can be understood that, during any one-cycle period, the state of an antinode is either positive or negative or somewhere in between.

Consequently, when it is negative, the wave can be made to interfere with another standing wave that is positive, for instance, at the same time and spatial location, and vice versa. Referring to FIG. 8A, a single standing wave pattern 800 consists of nodes 810 and anti-nodes 820. The nodes are always zero, containing no detectable energy, while the anti-nodes consist of a sinusoidally varying amount of energy which is positive for half the wave's duration and negative for the other half of the wave's duration (plus a brief time when it is zero). Although the perception of the antinode is that of constant energy that never goes negative, this is an illusion caused by the fact that this perception is an average over time.

Since the energy in the antinode is actually oscillating between positive and negative, it is possible to interact with the antinode as if it was always positive or always negative, by superimposing another similar standing wave on top of it with the proper phase relationship. Thus it is possible to produce an interference pattern that looks and behaves as if regular traveling sine waves could be made stationary in space and overlapped to create a stationary interference pattern that is constructive or destructive.

For instance, two standing waves can be overlapped, with one of the standing waves shifted parallel to the direction of wave propagation by one half the wavelength of the waves making up the standing waves (the shift being indicated by the horizontal arrow in FIG. 8B). This will cause the standing waves to cancel each other out completely by destructive interference. This happens because the nodes are always zero and the anti-nodes from the two standing waves are always out of phase with each other as they oscillate. This is illustrated in FIG. 8B in which wave 830 is one standing wave at a frozen instant in time (as indicated by the darker sine wave curve) and 840 is another standing wave, shifted in space to be out of phase with 830, at the same instant in time (as indicated by its darker curve). Although each standing wave is itself made by the overlap of two traveling sine waves moving in opposite directions, the standing waves are frozen in space and cancel each other out 850 (wave 830 is superimposed on wave 840, as shown by the vertical arrows, producing the result at 850), as if they were two superimposed traveling waves propagating in the same direction, but frozen in space out of phase. Instead of overlapping the standing waves in parallel, however, they can also be overlapped at an angle to each other to provide fixed regions of space that have constructive interference or regions of space that have destructive interference and regions of space where there is no interference (due to areas where waves aren't overlapping).

Furthermore, if many pairs of waves are overlapped, the phases of overlapping standing waves can be adjusted so that a selected region or regions of space always contain constructive interference, while other regions always contain destructive interference, or no interference (where waves don't overlap). By adjusting the number of standing waves that are overlapped, the angles and spacing between them, and the relative phases of the standing waves that do overlap each other, specific different static patterns of constructive and destructive interference can be created in space as desired.

Figure 9A:
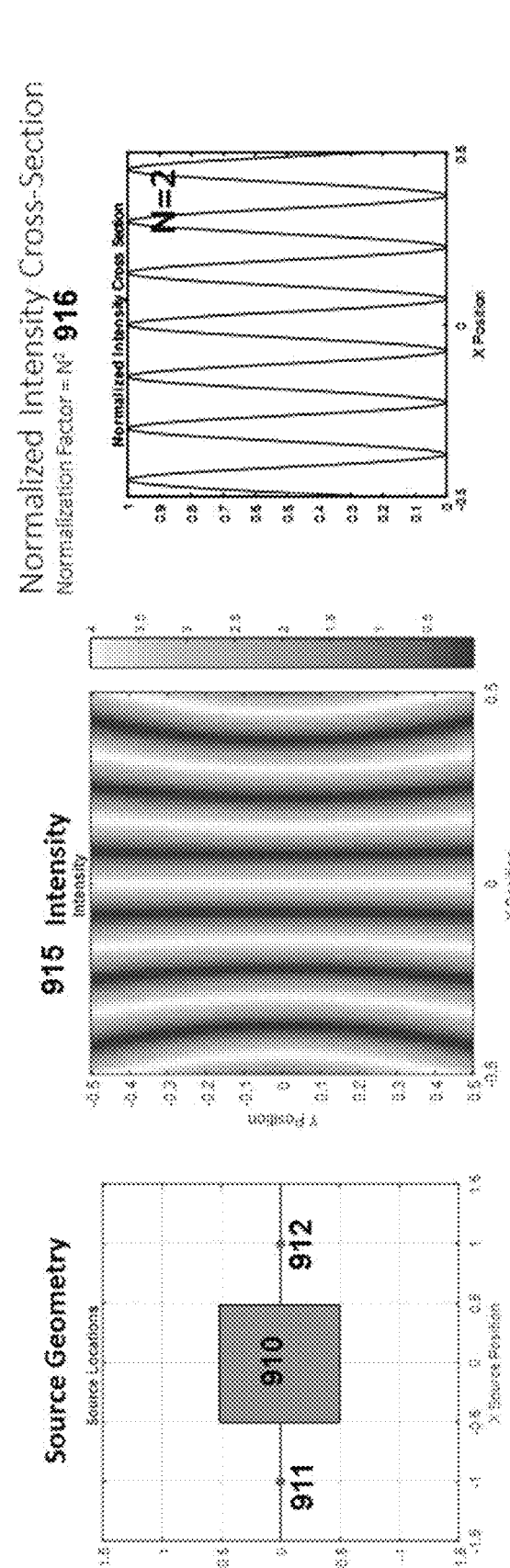
FIG. 9A is a diagram depicting two overlapping energy sources, the resulting interference intensity pattern produced, and a normalized intensity cross-section produced thereby.

Utilizing a sufficient number of such standing waves, it is also possible to create one region of constructive interference surrounded by destructive interference everywhere else over a large area. This can be better understood by referring to FIG. 9A. Region 910 depicts a square region of interest ("ROI") and two energy sources 911 and 912. Although these sources are shown as point sources, collimated plane wave sources, for instance, could be used as well. Wave 915 shows the detected standing wave intensity pattern resulting in the region 910, with energy intensity within the standing wave interference pattern indicated by the brightness levels shown. Element 916 shows the intensity cross-section passing through the center of the ROI 910 along line segment 911-912.

Figure 9B:
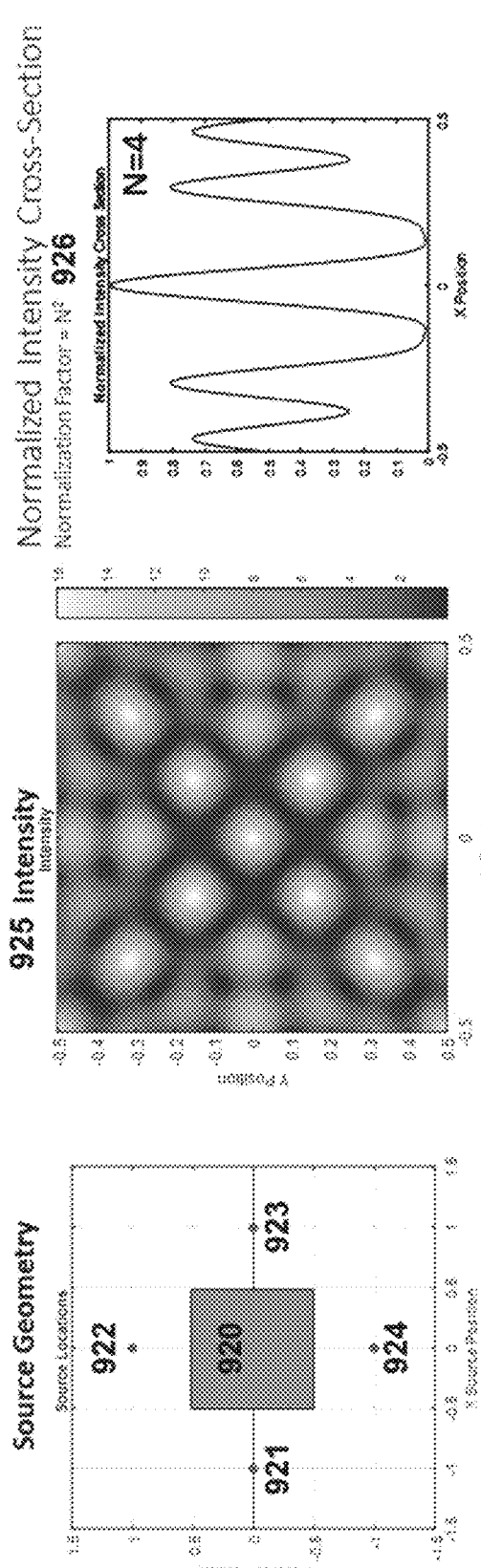
FIG. 9B is a diagram depicting four overlapping energy sources, the resulting interference intensity pattern produced, and a normalized intensity cross-section produced thereby.

In FIG. 9B, region 920 depicts an ROI surrounded by four energy sources 921, 922, 923, and 924. Pattern 925 represents the detected standing wave intensity pattern resulting within the region 920. Here a more complex pattern of constructive and destructive interference regions can clearly be seen. Pattern 926 shows the intensity cross-section passing through the center of the ROI region 920 along line segment 921-923. Note that the size of regions containing destructive interference around the central region has increased.

Figure 9C:
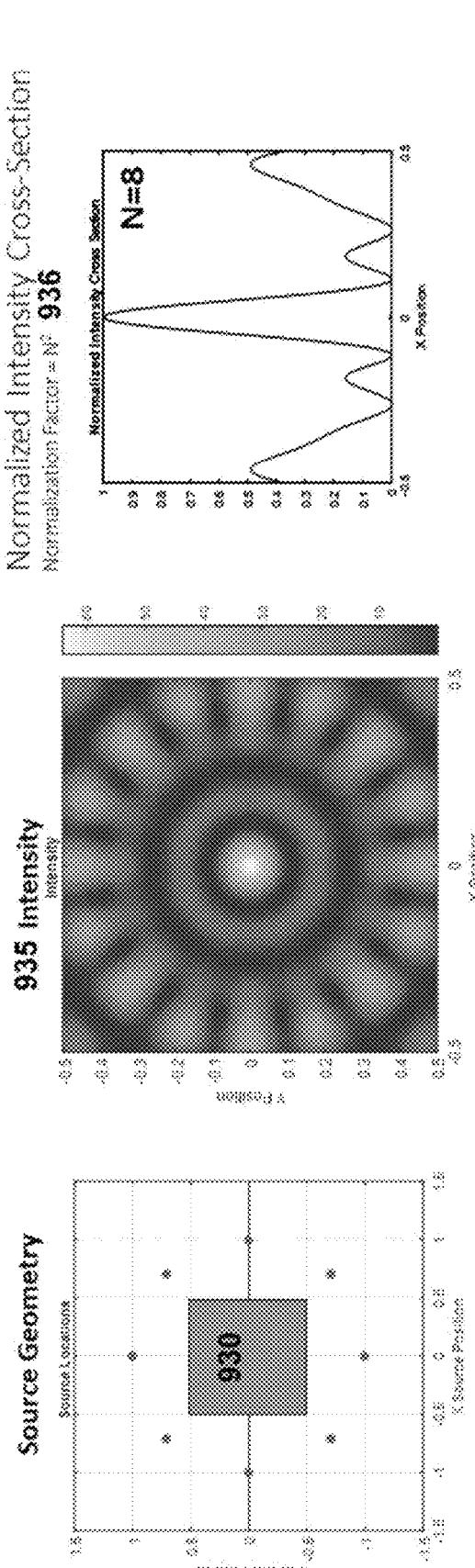
FIG. 9C is a diagram depicting eight overlapping energy sources, the resulting interference intensity pattern produced, and a normalized intensity cross-section produced thereby.

In FIG. 9C, region 930 depicts an ROI surrounded by eight energy sources and pattern 935 represents the detected standing wave intensity pattern that results. Here a different constructive and destructive interference pattern is seen, with even more regions of destructive interference. Pattern 936 shows the intensity cross-section passing through the center of the ROI region 930.

Figure 9D:
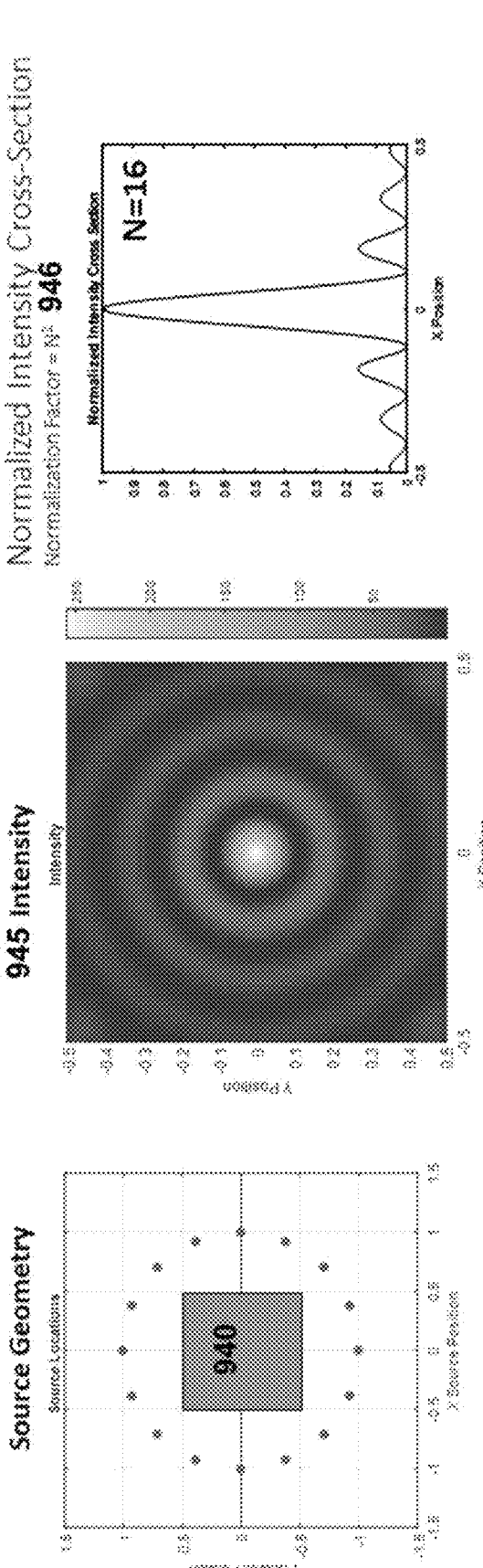
FIG. 9D is a diagram depicting sixteen overlapping energy sources, the resulting interference intensity pattern produced, and a normalized intensity cross-section produced thereby.

In FIG. 9D, region 940 depicts an ROI surrounded by 16 energy sources. Pattern 945 represents the detected standing wave intensity pattern that is seen. Here another different constructive and destructive interference pattern is produced with even more destructive interference outside of the center region. Pattern 946 shows the intensity cross-section passing through the center of the ROI region 940.

Note that, in all cases, due to the intentionally adjusted constant-in-phase relationship of the standing waves in the center of the ROI producing constructive interference, the center continues to be of high, growing intensity (as the number of beams increases), while the intensity of surrounding regions continues to decrease. Any point within the selected volume could be chosen as the point of constructive interference, instead of the center, by adjusting the phases of the beams to all be in phase at the chosen point. The amazing benefit of using coherent, monochromatic waves in this way is that when they overlap, instead of merely adding their intensities together, as happens with incoherent radiation superposition (such as in conventional hyperthermia or radiotherapy), these waves add coherently by constructive interference, creating an intensity equal to the sum of the amplitudes of the sources squared. Consequently, the more sources used, the less energy the system needs to use, and the less energy there is to adversely affect healthy cells. As the number of sources increases, the peak intensity increases by the square of the number of sources (if each source is equal and normalized to 1, for instance), while the energy distribution everywhere else gets closer and closer to zero due to destructive interference.

Also note that the high intensity distribution shown depicts a region of only a few wavelengths around the central peak. This means that the region of peak high energy is concentrated into a region size on the order of the wavelength of energy used. As can be seen by the graph 946, the intensity of peaks with successively larger radii continually decreases.

Figure 9E:
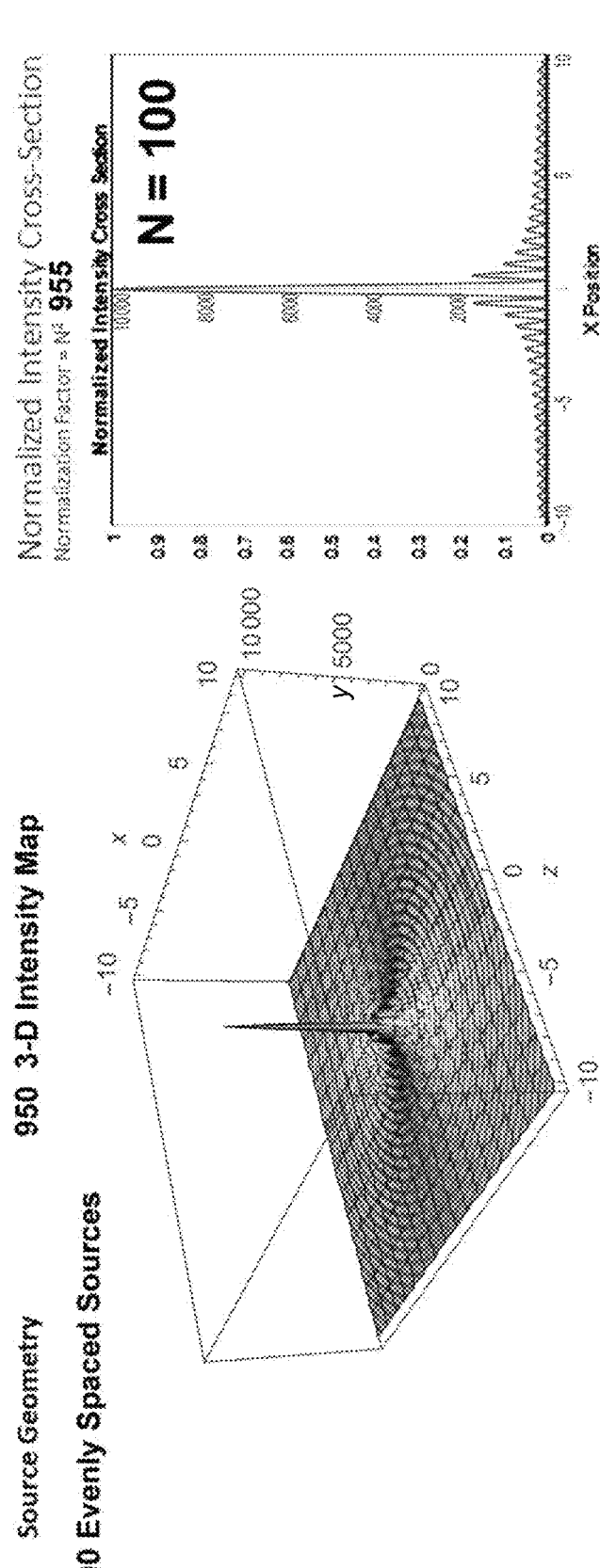
FIG. 9E is a diagram depicting the use of one hundred overlapping energy sources (not shown), the resulting 3-D intensity map produced, and a normalized intensity cross-section produced thereby.

In FIG. 9E, pattern 950 is a three-dimensional depiction of energy intensities in an ROI surrounded by one hundred energy sources. Pattern 955 shows the intensity cross-section passing through the center of the ROI 950. Note that, with 100 sources, the intensity of the DEP is 10,000 times the energy of a single source. Using higher intensity sources (and/or a larger number of sources) would make the central energy peak even higher, while the energy would still be nearly completely cancelled by destructive interference everywhere else, without creating a significant bias. For instance, using 316 sources would cause the constructive-interference peak (DEP) intensity to be approximately 100,000 times the energy of a single source. This technique, which is desirably utilized in HET in accordance with the present invention, is referred to herein as Coherent Intensity Amplification ("CIA"). The location of the peak can be selected to be anywhere within the ROI by adjusting the phasing of the various energy source beams. For independent confirmation, Mathematica was used to calculate the result shown in patterns 950 and 955 and Matlab was used to produce the results shown in patterns 910-945. All results were in agreement.

Coherent Intensity Amplification (CIA)

The following is an explanation of the basis of CIA. With coherent waves, relative phases and interference pattern intensities remain constant with time. From the energy law of Maxwell's theory, we know that u, the energy per unit volume, or energy density, in the electric field of a wave is given in mks units by:

$$u = \frac{1}{2} \mathcal{E} \vec{v} \cdot \vec{v}$$

where $\xi$ is the dielectric constant of the medium in which the wave is traveling and $\vec{v}$ is the Electric Field Vector. We can Write the Time Average of u as:

$$\langle u \rangle = \frac{1}{2T} \int_{-T}^{T} u \, dt$$
$$= \frac{1}{2} \mathcal{E} \cdot \frac{1}{2T} \int_{-T}^{T} \vec{v} \cdot \vec{v} \, dt$$
$$= \frac{1}{2} \mathcal{E} \langle \vec{v} \cdot \vec{v} \rangle$$

where 2T is the time over which the average is taken and where the brackets < > are a symbol for the time-averaging process. At any point in the wave, the Poynting vector may be interpreted as giving the magnitude and direction of the energy flow per unit time, per unit region, normal to the flow. It is common usage in classical optics to call the time average of the magnitude of the energy flow per unit time, per unit region, normal to the flow of power, per unit cross section, the intensity of the wave at that point. If we label the intensity $I_p$, then:

$$I_p = s \langle u \rangle = \frac{1}{2} s \mathcal{E} \langle \vec{v} \cdot \vec{v} \rangle$$

where s is the speed of the wave in the medium. In the mks system, $I_p$ is expressed in units of watts per square meter. On the other hand, in holography it is the custom to define intensity in an abbreviated form such that:

$$I = 2 \langle \vec{v} \cdot \vec{v} \rangle$$

The proportionality between I and $I_p$ allows us to express relative intensities equivalently in terms of I or $I_p$. Thus, if $\vec{r}_1$ is the radius vector to one point in a beam and $\vec{r}_2$ is the radius vector to another, the relative intensities at the two points are given by:

$$\frac{I(\vec{r}_1)}{I(\vec{r}_2)} = \frac{I_P(\vec{r}_1)}{I_P(\vec{r}_2)}$$

Insight into the interference process is gained by substituting expressions for relevant wave amplitudes into $I = 2 \langle \vec{v} \cdot \vec{v} \rangle$, the intensity defined in Eq. (1.1). If the electric field $\vec{v}$ exists as a physical quantity, it must be a real function of space and time, and if it represents a truly monochromatic wave, it must be a simple harmonic function of time. We can let f be the frequency of the wave oscillation and write the following for the electric field:

$$\vec{v} = \vec{a} \cos (2\pi f t + \varphi)$$

Here a is the amplitude, a function of spatial coordinates only, and φ is the phase function of spatial coordinates only. Substitution of Eq. (1.2) into Eq. (1.1) yields:

$$I = \frac{2}{2T} \int_{-T}^{T} \frac{\vec{a} \cdot \vec{a}}{2} [1 + \cos (4\pi f t + 2(\varphi)] \, dt = \vec{a} \cdot \vec{a} \text{ for } T \gg 1/f$$

$$= a^2 = a_x^2 + a_y^2 + a_z^2$$

with $a_x$, $a_y$, and $a_z$ representing the Cartesian components of the vector a. Intensity is thus equal to the square of the amplitude a of the electric field. As is evident from Eq. (1.4), measurement of the intensity of a single wave provides no information about the phase of the wave. Interference patterns imply the simultaneous presence of more than one wave, and so we must consider how to add a number of interfering monochromatic waves and then apply Eq. (1.1). Each wave may be represented by $\vec{v}_i = \vec{a}_i \cos(2\pi f t + \varphi_i)$ where the frequency $f$ has a single value, identical for each wave ($\vec{v}_i$ is the electric field vector in the region of interference). The sum of these sinusoidal functions is a sinusoid itself, and thus, we have:

$$\vec{a}_1 \cos (2\pi f t + \varphi_1) + \vec{a}_2 \cos (2\pi f t + \varphi_2) + \ldots = \vec{a} \cos (2\pi f t + \varphi)$$

The above may be rewritten as:

$$\text{Re} \left[ \vec{a}_1 \exp [i (2\pi f t + \varphi_1)] \right] + \text{Re} \left[ \vec{a}_2 \exp [i (2\pi f t + \varphi_2)] \right] + \ldots =$$
$$\text{Re} \left[ \vec{a} \exp [i (2\pi f t + \varphi)] \right]$$

where Re[ ] indicates the real part of the complex quantity within the brackets. Computations are made simpler by using complex notation, and we can facilitate its use by dropping the reminder that the wave functions are real. At this point we can distinguish several terms which we can apply to the complex wave function of space and time appearing on the right-hand side of Eq. (1.6). The complex quantity[1]:

[1] Note: Complex quantities are denoted by boldface type.

$$\vec{v} = \vec{a} \exp(i\varphi) \exp(2\pi i f t)$$

containing the temporal phase factor varying at the oscillation frequency $f$ is called the "complex electric field vector." The complex quantity[1]:

$$\vec{a} = \vec{a} \exp(i\varphi)$$

contains only amplitude and phase factors which do not vary at the frequency $f$ and is called the "complex amplitude vector." The real quantity $\vec{a}$ is simply the amplitude vector.

Dropping the symbol Re[ ] in Eq. (1.6) and dividing each term by exp($2\pi$ift), we obtain:

$$\vec{a}_1 \exp (i\varphi_1) + \vec{a}_2 \exp (i\varphi_2) + = \vec{a} \exp (i\varphi) = \vec{a} \qquad (1.7)$$

Thus the complex amplitude vector of a sum of monochromatic waves is obtained by adding the complex amplitude vectors of the individual waves according to the rules for adding complex numbers.

We can now write the intensity I in Eq. (1.3) in terms of a by forming the product $\vec{a} . \vec{a}^* = [\vec{a} \exp(i\varphi)] \cdot [\vec{a} \exp(-i\varphi)] = \vec{a} \cdot \vec{a}$ so that:

$$I = \vec{a} \cdot \vec{a} = \vec{a} \cdot \vec{a}^* = \qquad (1.8)$$

$$[\vec{a}_1 \exp (i\varphi_1) + \vec{a}_2 \exp (i\varphi_2) + \ldots] X [\vec{a}_1 \exp (-i\varphi_1) + \vec{a}_2 \exp (-i\varphi_2) + \ldots]$$

where the asterisk indicates the complex conjugate. Holography is often concerned with the interference of two waves, a subject wave and a reference wave. In this case, the intensity I in Eq. (1.8) takes the form:

$$I = \vec{a} \cdot \vec{a} = \vec{a}_1 \cdot \vec{a}_1 + \qquad (1.9)$$

$$\vec{a}_2 \cdot \vec{a}_2 + \vec{a}_1 \cdot \vec{a}_2 \left[\exp [i (\varphi_2 - \varphi_1)] + \exp [-i (\varphi_2 - \varphi_1)]\right]$$

$$\text{or } I = I_1 I_2 + 2\vec{a}_1 \cdot \vec{a}_2 \cos (\varphi_2 - \varphi_1)$$

Thus the intensity at any point in the interference pattern formed by two wave trains is the sum of the intensities of the individual waves plus an interference term. Relative phase information is contained in this time-independent interference term. With two interfering waves, the resultant intensity I can be greater or less than the sum of their intensities. For example, if the waves have constant and equal amplitudes $$|\vec{a}_1| = |\vec{a}_2| = (I_1)^{1/2} = (I_2)^{1/2}$$

Then, from Eq. (1.9), the maximum value of the intensity I is four times the individual intensities $I_1$ or $I_2$ and the minimum value of I is 0. Consequently, with the coherent interference of waves, the resulting intensity I reduces to the square of the sum of the amplitudes of the interfering waves plus the interference term value. Consequently, by coherently adding additional sources, the peak region of constructive interference (DEPs) increases exponentially, while DECs get closer and closer to zero.

The areas of destructive interference (DECs) described above, contain nearly no energy, but some small amount of energy can be seen to still remain. There are several ways to further reduce the energy in destructive interference areas (DECs). As just described, increasing the number of sources in the ring greatly increases the peak energy in the constructive interference area(s) (DEPs). Consequently, the amount of energy in each energy source can be reduced, bringing down the DECs further, while reduction of the DEPs can still provide more than sufficient energy (due to CIA) to accomplish desired tasks.

Figures 15A, 15B, 15C, 15D, 15E, 15F:
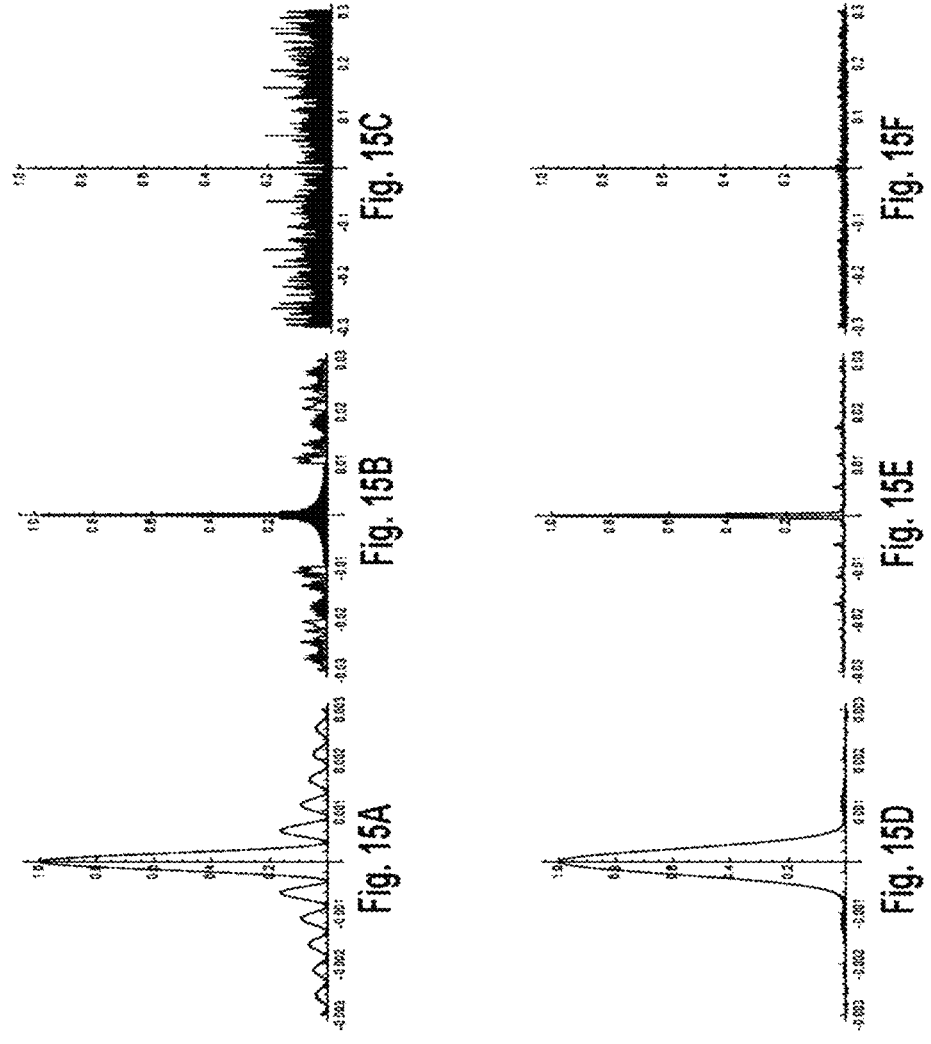
FIG. 15A is a diagram illustrating the energy profile in an area, based on an embodiment of the present invention where waves are emitted at 300 GHz.
FIG. 15B is a diagram illustrating the energy profile in a larger area than depicted in FIG. 15A, based on an embodiment of the present invention where waves are emitted at 300 GHz.
FIG. 15C is a diagram illustrating the energy profile in a much larger area than depicted in FIGS. 15A and 15B, based on an embodiment of the present invention where waves are emitted at 300 GHz.
FIG. 15D is a diagram illustrating the energy profile in the same area as depicted in FIG. 15A, based on an embodiment of the present invention where waves of five different frequencies are added to the waves emitted at 300 GHz.
FIG. 15E is a diagram illustrating the energy profile in the same area as depicted in FIG. 15B based on an embodiment of the present invention where waves of five different frequencies are added to the waves emitted at 300 GHz.
FIG. 15F is a diagram illustrating the energy profile in the same area as depicted in FIG. 15C, based on an embodiment of the present invention where waves of five different frequencies are added to the waves emitted at 300 GHz.

Alternatively, instead of just using a ring of sources that are all emitting the same frequency, other sets of sources can also be placed into the ring which emit other frequencies to further cancel harmonic ringing. This can provide a superposition of further destructive interference at different locations where there is still some residual energy in the pattern produced by the sources which emit only one frequency, especially at small distances from the constructive-interference peak, where residual energy is highest. This can further eliminate energy within the areas where destructive interference is desired (DECs). This is illustrated in FIGS. 15 A through 15 F. FIG. 15 A shows the energy profile within the 3 mm area centered around a DEP produced by 64 evenly-spaced sources located in a 2 m diameter ring, with each source emitting an electromagnetic wave at 300 GHz (with a wavelength of 1 mm). FIG. 15 B shows the energy profile within the 3 cm area centered around the same DEP. FIG. 15 C shows the energy profile within the 0.3 m area centered around the same DEP. The graphs show that there is still some residual energy in the DEC areas. FIG. 15 D shows the energy profile within the same 3 mm area as depicted in FIG. 15 A, centered around the same DEP, but wherein five additional frequencies (39.9 GHz, 91.6 GHz, 144 GHz, 196 GHz, and 248 GHz) are added to the original 300 GHz waves. These frequencies were chosen by analyzing their Bessel function patterns to find which harmonic patterns would cause destructive interference with the initial interference pattern generated by the use of only one frequency. The additional destructive interference created dramatically reduces the amount of remaining energy in the destructive interference areas (DECs). FIG. 15 E shows the energy profile within the same 3 cm area shown in FIG. 15 B, centered around the same DEP, irradiated with the same six different frequencies. FIG. 15 F shows the energy profile within the 0.3 m area shown in FIG. 15 C, centered around the same DEP, irradiated with the same six different frequencies.

As a person skilled in the art will appreciate, other configurations of sources, phases, and frequencies can similarly be used to further reduce the energy in DEC areas, as well as to increase the energy in DEP areas.

Utilizing this second embodiment, a patient can be placed within the ROI to teleport a large amount of energy by constructive interference to any selected region, surrounded by an area of destructive interference, anywhere within the plane defined by the circle of energy sources surrounding the patient, as depicted in FIG. 6.

Just as a single hologram can reconstruct several individual points in space, as is well known in the art, including if it is a computer-generated hologram (CGH), the array of sources in the ring of this second embodiment of the present invention behaves like an electronic hologram and can be configured (adjusting phases and amplitudes, at a given frequency, of each emitter) to produce two or more DEPs within the area enclosed by the ring of sources. This means that two or more spots can be treated simultaneously within a patient placed within the ring.

Again, to eliminate the need to move a patient in and out of a circular array of energy sources during diagnosis and/or treatment, a cylindrical array of energy sources can be used instead, as depicted in FIG. 7, or other orientations of circular arrays could be used. Unlike the previously discussed first embodiment, all energy is coherent and of the same temporal frequency, and remains in the entire patient space as a fixed standing wave pattern the entire time, resulting in no bias. Accordingly, in this second embodiment of the invention, the energy applied to the patient can be increased as much as necessary to reach deep within the patient and supply sufficient energy intensity to the selected region for diagnosis and/or treatment, without sending dangerous energy to intervening and surrounding healthy cells. This is especially useful at high RF frequencies that normally provide very little penetration. This is possible because energy in the state of destructive interference does not interact with the patient's healthy tissues (or any other tissues) located in the regions of destructive interference. Therefore, the energy is not absorbed or scattered, and doesn't produce heating, ionization, or tissue damage. Since the energy is not absorbed, it can continue to penetrate through the body unobstructed, at high intensity, despite its high frequency, until it reaches the region of constructive interference, where it "re-materializes" to produce a maximum effect.

The size of the region (the resolution) of DEP maximum intensity is a function of the wavelength used ($\sim\lambda/2$). Clearly, at high frequencies (such as with millimeter waves at 300 GHz and higher), this provides the ability to deliver energy precisely to very small selected regions ($\sim$1 mm or less). As mentioned above, diagnosis and/or treatment energy can be delivered to one small spot at a time or, alternatively, the interference pattern can be calculated to create intentional "hot spots" (DEPs) at several locations for simultaneous diagnosis and/or treatment.

Figure 16:
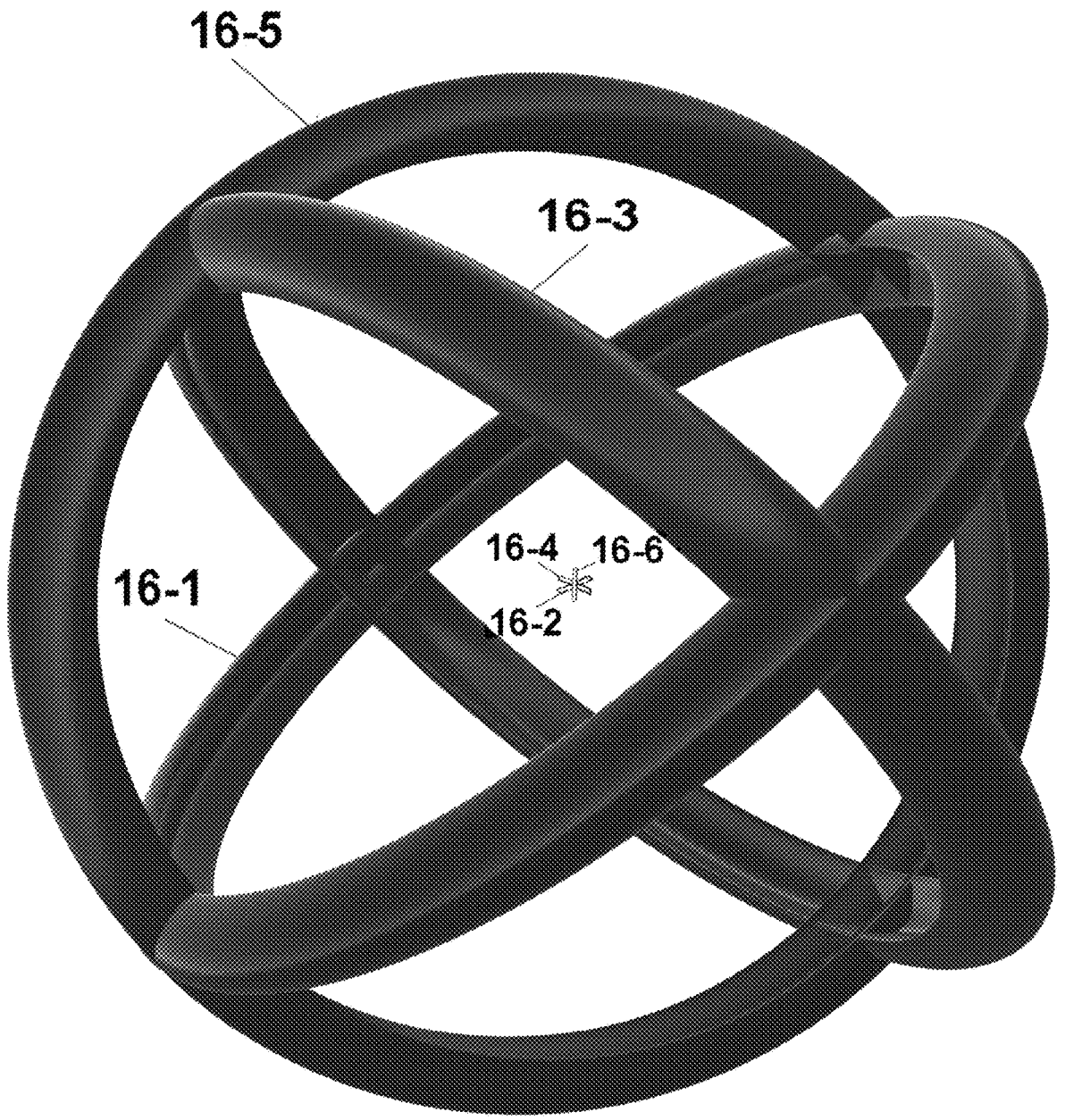
FIG. 16 is a diagrammatic illustration of mutually perpendicular HET rings.

Although using this second embodiment with a ring around a patient can produce a spot of constructive interference within the radiating ring that has a diameter on the order of the wavelength of the energy used, the thickness of the constructive interference spot (DEP) is not going to be smaller than the thickness of a single energy emitter. When very high frequency waves (such as 300 GHz) are used, this thickness is likely going to be larger than the diameter of the DEP, giving the generated DEP a shape similar to a grain of rice or a sewing needle. If the three-dimensional area to be treated by a DEP needs to be symmetrical, while being smaller than the size of an energy emitter, a perpendicular ring can be added. This situation is depicted in FIG. 16, wherein 16-2 is a first HET ring which produces a DEP 16-2. A second perpendicular HET ring is shown at 16-3, which produces a DEP at 16-4. This will create two perpendicular rice-grain- or sewing-needle-shaped DEPs that are perpendicular to each other, intersecting at a point at their centers, that is symmetrical and only about the size of the wavelength of the energy used in all three dimensions. Thus, the energy intensity at the overlapped energy point will be approximately twice what it is at any other location in the non-overlapped DEP areas. Utilizing additional rings at other angles (such as the ring labeled 16-5), creating further DEPs (such as shown at 16-6) that overlap at the same intersection point, will further increase the difference between the energy intensity at the overlap point and all other points in the non-overlapping areas of the DEPs that are produced. The resulting difference in energy intensity can provide a three-dimensionally symmetrical DEP overlap point that is sufficiently intense to produce the desired effect, while surrounding areas can have no significant negative effect. At frequencies that do not normally penetrate the body well, the destructive interference field can first be set up at low intensity before the body is inserted into the field (or else the energy may never get into the body, due to scattering and absorption, to create destructive interference). Once the patient's body is in place and the region of constructive interference is at the spot to be treated, the intensity can be turned up to produce the desired effect. Temperature monitoring of spots within the body for real-time feedback can be accomplished with MRTh, for instance, as explained herein below.

A third embodiment consists of a simpler and more compact arrangement. This method combines Fourier synthesis with superimposed standing waves (using TiCSI with CIA) in a different way. It has some similarities to Bragg's X-ray microscope and to the second embodiment described herein above, but instead of sending traveling waves at a perpendicular angle to the plane of standing waves and Fourier synthesis, as Bragg did, everything is done in the same single plane or volume along a single beam path. This arrangement eliminates traveling waves in the patient space, which could create damage to healthy cells in a diagnosis and/or treatment system. In addition, it doesn't require beams from different angles located all the way around the patient, as in the second embodiment. Instead, it only requires one beam path produced by two "beams" approximately 180° apart, paving the way for building a hand-held unit. Additionally, even though the two "beams" used in this third embodiment consist of beam components of different spatial frequencies (as in Bragg's system) to allow for Fourier synthesis, coherence is maintained since only one temporal frequency or band of frequencies is used, as in the second embodiment herein above, and the creation and use of only standing waves, unlike the Bragg system, eliminates the formation of a bias. This is because the different spatial frequencies are all derived from beams of a single temporal frequency or frequency band that are pulsed at the desired spatial frequencies and phase shifted using phase modulators.

Figure 10:
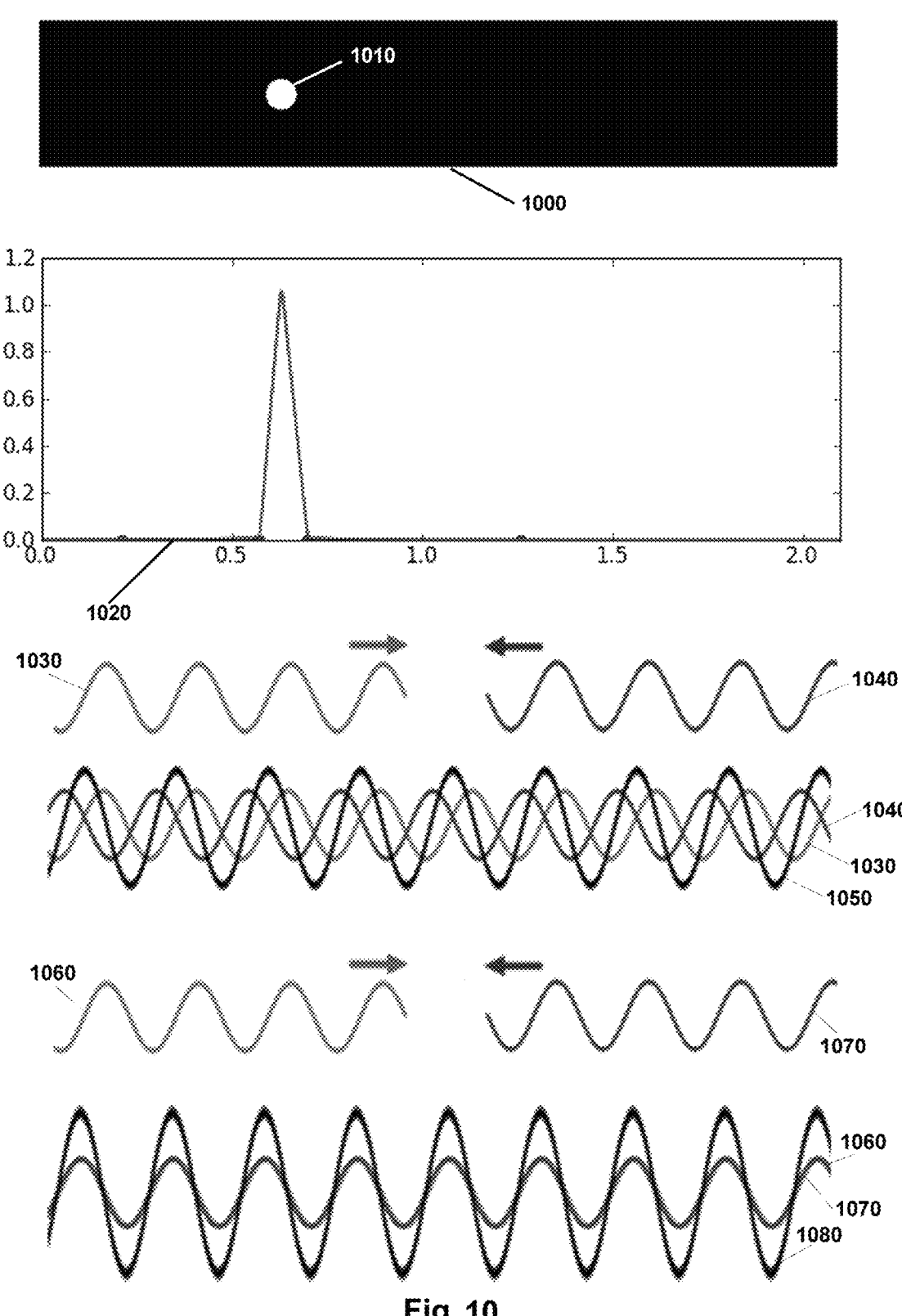
FIG. 10 is a diagram used in the description of an embodiment of the present invention depicting a point of interest, a corresponding complex curve, and various stages of standing wave production, which is used to reconstruct the complex curve by Fourier synthesis.

To employ this embodiment, as shown in FIG. 10, first the point (or points) 1010 within the defined space 1000 that are to contain DEPs are defined. The energy profile 1020 of that space 1000 is considered a complex wave and is Fourier analyzed, producing a Fourier series of values defining multiple sine waves. Two coherent beams 1030 and 1040 are directed through phase, frequency, and amplitude modulators (not shown-such as electrically controlled lithium niobate crystals) into the space 1000 from opposite directions by, for instance, propagating through fiber optics. When the beams overlap in the space 1000, they produce a standing wave component beam 1050 which corresponds to the first sine wave component of the calculated Fourier series. At the same time, two other beams 1060 and 1070 (shown as in phase and nearly coincident) are introduced from opposite directions, also similarly passing through modulators, into the space 1000, for instance through further fiber optics, and overlap to produce a second standing wave component beam 1080 which corresponds to a second sine wave component of the calculated Fourier series. This is repeated simultaneously with as many sets of beams as there are sine wave components (such as between 100 and 1000 components) to be added together from the Fourier series by fiber optic beam combiners, for instance. The action of the fiber optic beam combiners is to combine all such standing wave component beams into a single "composite beam."

For further clarification, each pair of oppositely propagating, traveling wave beams produces a sine wave component beam of the Fourier series when they overlap as a standing wave in the space 1000. These component beams are modulated as necessary to adjust their phase position with respect to the other component standing wave beams produced (using TiCSI), resulting in the aforementioned "composite beam" when they are all superimposed onto each other. This produces Fourier synthesis of the complex wave initially defined. Alternatively, instead of using optical fibers to combine all the component beams, although not preferred, many beam splitters can be used in series to introduce the many beams into the desired single beam path. One or more such composite beams can be generated in a defined space within the body to treat different selected areas sequentially or simultaneously.

Figure 17:
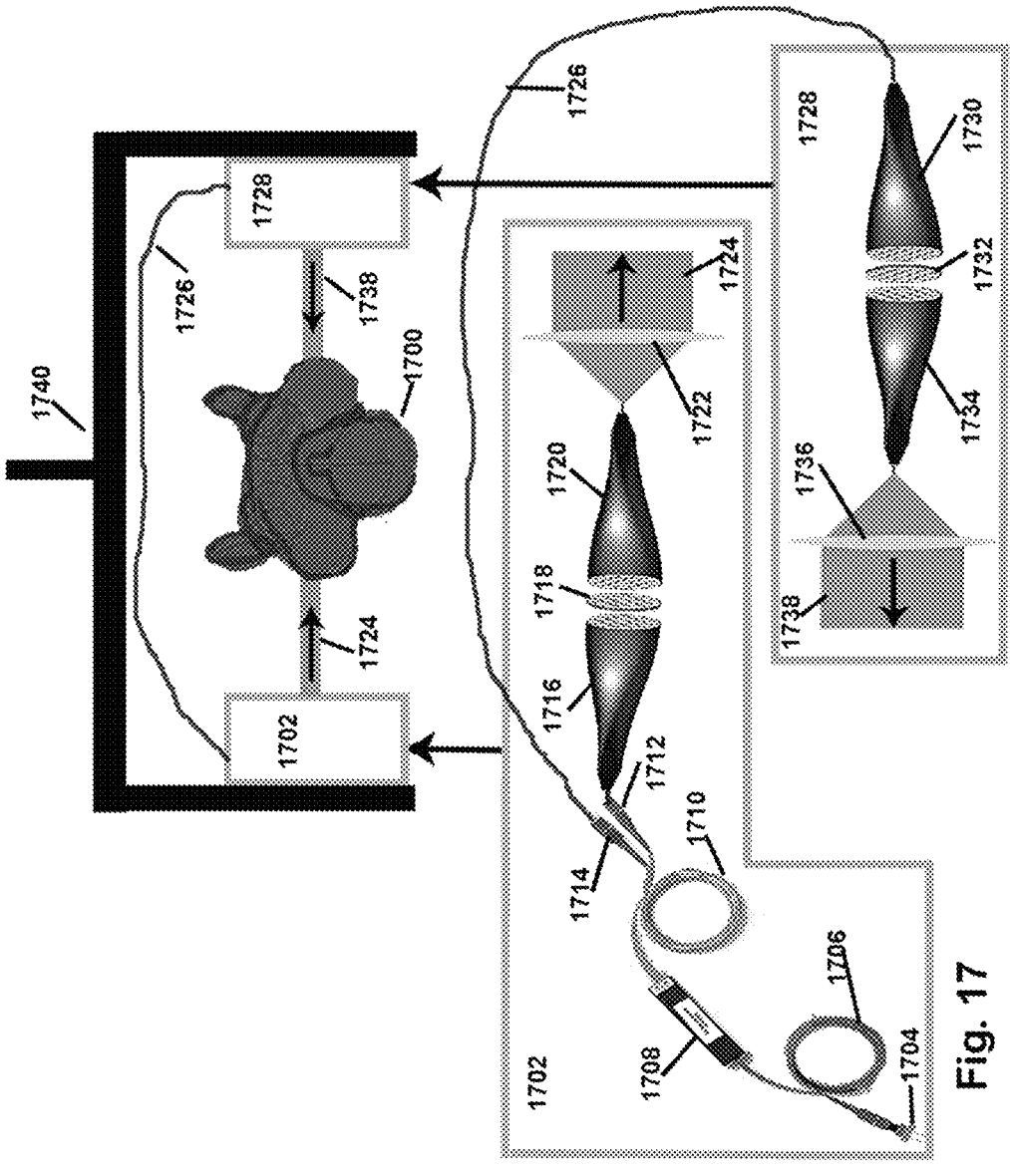
FIG. 17 is a diagram illustrating another embodiment of the present invention utilizing two collinear overlapping beams.

To implement this third embodiment, several different configurations can be used. These configurations have to carry out the basic steps of:

1. Create multiple beams on each side of the patient (the designation of "each side" is arbitrary and could be replaced with "the top and bottom", or any opposing locations around the body)
2. Modulate each of the multiple beams separately, each in accordance with a defined Fourier component's parameters
3. Recombine the modulated beams on one side of the patient to form a single beam going in one direction and recombine the modulated beams on the other side of the patient to form a single beam going in the opposite direction
4. Let the beams overlap from opposite directions to form a "composite beam" producing Fourier synthesis in the space within the patient to be treated
5. Repeat along different beam paths if desired to address different areas within the patient's body as needed, using separate multiple composite beams simultaneously, or using a single composite beam in multiple beam paths sequentially, one at a time This is further illustrated in FIG. 17, which depicts the use of optical beams, such as are produced by a laser, and fiber-optics, prisms, and/or Holographic Optical Elements (HOEs). When using RF beams, such as microwaves, waveguides can be used instead of fiber-optics. FIG. 17 depicts the use of a module 1702 which contains at least one laser, which could be a fiber-optic laser built into the optical fiber 1706 or an external laser, such as a laser diode 1704 that is directed through a fiber 1706 into a 1×2 fiber-optic beamsplitter 1708. One of the output beams 1714 is directed through an optical fiber 1726 across the system mounting bar 1740 to be used in the module 1728 on a first side (the right side in the figure) of the patient's body 1700. The other beam 1712 exiting from the beamsplitter 1708 is directed into another fiber optic beam splitter 1716 which produces many output beams (as many as the number of Fourier components which are to be used). If necessary, multiple fiber-optic beamsplitters can be cascaded to produce as many beams as desired. Each beam is used to produce a separate Fourier component. The fibers are preferably single-mode, polarization-maintaining fibers. The output fibers of the beam splitter 1716 are assembled into a fiber bundle such as is shown as a representation of an array at the end of fiber bundle 1716, or are mounted into rows and columns to produce an ordered fiber-array arrangement, which will produce an array of multiple individual beams. Alternatively, an array of lasers can be used to produce the multiple-beam array instead of the components 1704-1716. Or, a single laser's beam can be expanded and collimated before passing through the modulator array 1718. Either way, multiple separate beams are produced in an array arrangement. 1718 depicts an electro-optic modulator array, with one modulator for each beam entering the modulator array. Here each beam can be modulated separately to form a beam component used to form a standing wave corresponding to one of the desired Fourier components. The beams exiting the array of modulators 1718 can then be directed into the fibers of a fiber-optic beam combiner 1720, which combines all of the beams into a single beam, while each beam within the new single beam retains its new modulation profile. The beam exiting the combiner 1720 expands and passes through collimating optics 1722, forming a collimated beam 1724 which travels to a second side (the left side in the figure) of the patient. The components 1730, 1732, 1734, and 1736 in module 1728 perform the same functions as their identical counterparts in module 1702. They produce the beam 1738, which travels to a first side (the right side in the figure) of the patient, as mentioned above. Instead of using a fiber-optic combiner (such as 1720 or 1730), a Holographic Optical Element (HOE) with high efficiency (preferably made with Dichromated Gelatin (DCG) or Photopolymer), or a prism array can be used to re-direct all beams exiting the modulator array (1718 or 1732) to a single spot, and another HOE can be used at that spot to combine all beams into a single co-linear beam.

Once a composite beam has formed (by the overlap of component beams from both directions), a patient can be moved into it to the proper position to produce the DEP within the patient at the desired location. The entire unit (1740, 1702, and 1728) can be rotated and moved around the patient as well for required positioning. As mentioned herein, multiple units can be ganged together to make simultaneous or sequential irradiation of different areas of the patient's body possible with minimum patient movement required, saving time as well. The size of the composite beam can be altered as needed to irradiate different sized areas within the body by using conventional optical techniques, such as the use of an adjustable zoom lens in each of the two opposing component beams, keeping them both at the same size.

Figure 18:
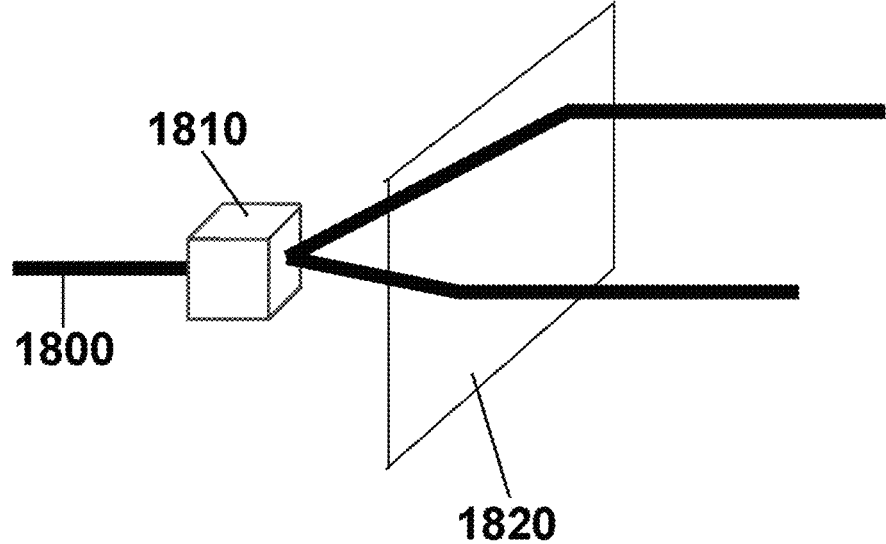
FIG. 18 is a diagram illustrating a section of an embodiment of the present invention utilizing beam scanning.

To further reduce or eliminate required patient motion during irradiation of different areas, each component beam (coming from opposite directions) can be scanned with conventional scanning components, aiming the beam at a prism array or an HOE to re-direct each beam to its new position. This way, any area of the body can be irradiated at any size without the need for patient movement. This can be seen in FIG. 18 for instance, where 1800 is a component beam (such as 1724 in FIG. 17), 1810 is a beam scanner, such as a Galvano or electro-optic X-Y scanner, and 1820 is a prism array or, preferably, an HOE which bends the beam, wherever it lands on the HOE) so that it bends and travels to the patient in the direction parallel to the initial component beam 1800.

The use of multiple units (each unit consisting of components such as 1740, 1702, and 1728) can be placed around the patient at different angles. For instance, three units can be used, each generating a DEP which is shaped like a thin disk in space, arranged so that each generated DEP disk is perpendicular to the other two generated DEP disks (each oriented parallel to either the X, Y, or Z axis). The intersection of these DEP disks will be a DEP point in space that is much more intense (using CIA, described herein) than the energy in the other areas of the generated DEPs. This high-energy point can be the only area with sufficient energy to affect body tissues in a significant way, making it possible to treat an area as small as the wavelength used, in all three dimensions. Utilizing only two such units that form overlapping DEP disks in space would produce a line, rather than a point area in space with sufficient energy for diagnosis and/or treatment. Different wavelengths can be used to form different sized DEPs and/or the beam size of one or more beams can be adjusted to address any required body area shape and size.

The point or points where DEPs are required will, therefore, contain DEPs produced by constructive interference from the Fourier synthesis, while the remaining regions in the space 1000 will contain DECs due to destructive interference. Like Bragg's X-ray microscope, each sine wave of the Fourier series is created by the interference of two waves, but the beams are in the same plane or volume as the final Fourier synthesis standing wave pattern, instead of coming from a plane outside of the final Fourier synthesis plane as Bragg utilized. Consequently, no traveling waves exist in the space outside of the space 1000 to create damage to healthy cells.

Figure 11:
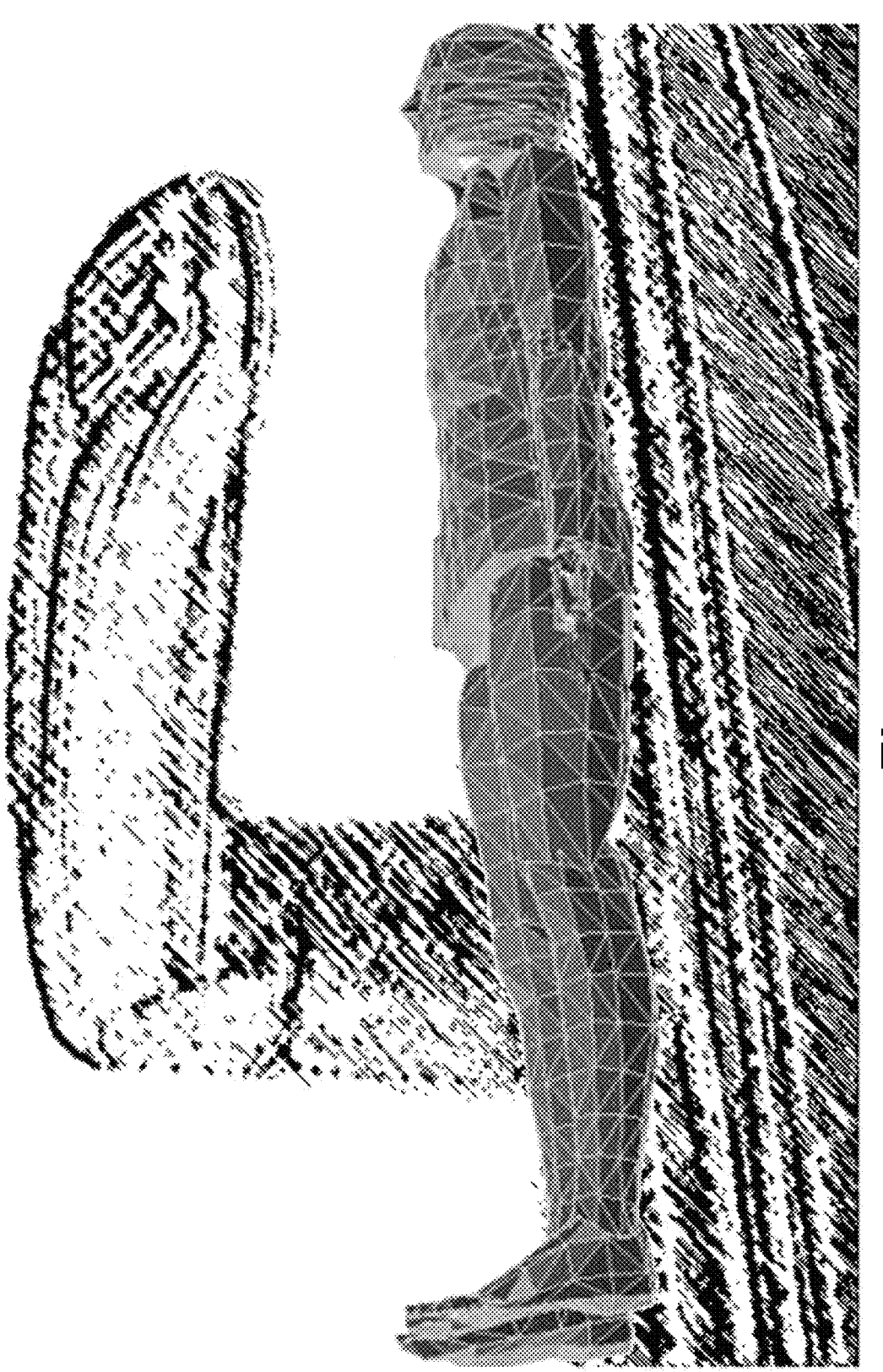
FIG. 11 is a depiction of an alternate configuration that may be utilized with an example of the present invention.
Figure 12:
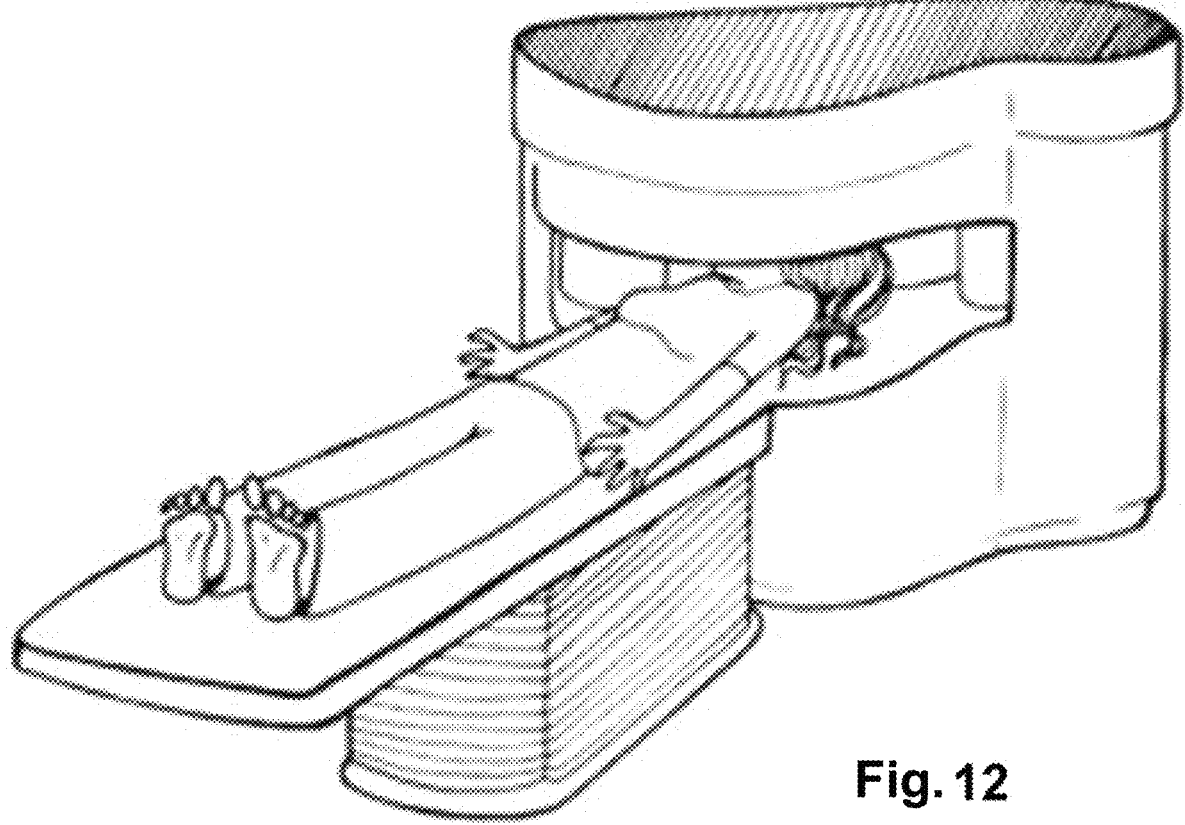
FIG. 12 is a depiction of yet another alternate configuration that may be utilized with an example of the present invention.

Unlike the arrangement of the first embodiment, which uses traveling waves of different temporal frequencies, and therefore only creates the proper pattern of DEPs and DECs for a portion of the time, the sine wave components of this and the second embodiment described above are stationary standing waves, and therefore produce the DEPs and DECs 100% of the time. Therefore, unlike the first embodiment, no bias is produced and no damage to healthy cells will occur in the regions of DECs, even with the use of extremely powerful energy beams. When used in a patient diagnosis and/or treatment system, the beams can originate from outside of the body and can have a large or very narrow collinear beam diameter, allowing for diagnosis and/or treatment of a specific point or points along that beam with a compact, open profile diagnosis and/or treatment system such as shown in FIG. 11. This simpler system, and/or the patient, can be moved to different positions at different times to treat different points within the patient, especially if the unit includes the imaging technology (as previously mentioned) to determine the coordinates of the cells to be treated. As in the other embodiments disclosed herein, many such units (as disclosed in this third embodiment) can be assembled into an arrangement such as a circle to define a circular plane surrounding a patient (as in FIG. 6), or several units can be assembled together into many circular rings around the patient to form a cylindrical diagnosis and/or treatment region as in FIG. 7, or a square, rectangular, or other shaped diagnosis and/or treatment region can be constructed such as shown in FIG. 12.

Other configurations are possible to accomplish HET. For instance, in a fourth embodiment, instead of the arrangement used in the previous embodiments, using opposing energy sources, a single composite source (as described above) can be used with a reflector to send back the opposing beam. A phase modulator alters the phase across the reflecting beam as it exits the mirror to give it the phase-front that would be produced by a separate composite source. Alternatively, in a fifth embodiment, an unmodulated reflection beam (such as from a plane reflector) can be used to produce the required sinusoidally varying beams by properly modulating the components of the composite beam to take into account that they will be reflected by a plane reflector with no further phase modulations. These fourth and fifth embodiments could also be employed in an arrangement such as the one depicted in FIG. 11.

A sixth embodiment uses two overlapping collinear beams that differ slightly in frequency. Initially they are put out of phase, creating a large stretch of destructive interference. However, the difference in frequencies will lead to the beams eventually going in phase, creating constructive interference, which will eventually go out of phase again in a further distance. Consequently, what is produced is an area of constructive interference, surrounded (in front and behind the area of constructive interference) by equally large areas of destructive interference. The length of each area is dependent on the frequencies used, the total path length, and the difference between the frequencies.

The second, third, fourth, fifth, and sixth embodiments could also be used with X-ray and gamma radiation treatment to eliminate collateral damage from X-ray or gamma ray beams entering and exiting the selected region to be treated. The more coherent the radiation, the better it is to form the desired interference pattern. Coherent X-rays can be formed, for instance, by a Linac Coherent Light Source (LCLS), which uses a hard X-ray free-electron laser source, such as the one located at the Stanford Linear Accelerator Center in the U.S. When sufficient intensities of coherent gamma rays can be filtered from broad gamma ray beams or produced by a coherent gamma ray source ("graser"), they can be used for HET as well. For instance, the process of stimulated coherent annihilation of relativistic electron-positron pairs in a strong laser field can be used if the energy of laser photons in the beam (center-of-mass) reference frame exceeds $mc^2$, and coherent stimulated generation of $\gamma$-ray photons becomes possible.

The inventions disclosed herein can be designed to work with any type of waves. This includes conventional electromagnetic, acoustic, pressure, and even matter waves. Any type of wave generator can be utilized as a source of waves for use with the present invention, while some sources will perform better than others as a function of their ability to provide a high degree of coherence, controlled directionality, etc. Laser-illuminated optical holograms provide all the necessary flexibility to accurately reconstruct waves, rays, beams, and points of light anywhere in 3-D space, with precise phase and angle information reproduction. The embodiments of the present invention disclosed herein can therefore be readily implemented in the optical regime using conventionally available lasers and optics. For instance. IR and near IR laser beams can be used to produce DEPs with a diameter on the order of 700 nm to 1 micron, providing the ability to treat or destroy individual cells (such as cancer stem cells) or their sub-components. As mentioned earlier, the fact that the beams are in a state of destructive interference until they reach the area(s) of constructive interference eliminates the problems of absorption and scattering, and thus limited penetration into the body of such short wavelength beams. The technology disclosed herein will be very useful for medical applications in the RF and X-ray frequency ranges because such waves can easily pass through the body and be made to interfere with each other as required herein.

For optimal performance, the preferred method for producing the required RF radiation patterns for use with the present invention would include the use of a holographic RF beam generator, capable of precise beam forming and radiating, preferably generating multiple simultaneous spherical or plane waves with no side lobes or higher orders. The use of plane waves, rather than point-source-derived spherical waves, although workable, would require a bigger system since each antenna (or RF lens if small spherical sources are used) would have to be as big as the patient. To be truly holographic, such an electronic RF hologram should preferably have individual real-time programmable energy emitters on the order of, or smaller than, the wavelength being emitted, and each emitter, comparable to an interference spot (called a "fringe") on a film hologram, must be capable of emitting waves of any desired phase relative to the phases of other emitted waves adjacent to it.

Many sources of RF radiation and optimized antenna configurations designed to produce directed beams with reduced side lobes could be used with the present invention.

However, the current methods and equipment utilized to generate RF waves are somewhat limited. Conventional routing and distribution of RF signals to an antenna array with millimeter-sized elements would pose significant problems to transmission line characteristics such as losses, impedance matching, higher-order modes, and the size of cables and cable connectors. With a conventional digital beamforming array, efficacy can be degraded by errors in channel synchronization arising from uncorrelated variations in amplitude and phase of the local oscillators across the array. Such errors can also arise due to nonlinearities within the digital-to-analog converter, clock-jitter, or quantization errors. In addition, inherent nonlinearities within high-power amplifiers can introduce intermixing and intermodulation, producing adjacent channel leakage. Current RF antennas can't be made much smaller and crowded closer together than they are now because that causes electromagnetic interference (EMI) between them, which makes the beam less controllable. In addition, the closer together the cables get, the heavier they get as a unit, causing heating and power loss, while thinner cables are more "lossy." Each cable also produces an electrically unbalanced current, requiring the use of a "balun" (an electronic unbalanced to balanced converter) for each antenna, taking up more space (and weight), using more power, and putting an additional limit on how small and close together the antenna array can be made. Cable connectors also have a limit as to how small they can be made.

One method of producing the required electronic RF hologram antenna system for use with the present invention utilizes an array of masers, or a single maser directed to illuminate an array of beam splitters to produce multiple beams. Each maser-produced RF beam can illuminate an RF holographic beam modulator/director, forming an array of modulator/directors, which can be placed in a circular arrangement around a patient, for instance, to produce the interference patterns required. Current progress in maser design has resulted in the production of compact room-temperature masers. For instance, in 2012, researchers at the National Physical Laboratory and the Imperial College in London produced such a maser using a new crystal made from p-terphenyl doped with pentacene which works at room temperature and doesn't require an applied magnetic field.

Figure 13:
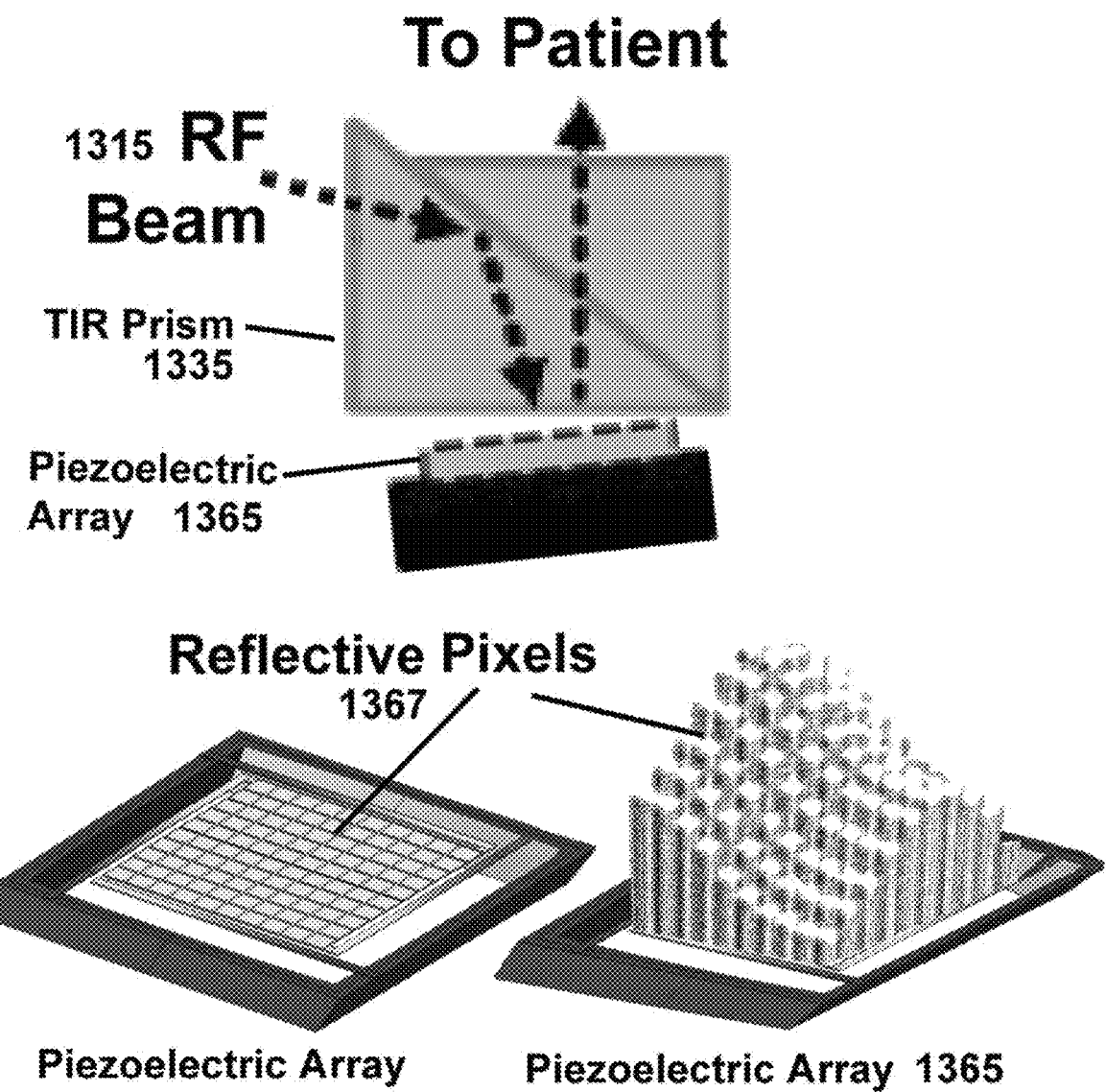
FIG. 13A is a diagram illustrating an array method that may be utilized with RF waves in accordance with the present invention.
FIG. 13B is a diagram illustrating another array method utilizing micro-mirrors that may be utilized in accordance with the present invention.
FIG. 13C is a diagram illustrating a master HET antenna system that may be used to generate coherent radio waves for use in accordance with the present invention.
FIG. 13D is a diagram illustrating a slave HET antenna system that may be used to generate coherent radio waves for use in accordance with the present invention.

One method of constructing the required holographic beam modulator/director is shown in FIG. 13A. An RF beam 1315 is sent to an RF double prism arrangement 1335 which reflects the RF beam by total internal reflection (TIR) onto a microelectromechanical system (MEMs) device 1365 at normal or nearly normal incidence. The prism 1335 can, for instance, be made from the same material used in a Luneburg lens, which refracts RF waves. This new device 1365 will alter the phase and angle of the beam reflected from each pixel in the pixel array 1367 of the MEMs device, which then illuminates the patient's ROI. The pixels in array 1367 can be made at a size which is on the same order as the RF wavelength being used, or even much smaller for higher resolution beam formation and control. One type of MEMs device can be made from an array of piezoelectric actuators, such as the kind used in inkjet printers, autofocus lens adjusters, and precise patient movers within MRI and CT scanners. Each actuator pixel in array 1367 within the MEMs device 1365 can be made of materials such as quartz, ceramic, lithium niobate, lithium tantalate, barium titanate, barium sodium niobate (often called banana), or a polymer such as polyvinylidene fluoride, which produces a very large displacement effect with a given voltage, as compared to quartz or ceramic. As a voltage is applied, the actuator pixel elongates in the direction parallel to the reflected beam, or contracts as the voltage is decreased. Stacking several actuators under each pixel reflector multiplies the travel distance of the actuator for a given voltage. The surface of each pixel in array 1367 is metallized, making it highly reflective to the RF waves. As the actuator expands and contracts, the beam reflected from the pixel face undergoes a relative phase shift. Consequently, with a complex voltage pattern applied to an array 1367 (as depicted in the bottom right of the figure), these pixels can provide a complex phase profile across the entire reflected beam, just as a light beam would when reflecting from a reflection hologram recorded on film. Other types of actuators could be used as well. For instance, an array of solenoid actuators, driven by individually addressed electromagnetic fields, could be used to accomplish the same end.

Alternatively, as shown in FIG. 13B, another type of MEMs device, such as a DMD spatial light modulator 1366, which consists of hundreds of thousands or millions of 10-micron sized mirrors 1377, for instance, (larger sizes can be used as well), only two of which are shown, that oscillate between two different angular positions, can be used in a new way. The present inventor proposes a modification of this device by combining it with a modified version of the previously described piezoelectric actuator 1388 to provide a capability to stop the mirrors at any desired position between its current two extremes. This will allow for the independent change of angle of the beam coming from each pixel over a wide range of angles, without the need to produce a phase delay between neighboring pixels, which requires more pixels to produce an overall angular shift. This can be accomplished by mounting a piezoelectric actuator 1388 under each spring tip 1399 located under each movable corner of the DMD mirrors 1377. This way, when the DMD mirror 1377, which normally works only as a two-position device, flips to one position or the other, it will land at a chosen elevation, limited by the programmable elongation of the underlying piezoelectric actuator 1388, providing programmable specific angular position control of the mirror 1377 and its reflected beam. With either proposed device (as depicted in FIG. 13A or 13B), the RF beam would preferably be pulsed to avoid the production of a continuously moving beam during changes between one desired set of pixel positions and another.

A preferred method of producing an electronic RF hologram antenna system to be used with the present invention to create EM constructive and destructive interference as needed within a patient, includes the use of a transmitter (Tx) antenna array based on a system developed by Dr. Dennis Prather et al. at the University of Delaware in Newark, Delaware. Their system was developed for future 5G cellular communications networks, with 10 Gb/second capability. Such antenna systems are under development at Phase Sensitive Innovations, Inc., also in Newark, Delaware. The Prather system solves the problems delineated herein above by generating precise phase-modulated laser beams that are controlled in real time, and simultaneously down-converting the laser beams to RF waves that mimic the laser light's phase and amplitude characteristics, forming a spatially-coherent phased-array feed network. The system includes an analog front-end to minimize quantization errors and nonlinearities, while offering agile digital beamforming with a flat phased-array antenna form factor that preserves spatial coherence across the entire array. Employing small tightly coupled dipoles in a phased array provides an ultra-wide bandwidth capability without profile issues, scan blindness, or complex balun operation. This profile embodies a "current sheet array" design, originally proposed by Harold Wheeler in 1965, which most closely approaches an ideal continuum of amplitude and phase-controllable radiating elements. The implementation of a dense feed network, necessary to drive the antenna array holographically, has previously been hampered by bulky and complex impedance matching components. The Prather system solves this problem by relying on the extensive use of a fiber-optically fed, tightly-coupled array, using polarization-maintaining fiber optics between most or all optical components.

Although this design could be used with the present invention, the present inventor proposes an alternate optical feed technique that doesn't require fiber optics, is simpler, more compact, less bulky and heavy, and easier to manufacture. Use of the Prather technique for this purpose is within the scope of the present invention.

In either case, high-powered, high-linearity photodetectors (such as with a die size of 0.5 mm×0.5 mm) are used to convert laser light into electrical signals which power the antenna elements to produce RF radiation. Such a system has been shown to output power of over 1 W at 10 GHz continuously, with almost 40% diode conversion efficiency, and 10 W of peak power using low duty cycle pulses, with over 50% diode conversion efficiency. Arrays with up to 24 dBm of radiated power per element have been demonstrated. Such an antenna array could be configured to be placed around a patient as a source of RF energy to be used with the embodiments of the present invention for disease diagnosis and/or treatment.

This holographic RF antenna array uses millimeter-sized (~2 mm) array elements, making it capable of simultaneous multiple beamforming and real-time precise phase and ray angle control. The array uses dipole antenna elements attached to each other in a dense array configuration. To bypass EMI and other drawbacks encountered when using conventional electrical cables and baluns (used to balance electric currents at each antenna), the Prather system uses thin optical fibers (instead of electrical cables), attached to the photodiodes, that are attached directly to the dipole antennas in the array. The optical fibers have an extremely wide bandwidth (0 to 100 GHz), virtually no losses, produce no EMI, are thinner and lighter in weight than electrical cables and connectors, and need no baluns, since the optical signal is always balanced. The system uses fiber optics to allow the lasers, optics, and electronics to be located on the ground, while the flat antenna array is mounted on a tower, as required for cellular communication systems.

Since medical applications don't require such a large separation between components, the present inventor devised a method to use a more compact system with an array of phase modulators mounted directly over the photodiodes, eliminating the need for fiber optics. Preferably, this array would be addressed with an active matrix circuit configuration to minimize crosstalk. If required, a lens array can be used to maximize light collection efficiency at the photodiodes. Two "injection-locked" diode lasers are used to generate a light beam that pulses at the desired RF frequency, which is sent through the fibers of the Prather system (sent through space in the modified system presented here) and is converted to electrical signals at the antenna dipoles by the photodiodes to produce the RF radiation. Each fiber has an electro-optic modulator to allow for the modulation of the phase and amplitude of the laser's optical signal at each dipole. In the current modification proposed here, each photodiode has an electro-optic modulator. Since the antenna elements are on the order of the wavelength of the RF energy used, the array acts like a conventional film hologram (except that it is electronically changeable in real time), eliminating unwanted lobes, higher orders, and stray beams, and allowing the generation of multiple beams with precise beam steering, as well as sine wave production directed at the desired angles by the proper selection of phase shifts. However, unlike in the cellphone antenna array system application, which generates continuous travelling waves for cellular communication use, HET beams are made to produce stationary standing waves to continuously produce the desired regions of destructive and constructive interference in space. This provides the flexibility to holographically create RF constructive and destructive interference in 3-D space to deliver energy to targeted cells and/or macro-molecules within the body, while not affecting intervening healthy cells.

Figure 13C:
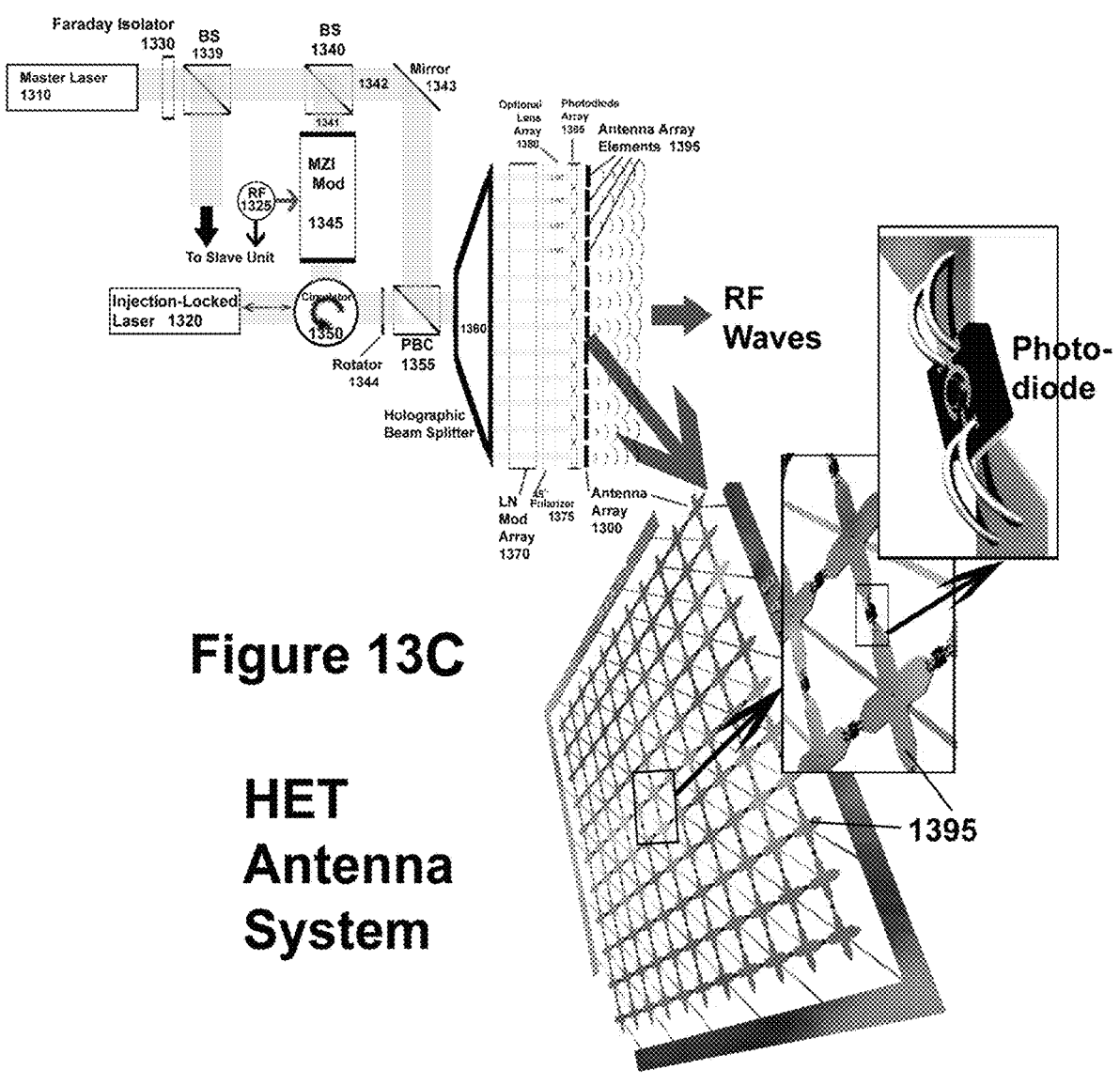

The following is a description, illustrated in FIG. 13C, of how the holographic antenna array system 1300 of the present invention can be made and used. Two (preferably diode) lasers are utilized so that one laser 1310 (the master laser) beam is injected into and seeds the second laser 1320 (the injection-locked laser), so that the beams from the two lasers are locked together. The beam from the master laser 1310 passes through a Faraday rotator isolator 1330, which prevents light anywhere in the system from reflecting back into the master laser 1310 to corrupt the desired signal. The beam is split by a beam splitter 1340. One beam 1341, exiting the beam splitter 1340, goes to a null-biased Mach-Zehnder Interferometer (MZI) modulator 1345. An additional beam splitter (not shown) within the MZI modulator 1345 creates two beams that go into the two arms of the interferometer (not shown). Both arms contain electro-optic modulators (not shown), such as voltage-controlled lithium niobate crystals. The electro-optic modulators alter the relative phases of the two beams, causing them to interfere with each other, introducing a phase modulation to the recombined beam. An RF seed oscillator 1325 controls the electro-optic modulators electrically, superimposing an RF frequency onto the beam, generating sidebands.

The first and strongest two sidebands generated are equal to the master laser's 1310 carrier frequency plus and minus the RF frequency generated by the RF seed oscillator 1325. The two beams are caused to interfere in the MZI modulator 1345 so that the master laser 1310 carrier frequency and the sideband equal to the carrier frequency minus the RF frequency are suppressed (nulled) by destructive interference. An additional optical filter (not shown) is used to help with this suppression. The remaining beam, which outputs from the MZI modulator 1345 at a frequency equal to the carrier signal of the master laser 1310 plus the RF signal, is down 20 dB from the process. This beam enters a circulator 1350, which allows the beam to exit the circulator and enter the injection-locked laser 1320, forcing it to oscillate at the same frequency as the incoming beam (at the carrier frequency of the master laser 1310 plus the RF frequency), amplifying the signal to match the intensity of the second beam 1342 exiting the beam splitter 1340. Consequently, the beam exiting the injection-locked laser 1320 oscillates with the same characteristics (linewidth and envelope function) as the master laser 1310, eliminating noise which would otherwise result from the convolution of different envelope functions that would be present if the two beams were independently generated from the two lasers 1310 and 1320. The circulator 1350 then allows the beam exiting the injection-locked laser 1320 to exit the circulator 1350 and go to a polarization rotator 1344 and a polarization beam combiner 1355. The path lengths within the circulator 1350 cause destructive interference of any light from the beam that exits the MZI modulator 1345 that would exit the circulator 1350 and go directly to the polarization beam combiner 1355, while allowing light to exit the circulator 1350 (due to constructive interference) and go into the injection-locked laser 1320. Also due to constructive interference, the path length in the circulator 1350 allows the beam from the injection-locked laser 1320 to pass through the circulator 1350 and go to the polarization beam combiner 1355. The beam 1342 coming from the beam splitter 1340 and mirror 1343 enters the polarization beam combiner 1355 and combines with the beam coming from the circulator 1350 (which came from the injection-locked laser 1320) after it's polarization is rotated 90° by polarization rotator 1344.

The beam exiting the polarization beam combiner 1355 consists of two co-linear orthogonally polarized beams of equal intensity, one at the carrier frequency of the master laser 1310, and the other at the carrier frequency of the master laser 1310 plus the RF frequency (coming from the injection-locked laser 1320). This combined beam is split by a cascading number of beam splitters 1360, such as a fiber-optic or waveguide beam splitter, (which can also be a diffractive or holographic beam splitter), producing as many beams, arranged in an array, as there are elements 1395 in the antenna array 1300. Each beam from the beam splitter 1360 goes to a lithium niobate electro-optic modulator, for instance, in an array of modulators 1370, which is followed by a linear polarizer 1375 oriented at 450 to the polarization axes of the two superimposed beams.

Each output beam 1387 from the polarizer 1375 becomes a parallel linearly polarized beam that is down 3 dB as a result of passing through the polarizer 1375. Driving the lithium niobate modulators in array 1370 alters the speed of the two orthogonally polarized beams passing through each one, relative to each other (by a factor of 10), resulting in a variation of the polarization ellipticity of each beam exiting the modulator array 1370. Each linearly polarized beam 1387 exiting the linear polarizer 1375 illuminates a photodiode in the photodiode array 1385. The computer generated electronic modulation signals sent to the lithium niobate modulators in the array 1370 directly alter the amplitude and phase of the output beams 1387 exiting the linear polarizer 1375. Consequently, the amplitude and phase of the beam 1387 coming from each lithium niobate modulator 1370/ linear polarizer 1375 combination can be independently controlled. Each output beam 1387 goes to a photodiode in the array 1385 which is connected between antenna array elements 1395. Optionally, if the diameters of the beams 1387 are larger than the photodiodes, a lens array 1380 can be used to focus the beams 1387 onto the photodiodes in the array 1385 so that no light is wasted. The bottom right-hand side of the figure shows a close-up view of the antenna elements 1395 and the photodiodes in the array 1385.

Each photodiode in array 1385 is a "low frequency" square-law detector, so, consequently, it can only react to the difference (beat frequency) between the frequencies of the two superimposed beams, which is the desired RF frequency. The base frequencies of the individual light beams are way beyond the photodetector's ability to respond to them, and so they have no effect. Each photodiode in array 1385 then creates a current, oscillating at the RF frequency, in the dipole 1395 it is connected to. This causes the dipoles 1395 to coherently emit RF waves whose phase and amplitude are independently controllable at each dipole 1395. All of the RF waves produced will be synchronized across the entire array, which would be virtually impossible to accomplish with conventional RF antenna designs and equipment. The elements in the phased array behave like a diffractive structure. By controlling the amplitude and phase of the RF signal at each element, the propagation in the far field behaves like a dynamic optical hologram field reconstruction. This allows the antenna array 1300 to behave like an RF hologram that can generate RF beams of any form, phase, amplitude, and direction desired for use with the present invention.

Figure 13D:
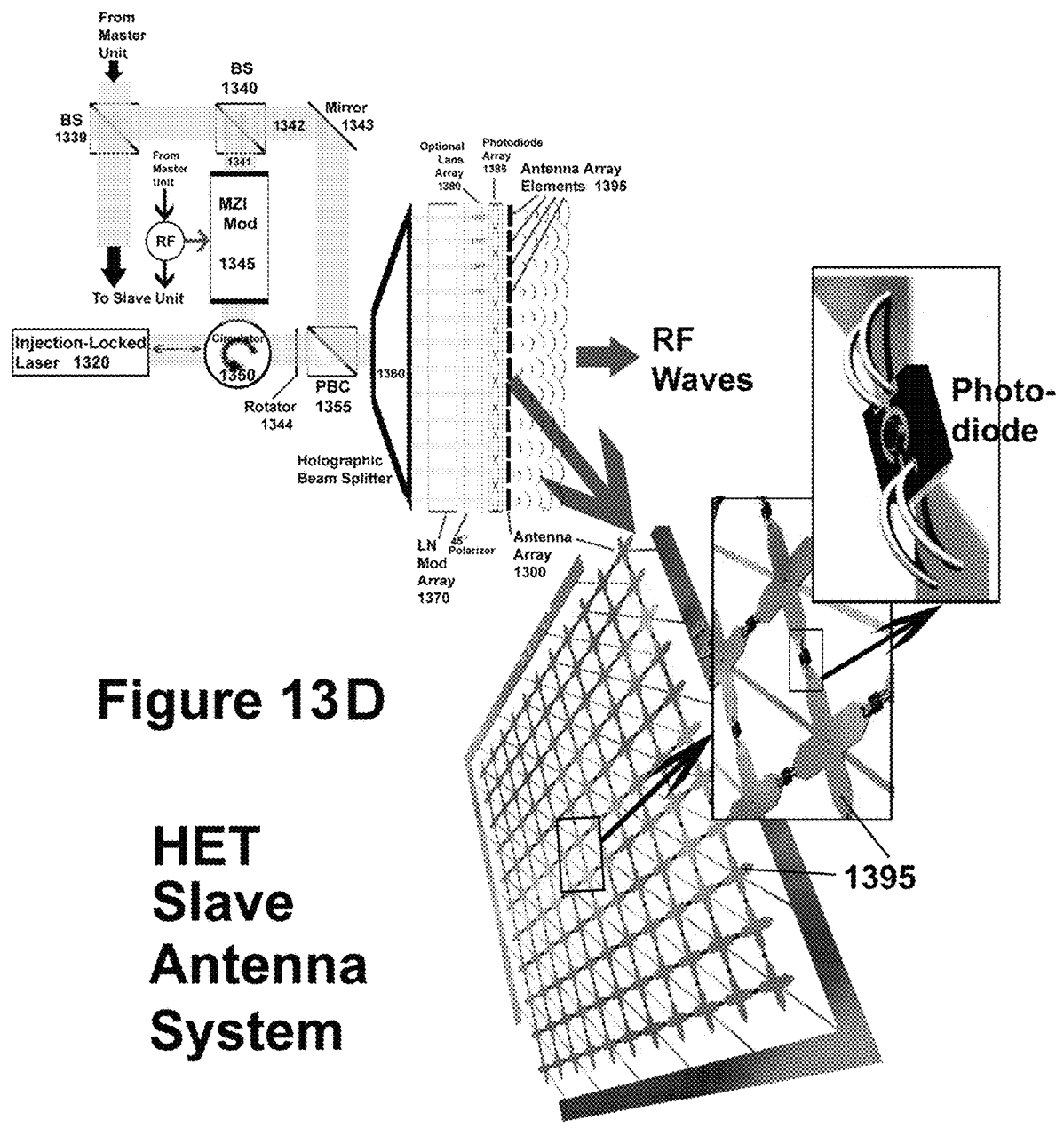

The antenna array 1300 can be either flat or curved and several of them can be arranged around a patient for diagnosis and/or treatment, for instance, such as is depicted in FIGS. 6 and 7. Although each of the several antenna arrays can work independently, noise can be suppressed by having them all locked to the same master laser and master RF oscillator. To accomplish this, an additional beam splitter 1339 can send a beam from the master laser 1310 to each "slave" antenna unit to seed the injection-locked laser in the slave unit, as shown in FIG. 13D. The RF seed oscillator from the master antenna unit can also send its RF signal to the slave units to seed the MZI modulator in the slave units as shown in FIG. 13D.

Use of a coherent-wave holographic antenna system provides the most efficient, highest-power method of RF wave generation, with a high degree of directivity, and without higher-order modes and side lobes, making the present invention highly effective. Conventional film holograms have the disadvantage of producing a zero-order un-diffracted beam and a −1 order diffracted beam, which are wasteful of energy, removing energy from the intended directions and sending unwanted energy in directions where energy is not wanted. This could be especially dangerous during medical treatment. However, since this hologram only behaves like a diffractive hologram, but is in actuality a self-luminous computer-generated hologram (CGH), with the phase of energy coming from each energy emitter 1395 controlled by a phase modulator without diffraction, it produces no zero order or −1 order radiation. The relative phase relationships between adjacent propagating beams control the formed beam angles.

Whenever beams of energy pass through a patient's body that are not in a state of destructive interference, scattering and reflection can occur at various locations due to the presence of different materials (soft tissue, dense tissue, blood vessels, blood, muscles, bone, etc.) with different characteristics (such as different indices of refraction, conductivities, etc.), and the boundaries between them. When such beam path deflections occur, the resulting potential alteration of the intended interference pattern, and the potential modification of the locations and degrees of constructive and destructive interference that may be created, can detract from the accurate production of the ideal interference effects desired. This can be compensated for since coherent waves that preserve phase information are being used in the present invention. To accomplish this correction, the present inventor proposes the use of a technique that has been developed for cellular communication networks, called "channel state estimation."

Newer cellular transmission technologies aim to transmit information intended for a particular user directly to that user, with sufficient strength and minimal interference from surrounding static and changing obstacles. Vehicles, buildings, people, and other obstacles can scatter and reflect RF signals, reducing signal strength to its intended user, and causing interference with other users. Since the user and many of these obstacles can also move, the disruptions have to be compensated for on a continuing basis. To accomplish this, the communications channel between transmitter and receiver is repeatedly monitored to determine its "state." This information describes how a signal propagates from the transmitter to the receiver and represents the combined effect of, for example, scattering, reflection, fading, and power decay with distance. This "channel state information" is checked many times a second by sending out a single pulse each time from a known point that is supposed to be directed only at the user and not deflected in any other directions. Receiving antennas placed at various locations around the space between the transmitter and receiver can detect the presence of unwanted stray signals, indicating the presence of scattering and reflection. This information can be used to alter the transmission pattern to specifically compensate for the scattering and reflection of the signal at any given moment.

This technology can be incorporated into embodiments of the present invention by placing receiving antennas around the patient, along with the transmitting antennas, to detect scattering and reflection as well. Fourier analysis allows for the determination of the direction and intensity of the stray signals. Armed with this information, the signal to be transmitted at the next instant of time can be altered with a negative phase and amplitude correction added to the transmission pattern to cancel the previously detected scattering and reflection by destructive interference.

Monitoring and correction can be necessary when sending RF waves to a particular point in the patient's body because, depending on what frequency is used, there can be many changes in beam paths due to patient motion, breathing, heartbeat, organ motion, blood flow changes, internal liquid and gas flow, etc. This can be accomplished at relatively low RF frequencies (such as 100-200 MHz) using conventional receiving antennas, each followed by an "A to D" converter and an I/Q receiver that captures the amplitude and phase of the RF signal, synced with a clock to get complex field information at all the points, followed by a real-time FFT (Fast Fourier Transform). Then a complex conjugate (an inverse signal) is created with negative phase and 1/amplitude as a transmission profile correction signal which is sent to the transmitting antenna to cancel out the scatter and reflections on the next transmission pulse, resulting in a single-point reconstruction at the receiving antenna.

Antennas, such as the rectangular sections composing the ring around the patient in FIG. 6, can consist of alternating transmitting and receiving antenna sections. However, with high frequencies in the gigahertz range, it is very difficult to carry out the necessary Fourier analysis to determine the intensities and directions of received beams, traveling in the wrong directions, quickly enough in real time. This can be accomplished, however, with a receiving antenna system also developed by Prather et al. at the University of Delaware, for future use in 5G cellular communications. To create a nearly instantaneous Fourier analysis, the Prather system utilizes a receiver antenna array and a method to up-convert the received RF signals to an optical wavelength, allowing for a real-time optical Fourier transform to provide the high frequency stray-beam information to the transmitting antenna in real time.

The receiving antenna system has to provide a continuum of spatially resolved and statistically independent detection points, enabling the determination of the unique locations, within an array of detector elements, that each signal came from. This operation is equivalent to an imaging process and can be realized using an up-converting phased array that relies on Fourier optics concepts to perform spatial mapping of the RF environment to a corresponding detector array.

This is equivalent to an imaging system because it literally "images" the RF scene by spatially mapping every received RF signal onto a particular detector based on its point of origin in the environment. In this process of "imaging" the RF signal environment, spatial separation is achieved, which mitigates Adjacent-Channel and Co-Channel Interference by preventing the interaction of signals originating at different spatial locations. The signals are first spatially separated onto different detectors and then individually processed as received signals, which serves to mitigate signal intermixing and intermodulation.

To realize this capability, this embodiment of this component of the present invention uses a phased array receiver system, where each element in the array is connected to an optical modulator that up-converts the received RF signal into the sideband of an optical carrier. After this collective up-conversion, the optical signals are gathered into a common fiber bundle (where the location of each fiber corresponds to the location of the antenna element to which it is connected in the array). The sidebands are filtered off of the carrier and launched into free-space to allow for all of the optical beams to overlap where they are subsequently "imaged" with an optical lens onto a photodetector array, with each photodetector corresponding to a unique spatial direction. The optical lens produces an optical Fourier-transform making it quick and easy to spatially process the complex RF signals over the entire array-antenna aperture. By using an optical Fourier transform lens, all of the spatial processing on the up-converted RF signals is performed simultaneously and virtually instantaneously in real time without the use of an analog-to-digital converter. In so doing, the system becomes a spatial processor for a near continuum of RF beams that literally performs an analog Inverse Fourier transform at the speed of light with a potentially unlimited beam-bandwidth product, allowing for the spatial processing of all the RF waves in the RF environment.

This system is depicted schematically as well as in an image diagram format in FIG. 14. At each antenna element 1410 there is a low-noise amplifier whose output is connected to an integrated Mach-Zehnder Interferometer (MZI) modulator, forming an array 1420. A laser 1430 produces a beam with an optical carrier frequency that is modulated with the incoming RF signal from each antenna element 1410, producing an up-converted signal with sidebands from each antenna element 1410. After modulation, the up-converted signals are conveyed through optical fibers 1440, which are lightweight, low-loss, and have been precisely measured and spliced to match the total path lengths in all channels. Subsequent to the optical fibers, the signals pass through an array of low-speed optical phase modulators 1450 that are custom fabricated on a single lithium niobate photonic integrated circuit board. This modulator array is used to apply phase biases to the channels individually, as well as to compensate in real time for the random phase variations induced by acoustic, mechanical, and thermal perturbations of the loose optical fibers. The means of detecting and correcting for these phase variations is implemented as part of the free-space optical processor. In this manner the sideband light emerging from the fiber array 1440 replicates the RF field at the antenna aperture, scaled up in frequency, but down in size.

Carrier suppression is achieved by the use of optical bandpass filters (not shown). In addition, the carrier light is directed via a polarizing beam splitter 1470 into a lens 1480 that generates an image of the fiber array, magnified such that each fiber is imaged onto a separate photodetector in a commercial photodetector array 1490. The respective image of each fiber is overlaid with a large collimated spot derived from the same laser that feeds the up-conversion modulators 1420. Being from the same laser, and arriving at the linear photodetector array 1490 after traveling through a closely matched length of optical fiber, this laser mixes with the focused spots from the reflected carrier light in each fiber, with each photodetector in the array 1490 capturing the beat between each separate signal channel and the common reference signal from the laser spot.

The outputs of these photodetectors 1490 are used to measure and compensate for mechanical/acoustic phase variations within the fiber feed network in real-time (200-kHz refresh rate). While the reflected carriers are used to spatially phase-lock the array, the light from one sideband passes through the optical bandpass filter 1460 and continues to propagate into free-space 1495. In so doing, the contributions from each fiber from all the array elements 1440 overlap as they propagate and expand in the free space 1495. At this point, a lens 1496 is used to perform a spatial Fourier transform on the optical field in the lens aperture thereby yielding an image of the sideband energy that replicates the RF scene.

The optical Fourier Transform is incident on a camera sensor 1498 that generates an image which can be used to display where RF energy is coming from, i.e., the angle of arrival or spatial sector, as well as the apparent magnitudes of the imaged sources. The use of this type of antenna system with the present invention will allow for the detection of stray beams, allowing for their cancellation. That will allow for the production of the desired interference pattern for HET with electromagnetic or sound waves, regardless of the scattering profile of the patient or object being teleported to.

As mentioned, herein above, this technology can be applied to any type of waves. To utilize it with acoustic waves, instead of EM waves, acoustic transducer arrays would replace the RF modulating arrays described herein.

Detecting and Treating Disease with HET

This patent is primarily concerned with HET and its use in diagnosis and/or treating disease. HET can be used to directly affect cells and molecules within the body without affecting or damaging surrounding or intervening cells. Hyperthermia (heating of cells) is a well-established method of treating various easily accessible diseases. However, the majority of tumors or other diseased cells are not easily accessible. HET makes hyperthermia treatment of disease possible within the body, including in areas that are not very accessible. Although the techniques using energy to diagnose and treat disease within the body, described herein above, can have a strong desired effect on cells and molecules down to a very small (mm) scale, in many instances, targeted diagnosis and treatment may need to be done on a microscopic, or sub-microscopic scale (such as in the detection and eradication of selected cancer stem cells, for instance). In addition, precision may need to be increased when directing energy to an exact cellular or other location. With conventional methods, however, it is often difficult to locate the exact cells or molecules that need to be treated. Furthermore, using the present invention to detect or treat sub-millimeter sized cells and molecules also requires the use of sub-millimeter energy wavelengths, which don't penetrate the body well. To help with finding and treating such small cells and molecules with greater accuracy, nano-technology, using nanoparticles, can be used with the present invention. Their use can make the areas of heating (or other energy effects) much finer and more precise. The proper use of nanoparticles can convert the teleported energy to heat or generate other effects efficiently, which can be used to accomplish various microscopic and sub-microscopic tasks such as clustering nanoparticles, heating and damaging tumor or other diseased cells or other structures, releasing chemicals, such as chemotherapy or genetic therapy, or triggering some other specific reaction within the body, such as the inhibition or firing of one or more neurons, or the release of enzymes or hormones, for example. Using hyperthermia with nanoparticles injected into accessible tumors has proven to be a very effective method of selectively killing tumors without harming healthy cells. The use of nanoparticles concentrates the detection ability and treatment effects to a nano-sized area even if the area of HET heating may be much larger, such as on the order of millimeters or larger. To be most useful with HET, the nanoparticles used should contain at least one material that is very strongly affected (such as absorption of energy causing heating, for instance) by the wavelength of energy being used. Various metals are best at absorbing various RF frequencies, for instance, while various light-absorbing dyes are best at absorbing different frequencies of light.

Hyperthermia

Ever since the 1960s, several researchers, including the present inventor, recognized and began exploring the unique potential of the above-described drug-free treatment technique, called hyperthermia, to kill cancer and other diseased cells, to damage proteins and cell structures to shrink tumors, and to treat or cure various other diseases. Perfecting the use of this method would be safer and potentially more effective than radiotherapy or chemotherapy and could also be used with chemotherapy and radiotherapy to enhance their effectiveness.

Hyperthermia, which raises the temperature of cells beyond their recoverable threshold, has been used to treat diseases, including cancer, since ancient times (as early as 3000 BC). It has been known that heating of the human body has a curative effect, destroying many pathogens and diseases. The body normally generates a fever to kill bacteria and viruses while healthy cells are unaffected or soon recuperate from the effects of the heating. Localized hyperthermia temperatures in excess of 43° C. have been conclusively shown to be an effective treatment to eliminate cancerous tumors, even receiving FDA approval in 1984. What's more, primary malignant tumors have poor blood circulation which makes them more sensitive to temperature changes, helping hyperthermia to be more effective in destroying them, Recently, it was discovered that heating tumor cells releases thermal shock proteins onto their surfaces, activating the body's indigenous immunologic system by allowing T cells to recognize tumors that they normally can't see. Consequently, hyperthermia also helps to kill tumor cells by boosting the body's immune system. Hyperthermia has been performed using several different methods including hot baths, wax encasement, induced fevers, local perfusion of extremities with heated chemotherapeutic agents, diathermy, radio-frequency heating, microwave heating, and ultrasound heating.

However, the reason that hyperthermia has not proved to be a panacea for the elimination of cancer lies in the difficulty of selectively applying just the necessary amount of heat only to diseased cells, while leaving healthy cells unheated or not heated too much, and intact. While cancers or other diseased cells that are readily accessible are easy to kill with externally applied hyperthermia, all forms of external heating of internal tumors and other cells results in a heat gradient within the body, heating healthy tissues over wide areas with negative results. In addition, temperatures attained at different tissue locations vary uncontrollably, based on varying tissue densities and other properties, and vary unpredictably with longer dosage times.

The effectiveness of hyperthermia treatment is related to the temperature achieved during the treatment, as well as the length of treatment, and cell and tissue characteristics. Hyperthermia works best when the area being treated is kept within an exact temperature range for a precise period of time. However, due to regional differences in tissue charac- teristics, higher temperatures may occur in various spots. This can result in burns, blisters, discomfort, or pain. It is difficult to accurately measure the temperature inside a tumor and in various heated healthy tissues, and keeping an area at a constant temperature without affecting nearby tissues can be very difficult. In addition, not all body tissues respond the same way to heat since some are more sensitive than others. To try to ensure that the desired temperature is reached, but not exceeded, attempts have been made to monitor the temperature of the tumor and surrounding tissue throughout hyperthermia treatment. Using local anesthesia, small needles or tubes with tiny thermometers (probes) have been inserted into the treatment area to monitor the tem- perature. Imaging techniques, such as computed tomogra- phy (CT), may be used to make sure the probes are properly positioned. These temperature sensors help to enable the treatment to be adjusted to keep the produced temperature within the desired range, but they are invasive and uneven heating can't be eliminated. More recently, magnetic reso- nance imaging (MRI) and CT scans have provided a newer way to monitor temperature without putting in probes.

The ability to teleport energy to nanoparticles can have scores of practical medical applications such as the treat- ment and cures for many diseases and medical conditions such as atherosclerosis, Alzheimer's disease, obesity (lead- ing to diabetes, heart disease, heart attack, stroke, high blood pressure, and obstructive sleep apnea), benign inoperable tumors, genetic disorders, spinal stenosis and herniated disks, brain disorders (psychological disorders, depression, anxiety, PTSD, eating disorders, sociopathic behaviors, and Parkinson's disease), bacterial, fungal, viral, parasitic, and prion infections, infertility, erectile dysfunction, enlarged prostate, cellulitis, and cancer.

In current clinical regional RF hyperthermia practice, MR Thermometry (MRTh) is beginning to be used for spatiotem- poral monitoring of temperature and treatment efficiency. RF transmission used for MR is commonly performed at a frequency of about 63 MHz (with a magnet strength of 1.5 T), and RF transmission induced heating is achieved with RF antennas usually driven at around 100 MHz. The RF wavelength at 100 MHz is approximately 33 cm in brain tissue (different tissue densities can change the wavelength of applied RF waves), which is not suitable to focus the electromagnetic (EM) energy selectively enough to brain tumors with a tumor size of only a few centimeters. Higher RF frequencies (>100 M Hz) are more suitable to be applied in the head and neck region to perform localized RF hyper- thermia. Unfortunately, established systems still lack the ability of non-invasive 3-D temperature measurement to monitor and control the thermal dose applied in the treated region and in healthy tissue. Realizing this challenge, experiments have been done which demonstrated that ultra- high magnetic fields (with a magnet strength ≥7.0 T) render an integrated applicator feasible. They include a configura- tion suitable for MRI, with MRTh, and controlled targeted RF heating utilizing a single transmission frequency of 300 MHz. The applicator employs the proton MR frequency for targeted R F heating and can be used together with com- mercially available MR systems and multi-channel RF trans- mission configurations for imaging diagnostics and for RF hyperthermia applications. Early results indicate that is approach is conceptually appealing for a therapeutic appli- cation to intracranial lesions since pre-treatment diagnosis and planning, thermal dose treatment control and adaptation, and post-treatment evaluation of the treatment efficiency can be performed with a single device. Applicator designs have been proposed which are capable of utilizing even higher RE frequencies (up to 1 GHz). This approach holds the promise of providing an effective reduction of the achievable thermal treatment hotspot size. To meet this goal, electromagnetic field (EMF) simulations have been performed in a human voxel model deduced from a healthy volunteer, RF antenna designs have been presented for 300 MHz, 500 MHz and 1 GHz, which correspond to 700 T, 11.7 T and 23.5 T magnets with an effective wavelength of approximately 13.5 cm, 8.6 cm and 4.5 cm in brain tissue.

Adequate phase-amplitude steering is essential to opti- mize tumor heating while minimizing treatment-limiting hot spots. Although clinical results are somewhat encouraging, the pursued optimal thermal dose of 43° C. for 1 hour is often not achieved due to formation of these treatment- limiting hotspots in normal tissue, which impede further increases of total power. Since there is a clear thermal dose-effect relationship, clinical outcomes could be improved further if power-limiting hotspots could be pre- vented, while allowing for increased power (a goal of the present invention).

To reduce such hotspots, "active treatment control" is used, which is highly dependent on reliable temperature information being available during hyperthermia treatment, as well as on good spatial power control to optimize the temperature distribution, Temperatures are usually measured by a small number of minimally invasive thermometry probes, but the sparse irregular sampling of temperatures doesn't provide adequate characterization of the actual 3-D temperature distribution, Non-invasive thermometry (NIT) obtained from MRI or CT scans can be very useful for providing more insight into the necessary treatment adjust- ments needed to obtain better quality heating, but NIT is not yet widely available and is currently restricted to a limited number of tumor sites (for instance, NIT is presently not feasible for moving tumors such as in the lungs or the abdomen, or for heterogeneous tissues).

Spatial power control depends on the number of antennas and the operating frequency. The larger the number of antennas and the higher the frequency, the better is the steering control. A higher frequency also provides a smaller focus volume, but is associated with a lower penetration depth and, hence, a larger number of antennas is needed for adequate heating of deep-seated tumors. If more power could be used, without producing collateral damage (a goal of the present invention), penetration depth could be increased, even at higher frequencies, which would provide more tightly focused hyperthermia treatment spots. More- over, the large number of degrees of freedom, resulting from the adjustability of the amplitudes and phases of the signals from the individual antennas, makes it very difficult for the operator to determine the optimal steering strategy by intu- ition or trial and error.

To help with that determination, "tissue segmentation," which attempts to classify tissue types and properties in different tissue segment locations, is a very important aspect of hyperthermia treatment planning. Dielectric properties, which determine the energy absorption in tissue, vary significantly between different tissues and organs in the human body. Thus, tissue segmentation strongly influences the treatment planning, Segmentation is based on a CT or MRI scan in the same position as is used during the hyperthermia treatment, and can be performed manually or semi-automatically. The advantages of MRI data over CT data are the very good soft tissue contrast information provided and the absence of an additional radiation dose to healthy tissues. The tumor target region has to be outlined manually to allow comparison of different treatment plans in terms of target coverage and thus treatment quality. HET eliminates virtually A potential hotspots by teleporting energy to a very small area within the body, centered around the cells or nanoparticles to be heated.

The concept and goal behind hyperthermia with nanoparticles is to send less energy into broad areas of the body than is used for dielectric heating of nanoparticles to minimize the heating of healthy tissues, while allowing energy to concentrate in the nanoparticles placed within the tumor or other diseased cells to heat them up, Being conductive, rather than dielectric, the nanoparticles will heat up more than the human tissues, with the application of less energy.

Induction heating of nanoparticles to kill cancer has been successfully demonstrated many times by multiple researchers in animals in several preclinical studies. For instance, Dr. Joseph Panzarino et al. at Corning (U.S. Pat. No. 4,323,056) injected ferromagnetic nanoparticles of >50 nm in size, composed of magnetite crystals ($Fe_3O_4$) embedded in a bio-inert phosphate-based glass-ceramic substrate, directly into tumors in mice to kill the tumors. The use of an alternating magnetic field of 700 Oersteds at the relatively low frequency of 10 KHz created sufficient hysteresis hyperthermia heating (providing the "required minimum" 1 watt per gram of tissue) to kill the tumors, while not producing any detectable unwanted hotspots in healthy issues, and not even any perceivable ill effects (from nerve or muscle response) when applied to the hands of human volunteers for "irritation" tolerance testing. This selection of low frequency was also made to eliminate any danger of electrical shock, cardiac arrhythmia or arrest, seizures, or central nervous system dysfunction. Keeping the frequency at or below 10 KHz minimized dielectric and eddy current heating of healthy tissue (in mice) while maximizing hysteresis hyperthermia heating of the nanoparticles and attached tumor cells. To prevent the temperature of nanoparticles, and consequently, the surrounding tissue, from increasing too much, they used nanoparticles with a carefully selected "Curie temperature" that matched the desired tumor treatment temperature. Continual electromagnetic hysteresis heating virtually stops automatically once the nanoparticles reach their Curie temperature, preventing overheating. This is because randomizing forces from thermal motion become stronger than the magnetic alignment forces that cause heating. In their follow-on patent (U.S. Pat. No. 4,574,782), they determined and plotted various frequency and field strength combinations that will also produce the same desired 1 watt/gram for tumor destruction with nominal dielectric or eddy current heating or other unacceptable irritations or negative effects. For instance, a magnetic field strength from 200 down to 20 oersteds can be used with frequencies of 10 KHz up to 600 KH z, or 40 Hz or less can be used with 2000 or more oersteds, for the same effects.

More recently, work at Dartmouth-Hitchcock Health Sciences by Dr. Jack Hoopes et al, with cancerous oral tumors in a couple of dogs (which were given up on by their veterinarians), has shown complete eradication of their tumors after being anesthetized and subjected to AC field hysteresis hyperthermia heating of 100 nm iron oxide nanoparticles in the range of 150-160 KHz, with a field strength of 350 oersteds, which produced 3 watts/gram in the tumors. The nanoparticles were directly injected into strategic quadrants of the oral tumors and then heated electromagnetically. The treatment was considered completely successful, allowing the dogs to eventually die of old age rather than from cancer. No chemotherapy or radiotherapy was needed. This procedure was successful because a sufficient quantity of nanoparticles was able to be injected directly into the accessible tumors. It is not known, however, if the increased animal size, and consequent increased power density, produced any unwanted dielectric or eddy current effects since the animals were fully anesthetized during treatments, and human volunteers were not used to test "irritation levels."

Consequently, to assist with specific medical diagnosis and treatment applications, this patent discloses the use of HET to directly interact with diseased cells or nanoparticles. For disease treatment, the nanoparticles display the location of tumor cells during a scan, and then, using the diseased cell coordinates, the teleported energy can raise the temperature of the diseased cells just the right amount to initiate one or more processes such as apoptosis (programmed cell death) or necrosis (externally caused cell death), or vaporization where needed.

Maximizing Hyperthermia Efficiency with Resonant Frequency Excitation

In addition to the steps outlined herein above, additional measures can be taken to maximize the energy absorbed by the nanoparticles and re-emitted as heat, while minimizing any exposure of healthy cells to energy. Consequently, to further maximize nanoparticle heating, while minimizing the amount of energy needed to be sent to the nanoparticles, the electromagnetic energy frequency to be chosen is best at the optimal frequency for absorption by the cells or nanoparticles used. Just as a wine glass can be shattered when exposed to a sound at the proper frequency (called the "resonant frequency"), a cell or a nanoparticle can absorb the maximum amount of EM energy and release the maximum amount of heat by electromagnetically "vibrating it" at its resonant frequency. Actually, the precessions of the cells' atoms' or nanoparticles' electron spins have to be made coherent, parallel, and in phase with each other, and then flipped together to a perpendicular axis to accomplish this. This technique is analogous to "lasing," the process by which a laser uses a resonant cavity to produce coherent, in-phase amplified radiation (the laser beam) which is much more powerful than a conventional incoherent light beam. This can be accomplished with a process which, when used with metallic nanoparticles, is referred to as "FerroMagnetic Resonance Heating" (FMRH).

In 2000, Christian Kirsten et al. proposed using this technique to heat up a heat-activated adhesive layer containing conductive particles to efficiently attach or detach a label to or from a surface, or bond (or de-bond) two materials together (or separate them), using microwaves, by heating up only the adhesive layer without heating the label or the surface it attaches to (or the two bonded materials). He suggested that this could be done with metallic, magnetic, ferrimagnetic, ferromagnetic, antiferromagnetic, or superparamagnetic particles, which may, for example, be selected from among aluminum, cobalt, iron, nickel or the alloys thereof, metal oxides of the type of barium hexaferrite, n-maghemite ($y$-$Fe_2O_3$), n-magnetite ($Fe_3O_4$), or ferrites of the $MeFe_2O_4$ type, wherein Me is a divalent metal selected from among manganese, copper, zinc, cobalt, nickel, magnesium, calcium, and cadmium. He further suggested that the preferred particles would be superparamagnetic nanoparticles (less than 20 nm in diameter) made from magnetite. He stated that the existence of the FMRH phenomenon had been known since 1946 but no systematic investigation of possible industrial applicability had hitherto been made. A great deal of experimentation and analysis was done and published on the study, explanation, and quantification of the phenomenon in the 1960s by various researchers. FMRH occurs when such particles are placed in a static DC magnetic field (to align their electron spin precessions) and then irradiated with an oscillating EM field, for instance, at a microwave frequency, in a direction approximately perpendicular to the DC magnetic field, to flip the precession axes. The exact frequency required to create FMRH is dependent on the characteristics of the particles being heated and the strength of the DC magnetic field. For any given particle makeup and DC magnetic field strength, the resonance frequency is very specifically set, and only that frequency will cause efficient absorption of the oscillating magnetic field energy, resonance, and very efficient heat radiation. This type of heating is much more efficient than hysteresis heating, which results from the eddy currents and dielectric heating produced by EM oscillations, usually at lower frequencies. With such high frequency EM oscillations, the particles absorb the energy at their surfaces (called the "skin effect"), preventing the formation of eddy currents in them. The absorbed energy causes coherent simultaneous heat emission from the flipped electron spins within the particles as long as they are in a static (DC) magnetic field. Consequently, much less energy is needed to provide a large amount of heating as a result of high efficiency energy absorption and high efficiency heat generation from the FMRH effect. Another important advantage of FMRH is that a gradient (spatially varying), rather than uniform, static DC magnetic field can be used, and only the segment of particles located in the gradient area with the proper field strength (given the material properties and oscillating field frequency) will go into resonance and generate heat, while all surrounding areas will remain unheated. This provides a way to generate heat in small selected areas only, with pinpoint accuracy, which is not possible with hysteresis heating.

In 2010, Noboru Yoshikawa et al. conducted experiments which demonstrated that $Fe_3O_4$ particles, on the order of a few millimeters in diameter, that were heated by FMRH using microwaves, showed a temperature gain of 50° C. and that no hysteresis heating was detected, confirming the high efficiency heating was due to FMRH alone.

In 2005, Gang Wang et al. proposed that superparamagnetic nanoparticles could be used with FMRH to produce high efficiency targeted damage of cancerous tumors, although they never tried it on an actual tumor (due to a lack of funding). They proposed using lower RF frequency electromagnetic oscillations (rather than microwaves), which the body is mostly transparent to, between 100 and 200 MHz, and nanoparticles made from maghemite (y-$Fe_2O_3$) based compounds, or yttrium iron garnet ($Y_3Fe_5O_{12}$) based compounds. Using an adjustable gradient static DC magnetic field and an energy source configured to deliver a perpendicular oscillating electromagnetic field at RF frequencies, they contemplated that first the RF power would be sufficient to cause conventional hysteresis heating of the tumor (and the surrounding area), heating it up to 42° C., while FMRH would then further heat only the nanoparticles, and thus, the tumor itself, an additional 3° to 5° C., leading to apoptosis (programed cell death), or, alternatively, an additional 7° to 10° C. leading to necrosis (cell death by ablation). By using two or three perpendicular magnetic gradients and shifting the static DC magnetic field gradients in space over time, and thus, the area of FMRH, tumor cells could be destroyed in one slice (plane), or even one voxel, at a time, eliminating the need to heat broad areas. Although they realized that attempts to infuse nanoparticles into tumors by systemic injection only produced a concentration of nanoparticles in tumors of less than 1%, they calculated that such a low concentration of nanoparticles would still produce sufficient heat to kill tumor cells due to the high energy efficiency of FMRH. Their calculations indicated that heating from FMRH is potentially more than about three orders of magnitude (1000 times) greater than that which may be achieved with conventional dielectric heating. This implies that a nanoparticle volume concentration of only about 0.1% to about 1% is all that is required to achieve the differential heating described above, a concentration which is far lower than the required concentration for a Neel-heating-based hyperthermia treatment. For protection from toxicity, they proposed that the nanoparticles could be coated with materials such as pullulan, lactoferrin, ceruloplasmin, insulin, poly(ethylene glycol), and albumin, as well as yttrium aluminum iron garnet (more specifically the aluminum doped YIG) coated with an aminopropylsilane. An additional advantage obtained from the use of FMRH is that the electron-spin-resonance frequencies of the nanoparticles can be used to monitor their temperature (and that of the cells they are attached to) by using electron spin resonance (ESR) monitoring, because of the temperature dependence of ESR properties in superparamagnetic nanoparticles. Magnetization saturation, for instance, which can be detected by ESR, depends on temperature. It has been previously demonstrated in the art that such an effect may be used to measure temperature with a sensitivity of 1° C. ESR-based imaging of nanoparticles could also be incorporated into a single system that enables FMRH heating, imaging, and thermometry with the same piece of equipment, at a lower cost than conventional MRI, because ESR only requires a much lower strength magnet (about 500 Gauss) than MRI, making it less expensive than the high-strength magnet required for MRI (which typically requires a magnetic strength of 1.5 Tesla or 15,000 Gauss).

An additional advantage of the present invention is that it can be used to destroy tumor or other diseased cells without nanoparticles as well. Since such cells have different characteristics than healthy cells, such as density, electrical properties, ploidy (the number of sets of chromosomes in a cell or of special structures within an organelle (an organized structure within a cell)), etc., the resonant frequency of diseased cells themselves (without nanoparticles) is different than adjacent healthy cells. Consequently, adjusting the addressing-RF frequency can utilize resonance to selectively create heat in diseased cells with many times the intensity of heating caused in adjacent healthy cells due to RF excitation alone. This can obviate the need for the use of nanoparticles, while still providing focused heating of diseased cells with pinpoint accuracy down to the cellular level. Again, the concomitant use of HET can eliminate any heating of healthy cells. Placing sample target cells (of the same type as those in the body to be treated) in a strong magnetic field and radiating with an RF pulse can be monitored at different frequencies to find the resonant frequency of the cells to be damaged (as with FMRH and nanoparticles). Then the patient can undergo RF pulses within a magnetic field to destroy the selected cells.

Consequently, FMRH or cell-resonance heating, with HET and hyperthermia, can be used to maximize heat production at nanoparticles, or cell-resonance heating of diseased cells without nanoparticles, to maximize their heating, while minimizing the amount of energy needed to accomplish it, and to eliminate healthy cell heating.

Protecting the Body from Toxic Drugs and Protecting Drugs from the Immune System by Enabling Nanoparticles to Carry "Cargo"

Chemotherapy drugs are designed to be lethal to tumor cells (but are also toxic or lethal to healthy cells), and genetic therapy drugs can be toxic or damaging to healthy cells, and can be destroyed or deactivated by the body's immune system. However, since chemotherapy and genetic therapy have to be delivered systemically to find tumor cells wherever they are within the body, and because more than 99% of the administered therapy reaches healthy cells rather than tumor cells, many side effects, some very severe (sometimes even fatal), can occur.

However, toxic chemotherapy and genetic therapy drugs can be contained within heat-labile coated nanoparticles, keeping them from interacting with healthy cells. Nanoparticles can be designed to seek out and attach to tumor or other diseased cells (with specific vectors). Once there, several methods can be used to release the cargo. Enzymatic catalysis (the speeding up of a protein-related chemical reaction), or a reaction to the low pH within a cell (if the nanoparticle is coated with a pH-sensitive polymeric coating, i.e. a coating that degrades when exposed to acidic environments), can also trigger the release of nanoparticle cargo. Electromagnetic energy, externally applied to such nanoparticles, can generate heat and dissolve their protective coating, also providing controlled release of toxic chemotherapy or genetic therapy drugs only to tumor or other target cells. Using this stealthy method of drug delivery, only a tiny fraction of the amount of chemotherapy drugs currently administered would be sufficient to create the same lethal cell damage produced by current much-larger chemotherapy regimens. Furthermore, it would be accomplished without generating the side effects that currently occur when healthy cells are attacked by chemotherapy drugs. The scientific literature reports experimental tests of this technique, with promising results. It is essential to be able to generate sufficient heat in the nanoparticles to release the chemicals, once attached to tumor or other cells, without generating heat in healthy cells.

In one such experiment, hydrophilic (water attracting) doxorubicin (a chemotherapy drug) and iron oxide nanoparticles were encapsulated in a shell of polyvinyl alcohol (PVA). PVA was chosen because of its ability to also load hydrophobic (water repelling) paclitaxel (another chemotherapy drug). Thus, these nanoparticles contained two potent chemotherapeutics with drastically different characteristics in one nanoparticle. The drugs were released on demand with the application of heat from an external oscillating electromagnetic field. Several other chemotherapeutic cancer drugs have been similarly combined with nanoparticles including temozolomide (TMZ) and 5-fluorouracil.

Kostas Kostarelos et al. used temperature sensitive liposomes (TSL), which are tiny vesicles (bubbles) made of cell membrane material, on human melanoma cancer cells in animal studies, demonstrating significantly enhanced cytotoxic effects on the tumor cells. They utilized hCTMO1 monoclonal antibodies directed towards the MUC-1 antigen in over-expressing human melanoma cancer cells (MDA-MB-435), resulting in a moderate improvement in animal survival. In another study, a new type of such thermosensitive vesicles, based on the hybrid membrane formation between lipids (organic compounds, such as fats) and "leucine zipper temperature-responsive peptides" (Lp-Peptide hybrids), were used to encapsulate doxorubicin (DOX). This combination achieved significant tumor growth retardation compared to control mice, with no accompanying signs of toxicity, because of their longer blood circulation, resulting in good tumor accumulation.

This cargo-carrying capability can also be useful for another important type of treatment of tumor or other cells (to treat many different diseases). Since cancer and many other diseases are genetically caused diseases, even if cancer or other disease cells are all found and destroyed, the defective genes, in the deadly combinations that created the cancers or other disease, would still be present in the body and could still generate new disease. Consequently, stealthy, safe genetic therapies need to be developed and delivered as well to stop the formation of new disease, especially in patients that are genetically predisposed to forming particular diseases. Continuing studies have shown that about 200 genes in about 12 different combinations (called pathways) are responsible for most cancers. Vectors for genes and/or their links in selected combinations (pathways), could target them for hyperthermia to destroy them, or turn them on or off, as needed, to stop them from fostering cancerous cell replication anywhere in the body. Ultimately, though, genetic therapy could stop them from forming cancers or other diseases anew in patients. Biotherapeutic therapy is similar to chemotherapy except that instead of delivering small molecular drugs, biological agents such as DNA, small interfering RNA (siRNA), proteins, and peptides are delivered to tumor sites to induce cell death. In cancer, damaged DNA results in atypical protein expression, causing negative effects. Cancer may be treated with DNA delivery by replacing the defective genes within cancer cells. Alternatively, cancer therapy via siRNA works by suppressing the protein expression of damaged genes. Protein and peptide therapy, on the other hand, operate by attacking specific cell mechanisms such as by disrupting cell adhesion, interfering with angiogenesis, and/or blocking other cellular functions, leading to apoptosis (programmed cell death). In the past, delivery of biotherapeutics has shown limited success due to the immunogenicity (provoking an immune response) caused by the delivery vectors. Inclusion of biotherapeutics with nanoparticle delivery systems, on the other hand, could solve this problem since biocompatible polymer-coated nanoparticles can provide protection against inhibitive immune responses and can provide targeted delivery of these therapeutic agents.

Scientific literature reports that an iron-oxide-core nanoparticle coated with a polymer shell consisting of chitosan, PEI, and PEG was developed. Chitosan was used to provide a stabilizing biocompatible and biodegradable surface coating with active sites for the binding of PEI and PEG. PEI electrostatically binds nucleic acids and was used to load siRNA. Results showed successful intracellular delivery of siRNA to medulloblastoma and ependymoma cancer cells and the consequent suppression of a radiation resistant DNA repair protein. The siRNA-mediated suppression of this protein led to reduced tumor cell resistance to gamma rays. Heat generated by an external electromagnetic field can be used to release these payloads when needed as well.

With the discovery of numerous clinically relevant cancer genes, gene editing is becoming an increasingly relevant aspect of cancer therapy. Gene editing via RNA interference (RNAi), through small interfering RNA (siRNA) or microRNA (miRNA) delivery, peptide nucleic acids, and CRISPR/Cas technology can potentially silence any gene of interest. CRISPR (Clustered Regularly Interspaced Short Palindromic Repeats) is a family of DNA sequences in bacteria that contains snippets of DNA from viruses that have attacked the bacterium. These sequences play a key role in a bacterial defense system and also form the basis of a genome editing technology known as CRISPR/Cas9 that allows permanent modification of genes within organisms. By delivering the Cas9 (CRISPR Associated System 9) nuclease complexed with a synthetic guide RNA (gRNA) into a cell, the cell's genome can be cut at a desired location, allowing existing genes to be removed and/or new ones added.

Gene therapy is the cellular delivery of nucleic acids in order to modulate gene expression to treat disease. Gene delivery, however, can be either inefficient or dangerous. Nanoparticles with protective coatings, and their targeted release by heat generation, can solve this problem. Phenotypic modulation (the change of appearance and behavior of a particular genetic structure (the genotype) with its environment) is achieved either through gene addition, gene correction, or gene knockdown. Gene addition is generally the most common approach, and alters cell behavior by introducing genetic material and consequent proteins that are inherently missing in the host. Gene correction is less common, but growing in popularity, and utilizes technology such as "zinc finger nucleases", triplex-forming oligonucleotides, or CRISPR-Cas to alter or correct genomic sequences. Finally, gene knockdown, through RNA interference (RNAi), has received significant enthusiasm. Because of the complex nature of cancer pathogenesis and the multitude of signaling pathways involved in disease progression, isolating unique and singular molecular targets can become increasingly difficult. Often, tumor cells have altered transcription factor activity, influencing multiple pathways, which is difficult to target through small molecule drugs. Therefore, gene therapy can provide an alternative strategy for designing effective and specific therapies against cancer.

The problem with delivering such cargo and using heat to release it once it reaches its target destination is the side effects and collateral damage created by conventional methods of heat delivery to internal destinations. HET solves this problem by delivering energy directly to the proper nanoparticles located in their target cells, generating heat only at the target locations, eliminating damage to cargo molecules from the immune system and side effects and collateral damage to the patient. Consequently, properly coated nanoparticles can, thus, be used with HET to safely carry chemotherapeutic "cargo" to tumor or other disease cells for controlled release, providing enhanced chemotherapy treatment without the usual side effects. In addition, cargo carrying nanoparticles can greatly enhance the safety and efficacy of genetic therapies.

Detection and Monitoring Nanoparticles (and Cargo) to Diagnose Disease, Direct and Monitor Treatment, and Measure and Manage Temperature To maximize the accuracy and effectiveness of hyperthermia or Holothermia™, the detection and monitoring of nanoparticles within the body are very important for several reasons:

1. Injected nanoparticles that are coated with tumor-seeking vectors will accumulate in tumor cells, providing a safe, noninvasive diagnostic tool for detecting the presence of different cancers. Once nanoparticles have been injected and have had a chance to be taken up by tumor or other diseased cells, the detection of their presence by one or more scanners provides a strong indication of the presence of such cells. This method can detect very early disease, and even pre-cancers, that are not detectable otherwise, serving as an early diagnostic tool.

2. Detecting the location of nanoparticles accumulated in tumor or other diseased cells is required to generate the algorithms needed to direct energy to selectively heat only the cells containing nanoparticles by directed hyperthermia or Holothermia™ treatment.

3. Nanoparticle monitoring has the potential to provide real-time treatment monitoring of electromagnetic energy and cargo-drug delivery as well as tissue responses, thereby expediting updates to in-process treatment regimens and improving a patient's quality of life. Detection of the extent to which cargo-carrying nanoparticles are deposited in tumor cells vs. healthy cells will help to ensure sufficient delivery to tumor cells, that healthy cells receive a minimum of the cargo and heat, and that heat release and activation of cargo is minimized or eliminated in healthy cells, while being maximized in diseased cells.

4. Monitoring of nanoparticles is also required to provide real-time temperature data about heated diseased cells, as well as surrounding healthy tissue, to allow active modification of how much energy is sent to different tissue locations in order to prevent hotspots, prevent overheating of nanoparticles (which can lead to overheating of surrounding healthy tissue), and to assure that nanoparticles receive enough energy to properly damage diseased cells or carry out other desired functions. Detecting the temperature of nanoparticles can also provide information about the produced cell damage and the release of cargo.

In order to detect the location of nanoparticles in the body, the patient has to be placed within an imaging system capable of detecting nanoparticles, such as an ESR (electron-spin resonance) scanner (as mentioned herein above), SPECT (single-photon emission computed tomography) scanner, MPI (magnetic-particle imaging) scanner, PET (positron-emission tomography) scanner, CT (computed tomography) scanner, fluoroscope, MRI (magnetic-resonance imaging) scanner, or ULTRA (Unlimited Trains of Radio Acquisitions) MRI scanner or a combination of these. Since the collected nanoparticle-position data has to be used to allow precise registration with the nanoparticles during treatment, it is important that either stereotactic methods are used to correlate positional data with the application of energy, or, for more precise correspondence, that the imaging scanner is integrated with the hyperthermia or Holothermia™ treatment system in a single device. Since the patient doesn't have to be moved between imaging and treatment in that case, optimized registration between actual tissue locations and tissue images can be maintained. The use of a single system to both diagnose and treat a patient is referred to as "theranostics."

One of the simplest and most accurate ways to detect the location of nanoparticles is with an MPI scanner. Magnetic particle imaging (P) is an emerging non-invasive tomographic technique that directly detects the magnetic properties of iron-oxide superparamagnetic nanoparticles injected into the bloodstream. It produces three-dimensional images in real time at millisecond intervals. MPI is capable of imaging the distribution of nanoparticles with high sensitivity high spatial resolution (~0.4 mm), and high imaging speed (~20 ms). MPI allows cells attached to the nanoparticles to be tracked throughout the body. Imaging does not use ionizing radiation and can produce a signal at any depth within the body. The nanoparticles are stable while attached to a cell, non-toxic, and remain detectable beyond 87 days.

Other types of detectors could be used as well. Nanoparticles have been reported in the literature, that consist of bismuth-iron oxide composite cores. The heavy bismuth metal acts as an x-ray attenuating agent and can be used to image nanoparticles with a CT scanner or a fluoroscope (which detect x-rays). Nanoparticles have also been produced that consist of a radioactive fluorine isotope ($^{18}$F)-iron oxide core, which can be imaged by a PET or a SPECT scanner (as a result of radioactive decay, the fluorine isotope emits positrons which annihilate electrons that they collide with within the body, producing gamma rays that can be detected by PET and SPECT scanners). Other radionuclides (radioactive isotopes) could be used as well. Iron oxide can be detected by itself in an MRI scanner. Consequently, an MRI scanner can be used to detect nanoparticles without the need to add other elements to them (such as bismuth or fluorine). Additionally, all three materials can be combined to form nanoparticles, as well, for use in a scanner which combines some or all imaging methods. MRI and CT have exceptional spatial resolution but lack sensitivity, whereas PET is highly sensitive yet provides no detailed structural information. Thus, combinations of these imaging methods can provide the anatomical resolution and molecular sensitivity needed for accurate diagnoses and treatment and, by using one type of combination nanoparticle, serving as the contrast agent for all imaging methods, the accuracy and consistency of diagnosis and treatment can be significantly improved.

The use of MRI in such a theranostic system is especially valuable because of its ability to image soft tissue with high-resolution and high contrast, without the use of ionizing radiation or potentially harmful radiotracers. Iron oxide nanoparticles have been extensively researched for their use in augmenting contrast for MRI. While increasing contrast, they can help to sharpen images, enhancing their details. The most widely available MRI contrast agents are gadolinium chelates, from which Gd-DTPA is the best well-known and, despite its potential toxicity, has been used with a protective coating in clinical applications for years. Superparamagnetic and paramagnetic iron oxide nanoparticles, on the other hand, are generally non-toxic and are also used as nanosized MRI contrast agents, providing twice the contrast of gadolinium.

Another advantage of using MRI in a theranostic system is its ability to monitor cargo release from cargo-carrying iron oxide nanoparticles. During MR imaging, a static linear magnetic field aligns the axes of precessing atomic nuclei (mainly the protons of hydrogen atoms within water molecules). An RF pulse then causes the nuclei to flip so that their precession axes become perpendicular to their previously aligned orientation, after which the RF pulse ends and the nuclei relax back into their previously aligned orientation, emitting radiofrequency signals of their own in the process, which are detected to form an image. When nanoparticles are "loaded" with drug cargo, water diffusion in the vicinity of the iron oxide cores of the nanoparticles is inhibited, which changes the relaxation time (as compared to what it would be if the nanoparticle was not "loaded") and, consequently, alters the nanoparticle MRI image density, thereby acting as an indication of the degree of drug delivery (unloading) from the nanoparticles. If a therapeutic drug is "radiolabeled" (attached to a radioactive tracer), a "biodistribution" scan can be made to determine the uptake of the drug in tissues, its concentration, and its eventual elimination.

One problem with MRI theranostics is based on the observation that conventional MRI techniques are unable to quantify tissue levels of iron oxide nanoparticles when their concentrations exceed ~1 mg Fe/g tissue, which, studies suggest, have the greatest potential to generate significant heating efficacy (as mentioned herein above). The two primary problems are: 1) with such high concentrations, the image predicts a larger distribution of nanoparticles than actually occurs (i.e., the perimeter of dark hole (or signal void) in the image is larger than the actual perimeter of the area in which nanoparticles exist in high concentrations), and this confuses image detail interpretation, and 2) these signal voids are generally indistinguishable from tissue/air boundaries, further confusing their interpretation. This problem is solved by utilizing one of a number of special MRI scanning sequences in which, instead of iron oxide nanoparticles appearing as over-sized dark holes (called "negative contrast"), the nanoparticles cause bright spots in images (called "positive contrast"), making it easier to accurately distinguish them from other tissues and air/tissue boundaries.

The following explains how this is done. MRI is based on the magnetic properties of atomic nuclei. A powerful, uniform, external magnetic field (along the "z axis") is employed to align the proton spins that are normally randomly oriented within the water nuclei of the tissues being examined. Additional electromagnetic coils produce gradient (varying in strength over a defined space) magnetic fields in all three dimensions (x, y, and z). The alignment of proton spins is then disrupted by the introduction of an external pulse of RF energy which excites (rotates) a component of the proton spins (e.g., by an angle of 1-90°) into the transverse (xy) plane which is perpendicular to the uniform magnetic field. These nuclear spins rotate (or precess) in the xy plane and gradually go out of phase with each other (i.e., transverse relaxation) and return to their resting alignment parallel to the uniform magnetic field in the z axis once again by the process of longitudinal relaxation. As the spins precess in the xy plane, they produce an electromotive force (EMF) which is the source of signal picked up by receiving coils and are measured. The gradient magnetic fields are turned on and off and their strengths are changed over time to produce different precession frequencies from each point within each plane of the body area being scanned. Fourier transformation is used to convert the frequency information contained in the signals from each location in each imaged plane to corresponding intensity levels, which are then displayed as shades of gray in an arrangement of pixels. By varying the sequence of RF pulses applied and collected while applying different magnetic field gradients, different types of images are created from different planes and tissue locations.

Repetition Time (TR) is the amount of time between successive excitation RF pulses in a given MRI sequence. Time to Echo (TE) is the time between the application of a given excitation RF pulse and the time at which the signal (which, in some cases, has the form of a gradient- or spin-echo) is acquired. Tissues can be characterized by two different proton spin relaxation times, characterized by the exponential time constants, T1 and T2. T1 (longitudinal relaxation time) is the time constant for excited spinning protons to realign with the external z axis magnetic field (returning to equilibrium). T2 (transverse relaxation time) is the time constant describing how long it takes for excited spins to go out of phase with each other within the x-y plane. A short T2 means that the signal decays very rapidly, so substances with short T2s have smaller signals and appear darker than substances with longer T2 values. The choice of TR and TE determines the sensitivity of the imaging sequence to different T1 and T2 values. For example, certain choices of pulse sequence and TE and TR settings will highlight fat tissue within the body. The timing of TR and TE in certain sequences can be set to make T2-weighted images which highlight both fat and water within the body. The most common MRI sequences are "T1-weighted" and "T2-weighted" scans. T1-weighted images are generally produced by using short TE and TR times. The contrast and brightness of the image are predominately determined by T1 properties of tissues. Conversely, T2-weighted images are generally produced by using longer TE and TR times. In these images, the contrast and brightness are predominately determined by the T2 (fat and water) properties of tissues. During an actual MRI scan, however, the transverse magnetization (in the x-y plane) decays faster than would be predicted by intrinsic atomic and molecular mechanisms; this rate is denoted T2*. T2* can be considered an "observed" or "effective" T2, whereas T2 can be considered the "natural" or "true" T2 of the tissue being imaged. T2* is always less than or equal to T2. T2* results principally from inhomogeneities in the main magnetic field. These inhomogeneities may be the result of intrinsic defects in the magnet itself or from susceptibility-induced field distortions produced by the tissues or other materials placed within the field. Certain MR sequences using gradient echoes and relatively long TE values are called T2*-weighted. They are used to accentuate local magnetic homogeneity effects to aid in the detection of hemorrhage or calcifications. T2*-sensitive sequences also form the basis for functional MRI (fMRI) using the "BOLD (Blood Oxygen Level Dependent)" technique.

MRI was developed based on nuclear magnetic resonance (NMR) chemical spectroscopic analysis techniques. Three different types of NMR techniques were developed: continuous wave (CW), pulsed, and stochastic. After realizing the efficiency of pulsed Fourier transform (FT) spectroscopy, pulsed FT supplanted CW as the main spectroscopic technique, and eventually became the method of choice when MRI was developed. Dr. Michael Garwood et al., at the University of Minnesota, developed a new MRI method that can be considered as a combination of all three basic NMR techniques. As in CW NMR, this method uses swept RF excitation (sequentially stepping frequencies over a range), but the sweep rate far exceeds the CW sweep rate, even during a rapid scan. Unlike the CW method, in which the signal is acquired in the frequency domain, the signal is treated as a function of time, as in the pulsed FT method. In addition, the method uses correlation, identical to that used in stochastic NMR, to extract the signal arising from the proton spin system. This method is called "SWIFT", for Sweep Imaging with Fourier Transformation. The concept of using swept RF excitation instead of a monochromatic (single frequency) RF pulse, or stochastic excitation, and then reconstructing the NMR spectrum using the correlation method, was mentioned more than three decades ago, but was never put into practice. The main advantage of the CW method over the pulsed MRI technique is its low RF power requirement. However, due to the slow rate of acquisition, CW MRI is time consuming and thus impractical for in vivo applications. The main limitation in stochastic NMR is the need to create truly random excitation in order to avoid systematic noise artifacts. In principle, the SWIFT technique, using the same "time shared" acquisition, can be considered to be a branch of stochastic NMR. The main advantage of SWIFT originates in its nearly simultaneous excitation and acquisition technique. In addition, it requires much less peak RF power than conventional MRI to produce comparable high-bandwidth imaging. In conventional MRI, excitation and acquisition events are separated by the length of time known as the echo time (TE), which is typically >1 ms. This length of time is too long to allow detection of slowly tumbling nuclei with short T2 relaxation times. By comparison, SWIFT allows a TE that is near zero, because signal acquisition can begin within a few microseconds after excitation. Several methods can be used to prevent excitation pulses from being directly received and confused with the proton signal (or EMF) that are needed for analysis and image production, such as careful orientation of the receiving coils (putting them 90° out of phase with the transmitting coils), using circulators or quad hybrid passive electronic components, and using active cancellation of the excitation pulses. Since each frequency in a sweep of many frequencies is used sequentially, only a small peak power is needed, and in this way, frequency-swept excitation, as done in SWIFT, reduces the required level of RF isolation needed to separate the MRI signal from leakage RF transmitted signal at each frequency. SWIFT is a powerful tool for imaging objects having a broad distribution of relaxation times, including very short T2 values. The method employs a sequence of RF pulses of different (swept) frequencies, each having a duration that is typically in the millisecond range. The frequency-swept excitation distributes the signal energy in time and, thus, dynamic range requirements for proper signal digitization are reduced, as compared with conventional MRI. In one version of SWIFT, known as gapped-SWIFT, the pulse is divided into segments, each having RF power turned on for a short duration, following a delay with the RF power turned off. Data sampling is performed after the pulse segment. This type of time-shared excitation and signal acquisition is carried out in the presence of an applied magnetic field gradient used to impart a spatially dependent precession frequency on the spins. The minimum temporal spacing of pulses (repetition time) (TR), is simply the pulse duration plus the amount of time needed to make an incremental change in the orientation of a magnetic field gradient. The field gradient used for spatial-encoding is not pulsed on and off, as in conventional MRI, but rather is stepped in orientation in an incremental manner, which results in very low acoustic noise. This unique short acquisition method is relatively insensitive to sample motion, which is important for imaging live subjects. After acquiring a full set of frequency-encoded projections, 3D images can be reconstructed using a 3D back-projection algorithm. For example, with acquisition parameters that standard MRI scanners can readily achieve, a 3D image with a matrix size=128×128× 128 can be acquired in less than 30 s. A further approximately 30% time reduction is possible without affecting image quality using an equidistant projection sampling method. SWIFT provides high S/N (signal-to-noise ratio) without observable image artifacts. The SWIFT technique has many novel and beneficial properties for MRI: (a) Fast—The method avoids not only delays associated with refocusing pulses or gradient inversion, but also time for an excitation pulse, which is combined with the acquisition period. (b) Sensitive to short T2. (c) Reduced motion artifacts—Because the SWIFT method has no "echo time," it is less sensitive to motion and flow artifacts than conventional MRI methods. As compared with other fast sequences, SWIFT loses much less signal due to either diffusion in the presence of a gradient or uncompensated motion. (d) Reduced signal dynamic range—Because different frequencies are excited sequentially, the resulting signal is distributed in time, leading to a decreased amplitude of the acquired signal. This allows more effective utilization of the dynamic range of the digitizer. (e) Quiet—Last, but not least, the SWIFT method uses a small step when changing gradients between projections, and thus the fast, large angle gradient switching that creates loud noise with conventional MRI is avoided.

In addition to producing images of tissues within the body, MRI can produce images of metallic nanoparticles within the body, which is very important during hyperthermia treatment to determine tissue temperatures, the location of nanoparticles and tumors, progression of treatment, and other factors. Accurate knowledge of the distribution of iron oxide nanoparticles (IONPs) within the patient is crucial for effective and safe treatment. Traditional MR imaging sequences are unable to quantify IONP concentrations in the therapeutic concentration range because, above a certain value of iron, the MRI signal is dominated by noise, even at the shortest possible echo times, due to ultrashort T2* values. FDA-approved nanoparticle formulations called Resovist and Feridex, for example, typically produce hypointensive signals (with negative contrast) when imaged with conventional MRI gradient-echo (GRE) and spin-echo (SE) pulse sequences, Although low concentrations of IONPs can often be quantified with such GRE and SE sequences, quantification of high IONP concentrations (in the therapeutic range) is not possible with these methods because of the strong negative contrast produced. GRE and SE sequences are sensitive to IONPs at low concentrations because of their relatively long echo time (TE) (typically >1 ms) and their shorter T2 and T2* time of spins in the presence of IONPs. However, when using such traditional (echo-based) pulse sequences, high concentrations of IONPs can be quantified only when the T2 or T2* time is long enough to be imaged. At high IONP concentrations, however, T2 and T2* values decay more rapidly and become too short to enable accurate IONP quantification. X-ray computed tomography (CT), on the other hand, which is used clinically for IONP quantification during magnetic nanoparticle hyperthermia in Europe, relies on small changes in bulk density and is only practical at even higher nanoparticle concentrations (>5 mg Fe/mL). This leaves a gap in the detectable IONP concentration range (1 to 5 mg Fe/mL) where neither CT nor conventional MRI has a sufficient sensitivity for accurate quantification. To solve this problem, SWIFT would be combined with the "Look-Locker" method to map T1 times of IONPs in these high concentrations. In addition to SWIFT, other MRI pulse sequences capable of preserving signal from spins with ultrashort T2* times have also been developed in recent years, like UTE, ZTE, and PETRA. These sequences have negligible T2 or T2*-weighting because signals are acquired immediately after or during the excitation pulse. With these sequences, IONPs can be detected and quantified based on the shortening of the longitudinal relaxation time (T1) of water. The most common T1 mapping methods are based on inversion recovery (IR) or saturation recovery (SR). The Look-Locker method is a way to accelerate T1 mapping for both SR and IR methods. Ferrotec EMG-308 iron-oxide nanoparticles (Ferrotec USA Corp., Bedford, NH) with 3.0 mg Fe/mL, for instance, has been used with the SWIFT method to create images with positive IONP contrast, and the SWIFT Look-Locker technique was able to quantify the high local concentrations of IONPs. As an example, imaging and mapping of the longitudinal (T1) relaxation rate have been performed by others with SWIFT, and signal enhancement from positive T1 contrast caused by IONPs was observed and quantified in vivo in liver, spleen, and kidney at concentrations up to 3.2 mg Fe/(g tissue wt.). Traditional echo-based pulse sequences show only noise at these high IONP concentrations. By having no "echo" and being able to capture signal from spins with very short T2* values, SWIFT can probe the effect on T1 as the concentration of iron changes.

When heating nanoparticles and their surrounding tissues, inhomogeneities within tissues and the existence of boundaries and different tissue types create local differences in heat absorption and heat conductivity. This makes 3-D real-time temperature mapping necessary to prevent hot spots and uneven heating. Temperature mapping is also important to be sure that healthy cells don't receive too much heat, while tumor cells receive sufficient heat to create the desired damage. Based on the temperature dependence of several proton relaxation parameters, "proton spectroscopic" MR imaging (referred to as MR Thermometry or MRTh) allows both continuous thermometry and the 3-D mapping of temperature changes, indicating absolute temperature values. This technique utilizes the temperature dependence of the "proton resonant frequency shift" (PRFS) of the hydrogen protons in water (which is in most body tissues). The use of temperature sensitive contrast agents can further increase the sensitivity and accuracy of the technique. Examples include paramagnetic thermosensitive liposomes, lanthanide complexes, multi-functional nanoparticles, and spin-transition molecular materials. MR imaging relies on the flipping of precession axes of protons in water's hydrogen atoms within the body. The atoms (and, thus, their protons) are placed within a static magnetic field, whose strength (for the most part) dictates their resonant frequency. However, their resonant frequency also depends on temperature and, so, will shift when their temperature changes. Normally, at ambient temperatures, water molecules are bonded to each other and, as a result, electrons are somewhat pulled away from their protons by the distortion of the hydrogen bond connecting each water molecule to other water molecules. Consequently, any single water molecule's electrons provide less diamagnetic "shielding" of the proton in its nucleus. This reduction in shielding increases the magnetic field detected by the proton, and, thereby increases its resonant frequency. When the temperature rises, however, the length of the hydrogen bonds between water molecules increases, until they break. Once the bond is broken, the isolated, free, single water molecule's electrons get closer to the hydrogen proton and increase their diamagnetic shielding of the proton from the magnetic field applied by the MRI. This reduces the field strength detected by the proton, thereby reducing its resonant frequency. For a 1.5 T imaging system, which uses an RF excitation field at 63.85 MHz, the proton's resonant frequency will change by 0.6385 Hz/° C. of change. This small change in resonant frequency can be detected to produce a very sensitive map of temperatures within the area being imaged by the MRI. Such a temperature map will allow for the real-time monitoring of heated nanoparticles and their surrounding tissues, so that the temperature can be controlled in different areas as necessary. A very valuable advantage of such spatially accurate temperature monitoring and control is the ability to reduce or eliminate heating in areas where patients have conductive implants (which normally prevents them from being able to have an MRI). Initially, a low power signal can be used to detect the location of such conductive implants, providing the coordinates of spots within a patient that shouldn't receive EM radiation. The shape of the heating EM radiation field can then be altered to avoid such areas. Consequently, patients with such implants will be able to have MRIs as well as hyperthermia or Holothermia™ treatments. MR temperature monitoring has been successfully demonstrated in vivo and is regularly used in a number of clinical applications, mainly in combination with focused ultrasound (FUS) and laser heating. The method is widely used in thermal ablation procedures with magnetic fields at or below 3T. PRFS mapping previously had two limitations. Firstly, although it has excellent linearity and temperature dependence, regardless of the tissue type being imaged, except for fat. Fat has no water hydrogen atoms, and, thus, shows no temperature dependence effect. As a result, although temperature mapping of tissues with little or no fat are very accurate, mapping of tissues that have significant fat content is inaccurate. Secondly, motion, such as from respiration, changes in muscle tension, heartbeat, peristalsis, organ motion and deformation, and the expansion, swelling, structural changes, and deformation of heat-treated tissues, causes artifacts, such as ghosts and blurring of mapping details, making motion the most prevalent problem for many areas of PRFS temperature monitoring, impeding its widespread acceptance for clinical applications.

Some of the unwanted motion can be monitored with external methods and synchronized with MR imaging such that image acquisition occurs during a stable period of the motion source (called "gating"), such as the breathing cycle or heartbeat, for instance. Conventional respiratory gating in animals under general anesthesia and mechanical respiration has been successfully used by others.

PRFS-based temperature imaging generally can be divided into two techniques, "spectroscopic imaging" and "phase imaging." Spectroscopic imaging usually suffers from low spatial and temporal resolution. It involves measuring signals at many different points in time so that frequency information can be extracted. In contrast, phase imaging typically samples the signal at one time and allows temperature measurements at sub-second times with high spatial resolution. Clearly, sampling a single value instead of many different ones can allow faster imaging with better spatial resolution, which can be especially useful for the real-time monitoring of thermal therapies in moving organs. Such a reduction in the amount of sampled data does, however, make phase imaging more vulnerable to corruption by fat signals and/or by field variations unrelated to temperature. A "baseline" (or reference) image is required with phase imaging before heating so it can be subtracted from the image acquired after heating. The subtraction increases the temperature error by a factor of 2 and makes the phase-mapping method vulnerable to motion and field drifts. Despite these shortcomings, phase imaging is by far the most commonly used PRFS thermometry approach, Alternately, so-called "referenceless" methods have been proposed to estimate the baseline (reference) phase image from each later acquired phase image itself, obviating the need for a baseline reference to be acquired at a previous time, By removing the need for baseline image subtraction, this method is insensitive to "inter-scan" motions (motion between successive scans). Such a referenceless method requires a heating spot that is at least partially surrounded by a non-heated area. An alternate adaptive method of phase imaging was developed by De Senneville et al. which can be used in real-time. In their approach, an atlas of motion is constructed with 50 MR images acquired during a pretreatment period without heating. During the thermal therapy, every dynamic image acquired is then compared to the atlas images. The corresponding phase image in the atlas that has the maximum similarity to the dynamic image is used as the reference for temperature mapping.

Since fat cells lack the hydrogen protons of water, their presence would corrupt the temperature data acquired from water molecules in the areas of the body where too much fat is present. Consequently, techniques need to be employed to suppress fat-related data in order to produce accurate temperature maps with these techniques. Various fat-suppression methods have been utilized for temperature mapping, such as the use of spectrally selective RF pulses, short "tau inversion recovery" (STIR), and so-called "Dixon" methods.

A hybrid technique was developed by Chang-Sheng Mei at Boston College, which combined three additional procedures to compensate for motion and the presence of fat cells. First, he reduced the amount of time spent on acquiring each image, which limits artifacts due to intra-scan motion (motion within a single scan), by reducing the area being excited with the RF excitation pulse as well as also constraining signal monitoring to the same reduced area. Second, he further reduced image acquisition time by using "Parallel Imaging," which relies on the fact that the imaged object is "seen" simultaneously by a number of different coils placed at different locations around the imaged anatomy. Thirdly, he used Fourier encoding (an advanced mathematical method of selective signal processing) of the overlapped signals to eliminate aliasing artifacts resulting from the superposition of the separately acquired images from the different coils. This combined approach greatly reduced motion artifacts by significantly reducing image acquisition time and virtually eliminated temperature mapping errors that would otherwise be generated by the presence of fat tissue by excluding data from fat containing areas ("fat suppression").

An entirely different approach to solving the problems of accurate MR temperature mapping was recently proposed by J. H. Hankiewicz et al. at Colorado University. Their method of forming an MRI temperature map is based on the use of nanoparticles with a Curie temperature at the top of the range of interest (such as 43° C. or higher for hyperthermia or Holothermia™ treatment). The Curie temperature is the temperature at which a material's thermal motion becomes stronger than its inter-particle magnetic attraction. Beyond that temperature, electromagnetic heating essentially stops. Using nanoparticles with a magnetization that is strongly temperature dependent (which happens near a nanoparticle's Curie temperature), one can obtain a temperature-dependent linewidth in NMR, and consequent changes in MRI intensities, with an accuracy of about 1° C. This is obtained from the induced brightness changes in the T2* weighted MRI images. The nanoparticles embedded in the tissue will create a local dipole magnetic field that makes the static magnetic field of the MRI scanner inhomogeneous and, as a result, broadens the NMR line. This line broadening will be temperature-dependent since the magnetic particles exhibit a rapid change of magnetization as a function of temperature near the nanoparticle's Curie temperature. As the nanoparticle heats up, the MR linewidth can show a greater than 250% decrease as the temperature is increased over a 30° C. range, for instance, depending on the nanoparticle composition. Different compositions (alloys and heterogeneous structures) and sizes of magnetic particles will change the temperature-dependent MR image contrast. By doping (mixing) elements together, the Curie temperature of the nanoparticle can be set as desired. For instance, Permalloy ($Fe_{0.2}Ni_{0.8}$) normally has a Curie temperature of 576° C. When it is 50% doped with Cu, however, the Curie temperature is shifted down to 55° C., which is perfect for hyperthermia or Holothermia™ cellular heating. To know the absolute temperature, one also needs to know the concentration of the magnetic particles. However, with an unknown concentration, it is possible to measure temperature differences, such as the differences introduced by local heating during hyperthermia or Holothermia™ procedures. Different shades of grey (or even various pseudo-colors) displayed in the MRI images can be calibrated to present a map of temperature changes, starting from the nanoparticles' pre-treatment temperatures as an initial baseline. Another advantage of using this technique is based on the fact that magnetic heating stops when a material reaches its Curie temperature. This can prevent damaging runaway-heating during hyperthermia or Holothermia™ treatment.

As explained herein above, a theranostic approach is preferred for optimal hyperthermia or Holothermia™ treatment, simultaneous with monitoring of tissue and nanoparticle locations, release of cargo, and temperatures. While conventional MRI is one of the preferred methods for accomplishing such monitoring, it still has the drawbacks of non-real-time display as well as significant electrical and acoustical noise. These problems can be eliminated with the use of a new MRI system currently under development (US patent application publication 2016/0282429), called ULTRA (for Unlimited Trains of Radio Acquisitions), proposed by Dr. Michael Hutchinson in New York. Conventional MRI systems utilize three gradient-producing coils (one for each dimension) to produce gradient magnetic fields that are turned on and off in reversing directions extremely rapidly within a single scan (which can take several minutes). In addition, they also use repeating proton-excitation RF pulses during the same time period (all of which contributes to the electrical and acoustical noise generated by conventional MRI imaging). Data is gathered individually and sequentially from each voxel in the three-dimensional patient space, resulting in relatively long imaging times of the entire volume. The ULTRA MRI system, on the other hand, uses only one gradient coil which is on (without change) all of the time, and only one RF pulse to flip all precessing protons, causing them to repeatedly radiate their RF signals, which are captured and displayed as a full 3-D volumetric image. The superposition of the constant single gradient magnetic field onto the fixed static magnetic field of the MRI magnet results in the formation of a series of "slices" in space within the 3-D patient volume, each with its own unique magnetic field strength, that are perpendicular to the gradient field. The patient's water protons within each such slice in space, therefore, seeing a different magnetic field strength from that of any other slice, precess at a different resonant frequency than the protons within any other slice in space, making the emitted proton RF signal strength values differentiable between slices. Since the magnetic field is consequently different from one slice location to the next, but constant within each slice, data can be gathered from all slices simultaneously and separated within a computer by Fourier analysis, delineating the data that comes from each slice separately. Instead of the relatively simple receiving coil arrangement found in a conventional MRI system, the ULTRA system uses a series of side-by-side rings, forming a cylinder placed around the patient. Each ring consists of an array of tiny coils, altogether constituting a cylindrical coil array. The data value from any given voxel within any given slice is detected from all coils simultaneously, creating a pixel intensity map within each slice, since each voxel within each slice is at a different distance from each of the surrounding coil locations, and can therefore be calculated. As a result of this arrangement, all voxel's from the entire 3-D patient space are captured and displayed simultaneously. An entire 3-D volume can, thus, be imaged in as little as 1 ms, which is between 250 and 2500 times faster than comparable conventional MRI imaging, allowing for "real-time" scanning and display. Signal-to-noise ratio (SNR) is excellent due to the elimination of RF noise from gradient switching, which is used in conventional MRI. This also makes ULTRA MRI ideal for measuring temperature in 3-D in real time during treatment.

Consequently, in summary, nanoparticles, and thus, tumor cells (or other cells of interest) that they are connected to, should be detected to diagnose disease and its location within the body. Their detection and monitoring will also allow for the determination of cargo release, the progression of treatment, and the tissue response to treatment, providing feedback for real-time treatment modifications to maximize treatment efficacy, while minimizing collateral damage or side effects. This can be accomplished with a theranostic system that combines hyperthermia or Holothermia™ treatment equipment with diagnostic imaging equipment such as an ESR scanner, MPI scanner, PET scanner, CT scanner, fluoroscope, MRI scanner with Swift imaging, and/or ULTRA MRI scanner to produce imaging of the patient volume of interest with a superimposed temperature map, and the elimination of confusing negative contrast holes in the image and artifacts from motion and intervening fat, all operating as close to real time as possible.

In summary, once nanoparticles are injected systemically and have reached their targets, activation energy can be sent to them, preferably at the nanoparticles' or cell's resonance frequency, to produce the maximum effect with the least amount of applied energy. This is best achieved by using FerroMagnetic Resonance Heating (FMRH) or cell-resonant frequency heating, wherein RF energy is sent to cells or nanoparticles, at their resonant frequency, whose electron spins are initially aligned by an external magnetic field, which then flip to a new orientation as a result of the application of the RF energy, allowing the RF energy to be absorbed very efficiently and converted to heat efficiently by the nanoparticles. HET can be used alone or with nanoparticles for precise treatment without harming healthy cells. The hyperthermia or Holothermia™ treatment-system equipment is preferably combined with a scanning system, such as an MRI or other scanner, to diagnose disease by detecting the presence of concentrated nanoparticles, to direct and monitor treatment progress, and to measure and manage temperature changes in 3-D during treatment.

Holographic Energy Teleportation (HET) Imaging and Other Applications

The present invention also makes possible a new form of imaging, which is referred to herein as "HET scanning" or "HET Imaging." Even though it is described herein with regard to medical imaging, this form of imaging has many other applications as well, such as nondestructive testing of materials, structures, and components. HET provides a way to create a point of high energy at any designated location in space, even inside of an object, while providing a large surrounding region of no energy. Consequently, energy can be teleported into any voxel(s) within a patient's body, for instance, from which it will then radiate outward, and will make changes, such as elevating the temperature of the voxel(s) teleported to. Changes that consequently take place in the irradiated voxel(s) can be detected to convey information about how that energy interacted with the contents of the selected voxel(s), and if desired, with the voxels it encountered upon radiation outward from the irradiated voxel(s) on the way out of the body. Such energy can create measurable effects that can provide information about chemical bonds, tissue density, the presence of vascularization, bone density, etc., and can be used as a diagnostic imaging tool. In materials and structures, uneven expansion resulting from minimal heating can indicate hidden internal flaws. This information can be used to prevent premature part failure, even if the "part" is a patient's blood vessel. Using HET as a diagnostic imaging technique along with HET for tissue treatment, can also provide data about the effectiveness of the treatment, such as by showing the temperature gain, expansion, disruption, structural changes, etc. of treated tissues. This can be done on a voxel by voxel basis, scanning out a planar or volumetric region of interest (ROI).

Any method of energy detection (selected for the type of energy used) such as MRI or IR imaging can be used outside of the patient's body (or object) to gather the data. Use of channel state estimation, as described herein above, can be used to cancel reflection and scattering of the energy as it travels outward from its point of origin to the detector or detector array. This will allow accurate measurement of the changes made to the energy pulse detected in a straight line, or selected multiple straight lines, from the emitting voxel. This channel state correction method can be used if the energy source is teleported to any location within the body, or even if the energy source is located outside of the body and not teleported into it, allowing the energy to travel through the body and out the other side, as is done with a CT scan, for instance. However, unlike a CT scan, no ionizing radiation is required to get the energy to pass straight through the body for tomographic analysis and image reconstruction. Normally, scattering would prevent such a scan (with non-ionizing or high frequency energy) from providing useful information, but with cancellation of scattering noise, accurate data can be collected. Energy teleported into a voxel in the body can cause a slight amount of heating to occur within the voxel, which can be measured from outside the body by a sensitive infrared camera system, or by an MRTh scan.

If HET is carried out with two points of constructive interference, one within the body, and the other outside of the body, the two areas of constructive interference will be entangled. Consequently, if the conditions within the body at the point of constructive interference are altered (such as by absorption), the change will be detectable at the second point of constructive interference outside of the body. Thus external monitoring of an external constructive interference point (DEP) can provide data about a specific voxel within the body without the need for channel state correction to cancel the effects of absorption and scattering. Essentially, the energy is teleported to a spot within the body where it is altered by the condition it finds there, and then it is teleported outside of the body to a detector which only measures the effect on the energy at the DEP point within the body. This method can be used to generate DEP's at various locations within the body, creating a scan of an entire region of interest (ROI). Even though one point (DEP) of constructive interference can be sequentially created at many different points within the body (preferably sequentially), the DEP generated outside of the body can always be located at the same single location, where a detector can be placed. This information can be used to generate a three-dimensional map-type image of densities, for instance, such as seen in an MRI or CT scan image. However, no ionizing x-rays, such as are used in a CT scan, are needed, and no magnet, with all of its complexities, such as is used in an MRI scanner, is needed either. This technique is referred to as "HET entangled scanning."

HET MRI Scanning

MRI scanners are unique in their ability to non-invasively determine the difference between healthy and diseased cells, without the use of any ionizing radiation. This includes detecting cancerous malignancies as well as other disease conditions. MRI scanning allows for the detection of T1 and T2 data, which uniquely classifies healthy and diseased cells, and gives detailed data about soft tissues at a level that CT scanning can't match. MRI accomplishes this with the use of a strong magnetic field and three magnetic gradient-field-producing coils which must be switched on and off rapidly with many different power and timing configurations. Unfortunately, this slows down the scanning process, resulting in the patient's need to lie uncomfortably still for 30 minutes or more to allow a scan to be completed. The required long scan times make it impossible to scan children or pets unless they are anesthetized, which carries increased risk. This time delay also limits the number of scans that can be accomplished per day, limiting profitability. Both CT and MRI scanning are limited in their ability to provide high tissue resolution since tissues smaller than about 1 mm can't be discerned. This can be very critical because early cancers start out much smaller than 1 mm and, therefore, can't be diagnosed in their early stages with these systems. This is especially unfortunate because, when cancers are caught in their early stages, their chances of a complete cure are very high. Furthermore, when cancers metastasize, tiny cancer cells and cancer stem cells travel to other parts of the body to grow bigger cancers in other locations, which is usually fatal. If the tiny cancer cells and cancer stem cells could be detected and imaged before they grow large tumors, they could be destroyed, preventing widespread metastasis of cancer throughout the body. Nearly 95% of all deaths from cancer results from metastasis.

HET can be used with MRI technology to produce a superior type of MRI scanner, solving all of these problems. Such a system is referred to herein as an HET MRI scanner.

Normally, an MRI scanner requires gradient coils that are addressed in a complex pattern of activation and deactivation (causing expansion and contraction) of gradient fields. The many different gradient fields that are produced over time add together to produce many different planes in space at many different orientations which are planes of constant magnetic field strength. Pulsed RF signals of different frequencies are able to excite precessing protons within the hydrogen atoms of water molecules located within a given plane of constant magnetic field strength. By altering the gradients in various specific complex ways and, thus, the orientation of planes of constant magnetic field strength, as well as the phases of precessing protons, data can be collected, one plane at a time, one line at a time, and one point at a time to generate three-dimensional MRI image data. Changing the gradients requires de-energizing the gradient coils and collapsing the magnetic fields, and then re-energizing the gradient coils and their generated magnetic fields in a new configuration. This process takes time. In addition, the growing and collapsing magnetic fields attract, stress, and move the metallic conductors and structures within the scanner, creating extremely loud noises during the entire scanning time. Furthermore, the ability to differentiate between different planes within the body is limited by the difficulty of detecting subtle differences in magnetic field strengths in adjacent areas of space. Consequently, conventional full-body MRI scanners are generally limited to displaying features (voxels) that are 1 mm in size or larger.

Using HET with a modified MRI scanner can eliminate these drawbacks. In one embodiment, an MRI scanner with a conventional magnet (such as one with a field strength between 0.6 and 3 Tesla) can be used without any gradient coils. The elimination of gradient switching will eliminate the usual noise of an MRI scanner and will eliminate the long required scan times. Instead of gradient coils, HET can be used to send an RF pulse to any specific point (creating an RF DEP) within a patient, located in a fixed magnetic field. This will cause the energizing and flipping of water-hydrogen-proton precession to occur only at that point of constructive interference, at the proper resonant frequency, and at the existing magnetic field strength at that point. Detection coils everywhere within the scanner will pick up the echo signal produced when the RF pulse stops and the protons decay back to precessing around the fixed magnetic field axis. T1 and T2 data will be detectable as in a conventional MRI scan.

A new method of optical resonance excitation is disclosed here to allow the size of the RF DEP produced to reach sub-millimeter dimensions, while still being able to produce resonance at conventional low RF frequencies. In order to produce a DEP at a size of 1 mm or less, the teleported energy must be at a frequency of 300 GHz or more, since the size of the DEP is on the order of the size of the wavelength of the energy used. However, using conventional MRI field strengths, the resonance frequency required for water-hydrogen protons is less than 130 MHz, which has a wavelength of 2.3 meters. Consequently, the energy frequency needed (300 GHz or more) to produce the required microscopic DEP's will not produce resonance in a conventional MRI system. To eliminate this problem, an IR or NIR beam produced by a laser can be modulated with the required resonance frequency (for instance, 63 MHz for use with a 1.5 Tesla magnet or 126 MHz for use with a 3 Tesla magnet). This can be done with conventional methods, such as AM modulation. Another method of producing the required beam is to start with an IR or NIR beam and a second IR or NIR beam that is slightly down-converted or up-converted from the first beam to produce sum and difference frequency side bands, with one of the side bands being at the required resonance frequency. One method for doing this is explained in detail herein with regard to FIGS. 13 C and 13 D. The carrier wave, at an IR or NIR frequency (such as between 300 GHz and 430 THz) can produce a DEP spot as small as 700 nm (0.7 microns). By comparison a red blood cell is about 7 microns in diameter. Although this high frequency carrier will allow the production of a submillimeter DEP, only the modulated sideband at the resonance frequency of the hydrogen proton will excite the water's protons to generate the MRI echo signal.

As the size of the voxel selected decreases for higher resolution, the echo's signal strength will decrease, making it harder to detect. To compensate for this reduction in echo strength, a higher powered repeating RF pulse can be used to energize more of the protons within the voxel, up to the point of full saturation. In addition, the RF pulse can be repeated as many times as needed to produce a stronger echo, as a result of time averaging. This increases the signal-to-noise ratio, allowing a useful signal to be detected. Once a signal of sufficient strength is detected from the voxel being addressed, the scanner can then send the RF pulse (as another DEP) to an adjacent point within the patient, repeating the process until all voxel's within the region of interest (ROI) have been interrogated to allow the production of an image. A Fourier transform of detected data, used in a conventional MRI scan to determine the precise location of origin of echo emissions coming from an unknown voxel location within a patient, is also not needed.

This is because all data received at any one time is understood to be coming from a known voxel location where the RF DEP was generated by HET.

Without the use of any gradients, the patient's body is located within a uniform magnetic field. Consequently, a specific fixed RF frequency band can be used to elicit an echo from every point in the body sequentially, without the need to change the frequency generated. Moving the location of the DEP to all the different locations within the patient's body can be done rapidly in a three-dimensional scanning pattern similar to raster scanning, which is done to produce as many as 600 fields per second on a computer or TV monitor, regardless of its size. To speed up data acquisition time, multiple separate receiver coils can be placed throughout the tunnel, or scanning area, that a patient is in. Detection of the phase, and thus the time of reception of a signal from the various receiving coils can localize the source of echoes received, allowing for the placement of RF DEP's at multiple locations within the body simultaneously.

To further speed up scanning of the patient's entire body, in a second embodiment, a single gradient coil can be used, which is on all of the time. This divides the body into individual thin planes of different magnetic field strengths. For the cells in each plane to produce a resonance signal, each plane must be stimulated by a different RF frequency band. Consequently, all required different RF frequency bands can be sent to the entire body simultaneously. Each RF frequency band, however, will only stimulate resonance in only one plane which has the proper corresponding magnetic field strength. This results in all data coming from each different plane of tissues being easily discernible from all data coming from every other plane. Therefore, each separate plane can be scanned (by generating DEPs at different points) simultaneously with every other plane, dramatically cutting down the scan time for the entire patient's body.

HET can be used in many non-medical applications as well. It offers a unique ability to teleport energy with or without information to a desired location, while the energy or information is not detectable over a relatively large intervening area.

It is to be understood that the present inventions may have various other embodiments. Furthermore, while the form of the inventions herein shown and described constitute various preferred embodiments of the invention, this is not intended to illustrate all possible forms thereof. It will also be understood that the words used are words of description rather than limitation, and that various changes may be made without departing from the spirit and scope of the invention disclosed. The scope of the invention should not be limited solely to the examples given.

ABBREVIATIONS USED HEREIN

CIA—Coherent Intensity Amplification
DCG—Dichromated Gelatin
DEC—Desired Energy Cancellation
DEP—Desired Energy Peak
HET—Holographic Energy Teleportation
HOE—Holographic Optical Element
TiCSI—Time-Correlated Standing-wave Interference

The invention claimed is:

1. A method for using nanoparticles to produce desired results in a body of a human or non-human patient upon being illuminated with precisely targeted coherent energy, by:

a) providing a system comprising:
  i. means for illuminating a first region and a second region with at least two pairs of overlapping mutually coherent beams of energy, each said pair of coherent beams overlapping each other so as to produce a resulting standing wave pattern, thereby producing at least two resulting standing wave patterns, with said at least two resulting standing wave patterns overlapping each other and every other resulting standing wave pattern such that each said resulting standing wave pattern intersects said first region and said second region;
  ii. means for adjusting at least one of the amplitude, phase, and frequency of each of said produced resulting standing wave patterns relative to every other said produced resulting standing wave pattern at a selected instant of time, so that each of said produced resulting standing wave patterns has amplitude, phase, and frequency, such that a superimposed produced resulting standing wave pattern undergoes Fourier synthesis to form an energy pattern having constructive interference in said first region and destructive interference in said second region wherein at least one of the amplitude, frequency, and phase of each said resulting standing wave pattern relative to every other said resulting standing wave pattern at a selected instant of time are related to each other such that an antinode of each said resulting standing wave pattern is in phase with and overlapping an antinode of every other resulting standing wave pattern throughout said first region at said selected instant of time during said illumination, so that the said patterns together overlap to produce destructive interference in said second region, and said method further comprising the steps of:
b) illuminating said first region with said at least two pairs of overlapping mutually coherent beams of said energy, each said pair of coherent beams overlapping each other so as to produce a resulting standing wave pattern, thereby producing at least two resulting standing wave patterns, with said at least two resulting standing wave patterns overlapping each and every other resulting standing wave pattern, such that each said resulting standing wave pattern intersects said first region and said second region;
c) adjusting said at least one of the amplitude, phase, and frequency of said produced resulting standing wave patterns relative to every other said produced resulting standing wave pattern at a selected instant of time, so that each of said produced resulting standing wave patterns has said amplitude, phase, and frequency, such that the superimposed produced resulting standing wave patterns undergo Fourier synthesis to form an energy pattern having constructive interference in said first region and destructive interference in said second region,
d) wherein said at least one of the amplitude, frequency, and phase of each said resulting standing wave pattern relative to every other said resulting standing wave pattern at a selected instant of time are related to each other such that an antinode of each said resulting standing wave pattern is in phase with and overlapping an antinode of every other resulting standing wave pattern in said first region at said selected instant of time during said illumination, so that said patterns together overlap to produce destructive interference in said second region; and
e) introducing nanoparticles into the object to be illuminated with said coherent energy by said system targeted at a first region within the object, and f) illuminating the object with said coherent energy targeted at a first region in or on the object, such that a second region in or on the object is in the area of destructive interference.

2. The method of claim 1, wherein the body is of a human patient.

3. The method of claim 1, wherein the desired results include delivering hyperthermia treatment within the body by externally applying coherent energy to nanoparticles, wherein the coherent energy generates heat and dissolves a protective coating of the nanoparticles.

4. The method of claim 1, wherein the nanoparticles are adapted to release chemical agents within the first region, to localize and affect diseased areas with precision.

5. The method of claim 4, wherein the chemical agents are delivered to target cells in a diseased area, thereby damaging cancer or other diseased cells by apoptosis or by damaging proteins and cell structures.

6. The method of claim 1, wherein the nanoparticles release cargo that contains one or more chemical agents that further trigger specific reactions within the body to accomplish desired microscopic and sub-microscopic tasks, or to inhibit or fire neurons, or to release enzymes or hormones, while minimizing the interaction of the chemical agents with healthy cells.

7. The method of claim 6, wherein the chemical agents comprise at least one of chemotherapy drugs or genetic therapy drugs.

8. The method of claim 1, wherein the nanoparticles are constructed to heat up upon the illumination by coherent energy and thereby raise a temperature of cells in said first region beyond their recoverable threshold.

9. The method of claim 1, wherein the nanoparticles include specific vectors for seeking out and attaching to the target cells.

10. The method of claim 1, wherein the nanoparticles are heat-labile coated nanoparticles.

11. The method of claim 10, wherein the target cells comprise at least one of tumor cells or diseased cells.

12. The method of claim 10, wherein the system externally applies the coherent energy to the nanoparticles to generate sufficient heat to release the chemical agents once the nanoparticles are attached to target cells in the first region without generating significant heat in healthy cells in the second region.

13. The method of claim 12, wherein the heated nanoparticles stimulate an immune response in the body.

14. The method of claim 1, wherein the nanoparticles concentrate a detection ability and treatment effects to a nano-sized area even If the first region is larger than the nano-sized area.

15. The method of claim 1, wherein the nanoparticles are constructed to seek out and attach to target cells with specific vectors, and wherein the coherent energy externally applied to the nanoparticles via the system generates heat and dissolves the protective coating of the nanoparticles, providing controlled release of the therapeutic agents only to target cells.

16. The method of claim 1, wherein the location of nanoparticles is monitored to visualize the reaction of nanoparticles energized by the coherent energy in the first region.

17. The method of claim 1, wherein said coherent energy in said first region is monitored to provide information about the status and make-up of structures within said first region which can be used for imaging said structures.

* * * * *